(12) United States Patent
Thompson et al.

(10) Patent No.: US 9,347,948 B2
(45) Date of Patent: May 24, 2016

(54) PHENYL GLYOXAL PROBES

(71) Applicant: The Scripps Research Institute, La Jolla, CA (US)

(72) Inventors: Paul R. Thompson, Jupiter, FL (US); Kevin L. Bicker, Jupiter, FL (US); Venkataraman Subramanian, Palm Beach Gardens, FL (US)

(73) Assignee: The Scripps Research Institute, LaJolla, CA (US)

( * ) Notice: Subject to any disclaimer, the term of this patent is extended or adjusted under 35 U.S.C. 154(b) by 0 days.

(21) Appl. No.: 14/405,467

(22) PCT Filed: Jun. 4, 2013

(86) PCT No.: PCT/US2013/044048
§ 371 (c)(1),
(2) Date: Dec. 4, 2014

(87) PCT Pub. No.: WO2013/184645
PCT Pub. Date: Dec. 12, 2013

(65) Prior Publication Data
US 2015/0148259 A1    May 28, 2015

Related U.S. Application Data

(60) Provisional application No. 61/655,098, filed on Jun. 4, 2012.

(51) Int. Cl.
| | | |
|---|---|---|
| *C07C 45/00* | (2006.01) | |
| *C07C 49/00* | (2006.01) | |
| *C07C 247/00* | (2006.01) | |
| *C07D 311/00* | (2006.01) | |
| *C07D 495/00* | (2006.01) | |
| *C07B 59/00* | (2006.01) | |
| *G01N 33/68* | (2006.01) | |
| *C12Q 1/34* | (2006.01) | |
| *G01N 33/532* | (2006.01) | |
| *C07C 49/86* | (2006.01) | |
| *C07C 247/04* | (2006.01) | |
| *C07C 45/61* | (2006.01) | |
| *C07D 311/86* | (2006.01) | |
| *C07D 311/90* | (2006.01) | |
| *C07D 495/04* | (2006.01) | |
| *G01N 33/58* | (2006.01) | |
| *G01N 33/92* | (2006.01) | |

(52) U.S. Cl.
CPC ............ *G01N 33/6803* (2013.01); *C07B 59/00* (2013.01); *C07C 45/61* (2013.01); *C07C 49/86* (2013.01); *C07C 247/04* (2013.01); *C07D 311/86* (2013.01); *C07D 311/90* (2013.01); *C07D 495/04* (2013.01); *C12Q 1/34* (2013.01); *G01N 33/532* (2013.01); *G01N 33/581* (2013.01); *G01N 33/582* (2013.01); *G01N 33/583* (2013.01); *G01N 33/68* (2013.01); *G01N 33/92* (2013.01); *C07B 2200/05* (2013.01); *G01N 2333/775* (2013.01); *G01N 2333/978* (2013.01); *G01N 2440/18* (2013.01); *G01N 2458/15* (2013.01); *G01N 2500/00* (2013.01); *G01N 2570/00* (2013.01)

(58) Field of Classification Search
CPC ...... C07C 45/61; C07C 49/86; C07C 243/04; C07D 495/04; C07D 311/86; C07D 311/90; C07B 59/00; G01N 33/532; G01N 33/92
USPC ............ 568/309, 335; 549/223, 394; 506/12; 435/7.2, 7.94, 29, 86, 501
See application file for complete search history.

(56) References Cited

FOREIGN PATENT DOCUMENTS

WO    WO2008138916    1/2005

OTHER PUBLICATIONS

Wang et al. Detection of local polarity and conformational changes at the active site of rabbit muscle creatine kinase with a new arginine-specific fluorescent probe. Biochemica et Biophysica Acta 1784 (2008) 415-422.*
Ngo et al. p-Azidophenylglyoxal. A Heterobifunctional Photoactivatable Cross-Linking Reagent Selective for Arginyl Residues. The Journal of Biological Chemistry, vol. 256 (21), 1981, pp. 11313-11318.*
Matsuo et al. Identification of novel citrullinated autoantigens of synovium in rheumatoid arthritis using a proteomic approach. Arthritis Research & Therapy, 2006, 1-13.*
Jones, J. et al, "Protein arginine deiminase 4 (PAD4): current understanding and future therapeutic potential", Current Opinion Drug Discovery Development, 12:5:616-627, (2009).
Kinloch, A. et al, "Synovial fluid is a site of citrullination of autoantigens in inflamatory arthritis", Arthritis & Rheumatism, 58:8:2287-2295, (2008).
Wang, Y. et al, "Histone hypercitrullination mediates chromatin decondensation and neutrophil extracellular trap formation", Journal of Cellular Biology, 184:2:205-213, (2009).
Wood, D. et al, "Myelin localization of peptidylarginine deiminases 2 and 4: comparison of PAD2 and PAD4 activities", Laboratory Investigation, vol. 88, pp. 354-364, (2008).

(Continued)

*Primary Examiner* — Sikarl Witherspoon
(74) *Attorney, Agent, or Firm* — McHale & Slavin, P.A.

(57) ABSTRACT

Novel phenyl-glyoxal based anti-citrulline probes and methods of synthesis are provided. Methods of use, such as, the development of methods for monitoring substrate citrullination over time; for identifying citrullinated proteins from cells are described.

8 Claims, 18 Drawing Sheets

(56) References Cited

OTHER PUBLICATIONS

Eriksson, M. et al, "Hereditary apolipoprotein Al-associated amyloidosis in surgical pathologyspecimens", Journal of Molecular Diagnostics, 11:3:257-262, doi: 10.2353/jmoldx.2009.080161, (2009).

Bicker, K. et al, "The protein arginine deiminases (PADs): structure, function, inhibition, and disease", Journal of American Chemistry Society, 134:41:17015-17018, (2011).

Schweitzer, B. et al, "Multiplexd protein profiling on microarrays by rolling-circle amplification", Nature Biotechnology, 20:4:359-365, (2002).

Chang, X. et al, "Increased PADI4 expression in blood and tissues of patients with malignant tumors", BMC Cancer, vol. 9, p. 40, (2009).

Luo, Y. et al, "Inhibitors and inactivatoors of protein arginine deiminase 4: functional and structural characterization", Biochemistry, 45:39:11727-11736, (2006).

Chumanevich, A. et al, "Supression of colitis in mice by CI-amidine: a novel peptidylarginine deiminase inhibitor", American Journal of Physiology—Gastrointestinal and Liver Physiology, 300:6:G929-G938, (2011).

Willis, V. et al, "N-a-benzoyl-N5-(2-chloro-1-iminoethyl)-L-ornithine amide, a protein arginine deiminase inhibitor, reduces the severity of murine collagen-induced arthritis", Journal of Immunology, 186:7:4396-4404, (2011).

Slack, J. et al, Autodeimination of protein arginine deiminase 4 alters protein-protein interactions but not activity, Biochemistry, 50:19:3997-4010, (2011).

Hou, Y. et al, "Effects of alanyl-glutamine dipeptide on the expression of colon-inflammatory mediators during the recovery phase of colitis induced by dextran sulfate sodium", European Journal of Nutrition, 52:3:1089-1098, DOI: 10.1007/s00394-012-0416-3, (2012).

Vowinkel, T. et al, "Apolipoprotein A-IV inhibits experimental colitis", Journal of Clinical Investigation, 114:2:260-269, (2004).

Takahashi, K, "The Reaction of Phenylglyoxal with Arginine Residues in Proteins", The Journal of Biological Chemistry, pp. 6171-6179, pp. 6171-6179, XP055234510, (1968).

De Ceuleneer, M. et al, "In vivo relevance of citrullinated proteins and the challenges in their detection", Proteomics, 12:6:752-760, XP055096319, ISSN: 1615-9853, 001: 10.1002/pmic.201100478, paragraph [4.2.1] Mar. 1, 2012).

Augustus, B. et al, "The Synthesis of Phenyl [2-3H]glyoxal", Biochem. J., pp. 377-379, XP055234053, (1979).

Takahashi, K, "The Reaction of Phenylglyoxal with Arginine Residues in Proteins*", The Journal of Biological Chemistry, pp. 6171-6179, pp. 6171-6179, XP055234510, (1968).

Lundblad, R., "The Modification of Arginine", In: "Techniques in protein modification", CRC Press, pp. 1-27, XP055234269, (Jan. 1, 2005).

* cited by examiner

A.

B.

PHENYL GLYOXAL PROBES

CROSS REFERENCE TO RELATED APPLICATIONS

This is a national stage filing in accordance with 35 U.S.C. §371 of PCT/US2013/044048, filed Jun. 4, 2013, which claims the priority to U.S. provisional patent application No. 61/655,098 entitled "Novel Phenyl Glyoxal Probes" filed Jun. 4, 2012, which are incorporated herein by reference in its entirety.

STATEMENT REGARDING FEDERALLY SPONSORED RESEARCH

This invention was made with government support under Grant No. GM079357 awarded by the National Institutes of Health. The government has certain rights in the invention.

FIELD OF THE INVENTION

Embodiments of the invention are directed to phenyl glyoxal probes, methods of synthesis, methods of identifying citrullinated proteins and uses thereof.

BACKGROUND

The Protein Arginine Deiminases (PADs) are a family of enzymes that catalyze the post-translational conversion of peptidyl-arginine to peptidyl-citrulline, a process more commonly referred to as deimination or citrullination (Jones, J. E., Causey, C. P., Knuckley, B., Slack-Noyes, J. L., and Thompson, P. R. (2009), *Curr Opin Drug Discov Devel* 12, 616-627; Vossenaar, E. R., et al. (2003), *Bioessays* 25, 1106-1118). There are five PAD isozymes in humans and other mammals (which are denoted PADs 1, 2, 3, 4, and 6), and the activity of multiple family members is aberrantly increased in different diseases, including rheumatoid arthritis (RA), Alzheimer's disease (AD), multiple sclerosis (MS), lupus, Parkinson's disease, and cancer. For example, increased PAD levels are observed in synovial fluid (RA) (Kinloch, A., et al. (2008), *Arthritis Rheum.* 58, 2287-2295) during NET formation (colitis and lupus) (Wang, Y., et al. (2009), *J. Cell. Biol.* 184, 205-213), within the brains of patients with MS (Wood, D. D., et al. (2008), *Lab. Invest.* 88, 354-364), in the joints of patients with osteoarthritis (Kinlock A., et al. (2008), in ulcerative colitis lesions (Chen, C. C., et al. (2008), *Clin. Immunol.* 126, 165-171), in the hippocampal extracts of AD patients (Ishigami, A., et al. (2005), *J. Neurosci. Res.* 80, 120-128), and in several types of carcinomas (Chang X., et al. (2009), *BMC Cancer* 9, 40). Furthermore, the administration of Cl-amidine, a potent PAD inhibitor (Luo, Y., et al. (2006), *Biochemistry* 45, 11727-11736), has proven useful in decreasing disease severity in animal models of ulcerative colitis and RA (Chumanevich, A. A., et al. (2011), *American Journal of Physiology—Gastrointestinal and Liver Physiology* 300, G929-G938; Willis, V. C., et al. (2011) *J. Immunol.* 186, 4396-4404).

SUMMARY

This Summary is provided to present a summary of the invention to briefly indicate the nature and substance of the invention. It is submitted with the understanding that it will not be used to interpret or limit the scope or meaning of the claims.

Embodiments of the invention are directed to the design and synthesis of phenyl glyoxal based anti-citrulline probes. These probes further comprise a reporter moiety, for example, rhodamine, biotin, or isotopically-labeled phenyl glyoxal based probes.

Other embodiments are directed to, inter alia, methods for monitoring substrate citrullination over time; methods for identifying citrullinated proteins from cells; use of these probes in diagnosis of diseases associated with abnormal Protein Arginine Deiminases (PAD) activity; drug discovery, identification of biomarkers that are citrullinated in specific disease states, and the like.

Other aspects are described infra.

BRIEF DESCRIPTION OF THE DRAWINGS

FIG. 5A: Coomassie and fluorescent images. FIG. 5B: Quantitation of the data in FIG. 5A indicates that the limit of detection for peptidyl-citrulline by the Rh-PG probe is 1 ng of autodeiminated PAD4.

FIG. 16A shows varying amounts of citrullinated histone H3 and (FIG. 16B) varying amounts of autocitrullinated PAD4 were labeled with Rh-PG. These data indicate that the limit of detection of the Rh-PG probe is in the femtomole range.

FIG. 19A: Fluorescent image of Rh-PG analyzed serum samples. Serum samples are from mice treated with DSS to induce ulcerative colitis (left seven lanes) and mice treated with DSS as well as the PAD inhibitor, Cl-amidine (right seven lanes). FIG. 19B: Analysis of the gel indicates Cl-amidine significantly decreases global citrullination (whole lane) as well as specific protein bands (10, 25, 50, 70, and 100 kDa). Unlike other methods for analyzing serum citrullination, the Rh-PG probe allows for the study of specific protein bands.

FIG. 20A: A representative correlation plot of Rh-PG labeled protein fluorescence versus colon length in the mouse model of ulcerative colitis. As citrullination of the 25 kDa protein increase, colon length decreases proportionally. FIG. 20B: Correlation coefficients of Rh-PG labeled protein fluorescence versus various disease scorings in the mouse model of ulcerative colitis. These data indicate that (1) The 10 kDa protein, which did not show a significant decrease in citrullination in response to Cl-amidine, has no significant correlations, thereby serving as a negative control; (2) Most of the proteins with significant decreases in citrullination in response to Cl-amidine have significant correlations with the disease markers "colon length" and "inflammation score," markers which serve as the best predictors of disease severity; and (3) The 25 kDa protein has significant correlations with 4 out of 5 disease markers, indicating that this proteins is likely a novel citrullinated disease biomarker and could be used to monitor disease severity.

FIG. 21A is a schematic representation of a structure of a Biotin-PG probe. FIG. 21B is a blot showing varying amounts of citrullinated H3 which were treated with Biotin-PG under acidic conditions, separated by SDS-PAGE, transferred to nitrocellulose, and probed with streptavidin HRP. FIG. 21C: Quantification indicates the limit of detection for the Biotin-PG probe is around 10 ng of citrullinated H3, which gives a limit of detection similar to the Rh-PG probe in the femtomole range.

FIGS. 22A to 22C are blots showing results from streptavidin-agarose pulldown of biotin-PG labeled citrullinated H3. Histone H3 was incubated with PAD2 for 0, 1, or 3 minutes. These samples were then treated with Biotin-PG under acidic conditions ±MCF whole cell extracts. Western blotting using streptavidin-HRP (top) and silver staining (bottom) of: (FIG. 22A) 20% loading control indicating citrulline dependent labeling of H3, even in the MCF7 extracts; FIG. 22B: Elution of isolated Biotin-PG labeled citrullinated H3; and FIG. 22C: The supernatant from the pulldown indicating complete isolation of Biotin-PG labeled citrullinated H3.

FIG. 24A: Anti-ApoA1 Western blotting of Biotin-PG pulldown samples showing citrullinated ApoA1 in UC serum. FIG. 24B: Recombinant ApoA1 as treated ±PADs 1-4 and analyzed with the Rh-PG probe. A strong increase in fluorescence indicates that ApoA1 is likely a good PAD1 substrate and moderate substrate of PADs 2-4. FIG. 24C: Kinetic characterization of ApoA1 as a PAD substrate using the Rh-PG probe. ApoA1 is the strongest protein substrate of a PAD (PAD1) with a $k_{cat}/K_m$ of 19600 $M^{-1}s^{-1}$.

DETAILED DESCRIPTION

Figure 1:
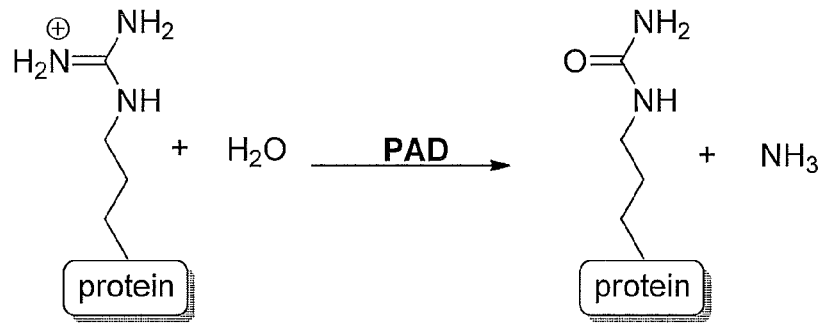
FIG. 1 is a schematic representation showing that PADS catalyze the hydrolysis of arginine to citrulline.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Any genes, gene names, gene products or peptides disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes, nucleic acid sequences or peptides are human.

DEFINITIONS

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, preferably up to 5%, or preferably up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "biomarker" or "marker" as used herein refers to a peptide, polypeptide, protein that is differentially citrullinated in samples from individuals at risk of, or suffering from, a disease or disorder associated with the aberrant citrullination of proteins. These biomarkers vary from disease state to disease state and can be diagnosed based on the citrullination profile of these markers. For example, if these samples are obtained from a patient with ulcerative colitis, the samples are analyzed to identify markers which may be differentially citrullinated in these individuals. Thus, these marker and/or marker citrullination profiles can be classified according to a specific disease or disorder. Valuable information such as, diagnosis, prognosis, response to a particular therapy, etc., and thus may be predictive of different survival outcomes and of the benefit of the therapy.

The term "citrullination profile" refers to the differential citrullination of markers due to a disease or disorder. The term "differential citrullination" is wherein citrullination of one or more markers is increased, decreased or remains at baseline levels relative to each other and baseline normal controls. The citrullination profile is typically identified using one or more samples from a patient, wherein the citrullination is similar between related samples defining a class or group such as, a specific disease or disorder, for example, differential diagnosis of an inflammatory disease (e.g. rheumatoid arthritis versus ulcerative colitis) and is different to unrelated samples defining a different class such that the reference citrullination profile is associated with a particular disease. The marker citrullination profile is accordingly a reference profile or reference signature of the citrullination of at least 1 or more identified biomarkers from patients. The citrullination profiles are compared to a control in methods for diagnosing a disease, predicting clinical outcome, therapeutic responsiveness etc.

As used herein, the term "control" refers to a specific value or dataset that can be used to arrive at a prognosis or classify the value e.g. marker citrullination, marker expression level or marker expression and/or citrullination profile obtained from the test sample associated with a defined class. In one embodiment, a dataset may be obtained from samples from a group of subjects known to have a specific disease or disorder and good survival outcome or good responsiveness to a particular therapy, or, have poor survival outcome or known to have a specific disease or disorder and have benefited from a particular therapy or known to have a specific disease or disorder and not have benefited from a particular therapy. The expression data of the biomarkers in the dataset can be used to create a control value that is used in testing samples from new patients. In such an embodiment, the "control" is a predetermined value for the set of at least 1 biomarker obtained from patients having a specific disease or disorder (e.g. ulcerative colitis, rheumatoid arthritis etc.) whose biomarker citrullination values and clinical outcomes times are known. Alternatively, the "control" is a predetermined reference profile for the set of one or more biomarkers described herein obtained from patients whose disease states, responsiveness to a particular therapy, etc., are known.

A person skilled in the art will appreciate that the comparison between the citrullination of the biomarkers in the test sample and the citrullination of the biomarkers in the control will depend on the control used. For example, if the control is from a subject known to have a specific inflammatory or autoimmune disease and disorder and/or, for example, poor responsiveness to a particular therapy and/or poor survival, and there is a difference in citrullination or citrullination profiles of the biomarkers between the control and test sample, then the subject can be diagnosed, or classified in a good survival group. If the control is from a subject known to have a specific inflammatory or autoimmune disease or disorder and there is a difference in citrullination or citrullination profiles of the biomarkers between the control and test sample, then the subject can be classified as not having that specific disease or disorder. Thus, one of skill in the art, can select the controls based on the desired diagnostic, prognostic or any other parameters, e.g. therapeutic responsiveness.

A "control subject" is a healthy subject, i.e. a subject having no clinical signs or symptoms of a particular disease or disorders. Preferably a control subject is clinically evaluated for otherwise undetected signs or symptoms of a particular disease or disorder, which evaluation may include blood tests, CAT scans, X-rays or other routine laboratory testing.

As used herein, "a control sample" refers to a control sample that is only different in one or more defined aspects relative to a test sample, and the present methods, kits or arrays are used to identify the effects, if any, of these defined difference(s) between the test sample and the control sample. For example, the control sample can be derived from physiological normal conditions and/or can be subjected to different physical, chemical, physiological or drug treatments, or can be derived from different biological stages, etc.

The term "disease" as used herein, is meant to encompass all diseases in which citrullination of proteins are aberrantly affected. "Aberrantly affected" includes, without limitation, the target protein being citrullinated or not, the numbers of proteins that are being citrullinated or not, the rate of protein citrullination, the half-life of citrullinated proteins, and the like. The term disease includes all of the diseases associated with protein arginine deiminases (PADs).

The term "diseases associated with protein arginine deiminases (PADs)" is meant to encompass all diseases in which the PAD activity is aberrantly affected. For example, PAD activity is aberrantly increased in different diseases, such as, for example, rheumatoid arthritis (RA), ulcerative colitis (UC), Alzheimer's disease (AD), multiple sclerosis (MS), lupus, Parkinson's disease (PD) and cancer.

"Biological samples" include solid and body fluid samples. The biological samples used in the present invention can include cells, protein or membrane extracts of cells, blood or biological fluids such as ascites fluid or brain fluid (e.g., cerebrospinal fluid). Examples of solid biological samples include, but are not limited to, samples taken from tissues of the central nervous system, bone, breast, kidney, cervix, endometrium, head/neck, gallbladder, parotid gland, prostate, pituitary gland, muscle, esophagus, stomach, small intestine, colon, liver, spleen, pancreas, thyroid, heart, lung, bladder, adipose, lymph node, uterus, ovary, adrenal gland, testes, tonsils and thymus. Examples of "body fluid samples" include, but are not limited to blood, serum, semen, prostate fluid, seminal fluid, urine, saliva, sputum, mucus, bone marrow, lymph, and tears. "Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The term "prognosis" as used herein refers to a clinical group associated with a disease or disease subtype which is reflected by a reference profile such as a citrullination profile of markers or reflected by a single marker which is citrullinated or is not citrullinated as compared to a normal control. The prognosis provides an indication of disease progression, responsiveness to a particular treatment or drug(s), identifies at risk patients and includes an indication of likelihood of death due to a disease or disorder.

The term "prognosing" or "classifying" as used herein means predicting or identifying the clinical outcome group that a subject belongs to according to the subject's similarity to a reference citrullination profile or biomarker associated with the prognosis.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein, the term "individual", "animal", "subject" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids. "Mammal" covers warm blooded mammals that are typically under medical care (e.g., humans and domesticated animals). Examples include feline, canine, equine, bovine, and human, as well as just human. Preferably, the patient is human.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

"Detectable label", "reporter moiety", "detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, or flow cytometry.

Phenyl Glyoxal Probes

Although abnormally high PAD activity and protein citrullination is observed in various diseases, the exact role(s) and target(s) of these enzymes are still poorly understood, in part due to a lack of proteomics tools that can be used to identify the proteins that are citrullinated within a specific disease model.

Citrulline metabolism falls into two categories: free citrulline and citrullinated proteins. Although citrulline cannot be incorporated into proteins during protein synthesis, some proteins contain citrulline residues. These proteins are modified post-translationally, by the conversion of arginine residues to citrulline by PADs. Thus, diseases associated with protein citrullination include, without limitation: chronic autoimmune diseases, Alzheimer's disease, lupus, cancer, inflammatory diseases. Environmental factors that may also affect citrullination of proteins is radiation. Thus, measurements of citrullinated proteins allows for an assessment of the injury and exposure. Less well documented cases include citrullination of B23 nucleophosmin and some histones in leukocyte nuclei and PAD1 activity in decidual cells of the female genital system.

The ability to investigate the specific target and role of the PADs in these diseases or related injuries due to environmental factors, allows for better, more tailored treatments, and identify biomarkers that can be used to diagnose and monitor the efficacy of treatments for these diseases. Additionally, the ability to rapidly detect changes in protein citrullination in response to the addition of a PAD inhibitor will facilitate the development of such compounds. In general, embodiments are directed to the identification of proteins that are citrullinated in a disease associated with high PAD activity, identification of biomarkers, patterns and changes in protein citrullination, identification of novel PAD inhibitors for treatment of diseases associated with PAD activity, diagnosis and identification of at-risk subjects for diseases associated with PAD activity, prediction and prognostic outcome of patient response to a treatment, isolation and identification of citrullinated proteins. Further, general embodiments are directed to the novel phenyl glyoxal probes (PG), synthesis of PG probes, labeling of PG probes and uses thereof.

Prior to the methods described in detail the examples section following, common methods for studying citrullination include the Color Development Reagent (COLDER) assay and a commercially available Anti-Citrulline (Modified) Detection Kit (Millipore; Billerica, Mass.). Although widely used for studying small molecule and peptide substrates of the PADs, the COLDER assay has a relatively high limit of detection (LOD) making it difficult to use with less concentrated protein substrates. The Anti-modified Citrulline antibody kit has also proven useful, but suffers from relatively high cost ($40/assay) and a lengthy two day procedure. Although other means of detecting citrullinated proteins have been described, these are also antibody based. For example, the F95 antibody, which was developed to recognize citrullinated Myelin Basic Protein, can be used to detect many, but not all, citrullinated proteins. Unfortunately, this antibody is not commercially available. While a small number of antibodies (~10) targeting citrullinated proteins are commercially available, these antibodies recognize only a limited subset of proteins (e.g., citrullinated histone H3), thereby limiting their utility. In contrast, the probes described herein provide many advantages. For example, they are readily synthesized, show excellent sensitivity, they react with any citrulline bearing protein, and can be used by most users without the need for rare or expensive equipment or reagents.

In one embodiment, synthesis and labeling of PG probes comprises synthesizing compounds wherein the phenylglyoxal is linked to the reporter tag via the meta position. In embodiments, to permit functionalization to reporter tags before or after reaction with either citrulline or arginine, azide bearing PG probes were synthesized that can be "clicked" to an alkyne bearing reporter tag. An embodiment of a method for synthesizing various PG probes is shown in Scheme 1 and described in detail in the examples section which follows.

In embodiments, a method of synthesizing phenylglyoxal (PG) probes comprises use of a compound having an azido group, such as, for example, azido acetophenones, to produce azido-PG. Examples are the compounds having a general structure of 5 or 10:

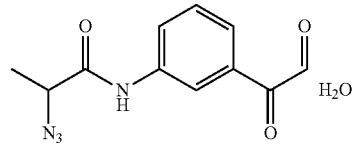

5

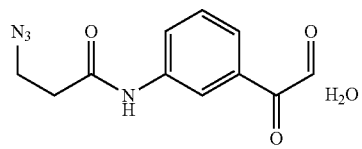

10

In embodiments, the compounds having the general structures of compounds 5 and 10 are reacted with an alkyne comprising a reporter moiety. The reporter moiety can be any type which would provide a detectable signal. For example, labeling or reporter moieties can include compositions that can be detected by spectroscopic, biochemical, photochemical, bioelectronic, immunochemical, and electrical optical or chemical means. Examples of labeling moieties include, but are not limited to, radioisotopes, e.g., $^{32}P$, $^{33}P$, $^{35}S$, chemiluminescent compounds, labeled binding proteins, heavy atoms, spectroscopic markers such as fluorescent markers and dyes, linked enzymes, mass spectrometry tags, and magnetic labels.

In embodiments, a reporter or labeling moiety comprises: fluorophores, isotopes, or biotin. In embodiments, a fluorophore labeled phenylglyoxal comprises: rhodamine labeled phenylglyoxal (Rh-PG) or fluorescein labeled phenylglyoxal. In yet other embodiments, the fluorophore labeled phenylglyoxal comprises: rhodamine labeled phenylglyoxal (Rh-PG) or fluorescein labeled phenylglyoxal. Structures of a biotin-PG and an Rh-PG are shown below:

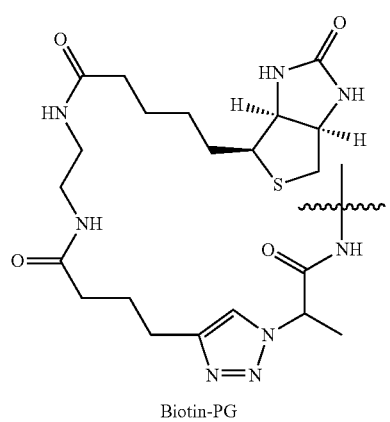

Biotin-PG

-continued

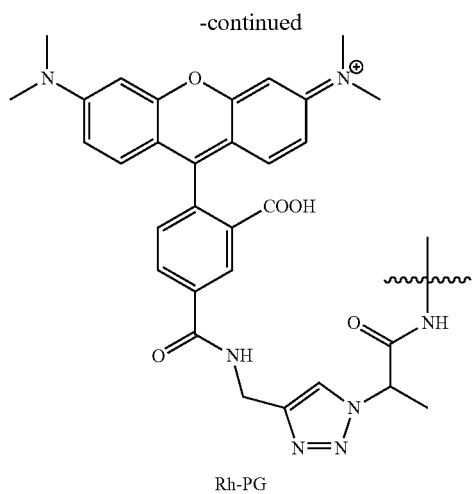

Rh-PG

In preferred embodiments, the phenylglyoxal is linked to the reporter moiety via the meta position.

In another embodiment, an isotopically labeled phenylglyoxal compound is heavy phenylglyoxal ($PG_H$) or light phenylglyoxal ($PG_L$) having a phenylglyoxal having a general structure I:

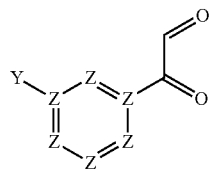

wherein Z is $^{13}C$ for heavy phenylglyoxal ($PG_H$), Z is $^{12}C$ for light phenylglyoxal ($PG_L$) and Y is H.

The phenyl glyoxal probes and the methods developed to utilize them hold several advantages over common and commercial methods for studying citrullination. For example, the isotopic probes, coupled with LC-MS analysis, lends them excellent sensitivity, making them advantageous versus common methods for studying citrullination, such as the COLor DEvelopment Reagent (COLDER) assay. For these probes, significantly less protein, peptide, or small molecule is needed comparable to COLDER analysis, thereby saving materials. For the fluorescently labeled phenyl glyoxal probes (e.g., Rhodamine-PG), as stated earlier, these probes compare favorably with the already commercially available Anti-Citrulline (Modified) Detection Kit. However, note that compared to this kit, the Rh-PG labeling method takes significantly less time (~5 h versus ≥25 h), requires fewer steps (6 versus 12), and simpler analysis (fluorescent imaging versus Western blotting). These reasons make the Rh-PG probe extremely advantageous over this system in studying protein citrullination. The Biotin-PG probe is unique in that no other tools are available for selectively isolating and enriching citrullinated proteins from complex matrices. This probe allows for, inter alia, the isolation of citrullinated disease biomarkers from serum or tissue samples, enrichment for these biomarkers, and identification of these biomarkers using standard techniques, such as for example, proteomic methods.

The uses for the PG probes embodied herein are limited only by the mind of the user. In preferred embodiments, the PG probes are labeled with a detectable label. In embodiments, the detectable label comprises: fluorophores, chromophores, isotopes, chemiluminescent molecules, fluorescent molecules, enzymes or co-enzymes.

In an embodiment, a method of labeling citrullinated proteins protein or fragments thereof in a biological sample, comprises contacting a biological sample with an effective amount of a phenylglyoxal probe, wherein the probe is detectably labeled and the detectably labeled phenylglyoxal probe is covalently bonded to a citrullinated protein or fragments thereof in the biological sample. In preferred embodiments, the phenylglyoxal probe comprises a heavy phenylglyoxal ($PG_H$) or light phenylglyoxal ($PG_L$) having a general structure I:

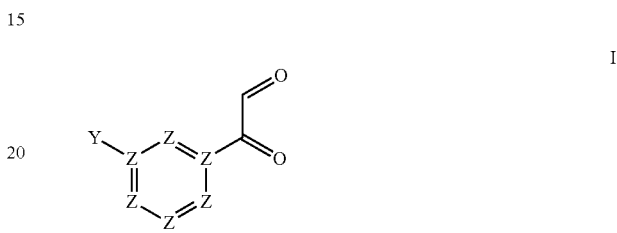

wherein Z is $^{13}C$ for heavy phenylglyoxal ($PG_H$), Z is $^{12}C$ for light phenylglyoxal ($PG_L$) and Y is H.

In other embodiments, the detectable label comprises: fluorophores, chromophores, isotopes, chemiluminescent molecules, fluorescent molecules, enzymes or co-enzymes. In some embodiments, the fluorophore comprises rhodamine or fluorescein and the co-enzyme is biotin.

In embodiments, the step of contacting the biological sample with the phenylglyoxal probe is conducted in a medium having a pH value of about 0.001 to about 13.9. In some preferred embodiments, the step of contacting the biological sample with the phenylglyoxal probe is conducted in a medium having a pH value of about 0.001 to about 6.9. In another preferred embodiments, the step of contacting the biological sample with the phenylglyoxal probe is conducted in a medium having a pH value of about 6.9 to about 13.9.

In some embodiments, the labeled citrullinated protein is detectable by assay means comprising: gels, blots, chromatography, fluorescence, chemiluminescence, or immunoassays.

In one embodiment, a method of identifying biomarkers of a disease comprises contacting a biological sample with an effective amount of a phenylglyoxal probe, wherein the probe is detectably labeled and the detectably labeled phenylglyoxal probe specifically attaches (e.g. via a covalent bond) to a citrullinated protein or fragments thereof in the biological sample; thereby, labeling the citrullinated protein or fragments thereof in the biological sample; and, identifying a citrullination profile of citrullinated proteins or fragments thereof; comparing the citrullination profile of citrullinated proteins or fragments thereof in control samples as compared to a patient sample; thereby, identifying biomarkers of a disease.

In some embodiments, the biomarkers of a disease comprise one or more citrullinated proteins or fragments thereof. In other embodiments, the biomarkers of a disease comprise a citrullination profile of citrullinated proteins or fragments thereof, wherein the citrullination profile comprises at least two citrullinated proteins or fragments thereof having varying concentrations of citrullination and/or citrullinated proteins.

In one embodiment, a biomarker for the prognosis and/or diagnosis of a subject suffering from or at risk of developing ulcerative colitis comprises apolipoprotein A1 (ApoA1), mutants, variants or fragments thereof. In preferred embodiments, the ApoA1 marker is a protein, mutants, variants or fragments thereof. In other embodiments, the ApoA1 marker is a nucleic acid, mutants, variants or fragments thereof. In other embodiments the ApoA1 marker comprises proteins, nucleic acids, mutants, variants, fragments or combinations thereof. In preferred embodiments, the ApoA1 marker is citrullinated.

In another embodiment, a biomarker for the prognosis and/or diagnosis of a subject suffering from or at risk of a developing a disease associated with lipoproteins comprises apolipoprotein molecules, enzymes or coenzymes. Examples of apolipoprotein molecules includes one or more classes or subclasses of apolipoproteins, such as, apoA (apo A-I, apo A-II, apo A-IV, apo A-V), apoB (apo B48, apo B100), apoC (apo C-I, apo C-II, apo C-III, apo C-IV), apoD, apoE, apoH. In preferred embodiments, the apolipoprotein markers are citrullinated.

In embodiments, a method to determine rate and extent of citrullination comprise the selective labeling of arginine and citrulline residues under various pH values using the isotopic PG probes.

In other embodiments, citrullinated proteins are labeled with the PG probes and analyzed by various techniques, such as for example, electrophoresis or Western blotting techniques. This includes labeling of purified proteins and proteins present in cellular extracts and serum.

In other embodiments, the present invention provides methods for isolating, enriching, or purifying citrullinated peptides, polypeptides, or proteins from a solution or sample. The methods comprise contacting a sample with at least one PG probe, wherein the PG probe becomes covalently attached to at least one citrullinated protein. The citrullinated proteins bound by the PG probes can be separated via a variety of techniques known ion the art.

In certain embodiments, the PG probes are used to facilitate purification of citrullinated proteins from complex mixtures, such as biological samples. In certain embodiments, the PG probes of general formula or general structure I comprise a molecular tag. The tag can be a compound that specifically binds to, for example, avidin/streptavidin, monomeric avidin, and the like, such as biotin or iminobiotin. The PG-protein complexes can then be isolated using magnetic or other beads coated with avidin/streptavidin. Alternatively, any of a number of commonly used chromatography substrates can be similarly coated with avidin/streptavidin and used to isolate the proteins.

Examples of methods for isolation and separation of citrullinated proteins are described in detail in the Examples section which follows. These methods can be used alone, or in conjunction with other routine methods of protein purification known to one skilled in the art, such as size fractionation, density gradient centrifugation, ultrafiltration, ammonium sulfate precipitation, cation or anion exchange chromatography, and the like, if necessary to reduce the complexity of the solution or sample.

Examples of methods for identification or visualization can include using commercially available antibodies modified with appropriate conjugates to identify cognate ligands by colorimetric, autoradiographic, or other types of detection. For example, antibodies conjugated with horseradish peroxidase and tetramethylbenzidine, or using alkaline phosphatase and any suitable phosphatase substrate. If detected colorimetrically, the amount of color may be measured using a luminometer, a spectrophotometer, or other similar instruments. If detected autoradiographically, the amount of signal may be measured from exposed x-ray film using a densitometer, directly from a gel or blot using a PHOSPHORIMAGER™ or similar instrument, or in solution using a luminometer. These methods can be used alone, or in conjunction with other routine methods of detecting proteins known to one skilled in the art, such as Western blotting or in situ immunohistochemistry. Such methods may further comprise fixation of proteins, either in situ (e.g., by formalin fixation, paraffin-embedding, and thin sectioning), or by electrophoresis and blotting (e.g., by SDS-PAGE and Western blotting). Other permutations and possibilities for selecting additional appropriate methods of detection will be readily apparent to one of ordinary skill in the art.

In another preferred embodiment, a method for testing the bioavailability of PAD inhibitors comprises incubating the sample with one or more labeled PG probes and comparing the results with appropriate controls.

In another preferred embodiment, a method for binding citrullinated proteins from serum or cellular extracts comprises contacting a sample with one or more PG probes, isolating those proteins, for example, by affinity chromatography, and identifying those proteins by, for example, proteomic methods.

In another preferred embodiment, a method for classifying serum, cells and tissues, comprises contacting a sample with one or more PG probes and comparing the overall protein citrullination patterns.

In another embodiment, a method for discriminating between diseased and healthy cells, serum, and tissues, comprises contacting a sample with one or more PG probes and analyzing the overall protein citrullination pattern.

In another embodiment, a method for performing immunohistochemistry comprises contacting a sample with one or more PG probes to determine the distribution and localization of citrullinated proteins within cell and tissue samples.

In another embodiment, a method for performing sandwich ELISAs comprises contacting a sample with one or more PG probes to determine the overall level of citrullinated proteins within serum or plasma samples.

As discussed above, the probes embodied herein, can be used in any standard assay to obtain a desired readout. For example, methods known to the skilled person, comprising but not limited to: mass spectrometry, Western blotting, immunoassays, protein assays, protein microarray etc.

In some embodiments, the methods of the present invention further include the step of performing mass spectrometry on a separated component, thereby analyzing the proteomics sample. Any number of spectrometric can be used in the present invention, e.g. tandem MS, LC-MS etc.

Optionally, methods and systems for identification of proteins using high mass accuracy mass spectrometry. An accurate mass measurement of the observed peptides can be also utilized to advantage in the analysis process. Accurate mass measurements, when compared to calculated nominal mass values for a series of theoretical compositions, can be used to determine whether a given MS peak represents a labeled species.

The samples can also be analyzed via high-throughput screening methods. In some embodiment, a protein microarray (Templin et al. 2004; *Comb. Chem. High Throughput Screen*, vol. 7, no. 3, pp. 223-229) consists of molecules (capture agents) bound to a defined spot position on a support material. The array is then exposed to a complex protein sample. The labeled probes are able to bind the protein of interest from the biological sample. The binding of the specific analyte proteins to the individual spots can then be monitored by quantifying the signal generated by each spot (MacBeath 2002; *Nat. Genet*, vol. 32 Suppl, pp. 526-532;

Zhu & Snyder 2003; *Curr. Opin. Chem. Biol.*, vol. 7, no. 1, pp. 55-63). Protein microarrays can be classified into two major categories according to their applications. These are defined as protein expression microarrays, and protein function microarrays (Kodadek 2001; *Chem. Biol.*, vol. 8, no. 2, pp. 105-115). Protein expression microarrays mainly serve as an analytic tool, and can be used to detect and quantify proteins, antigen or antibodies in a biological fluid or sample. Protein function microarrays on the other hand can be used to study protein-protein, enzyme-substrate and small molecule-protein interactions (Huang 2003; *Front Biosci.*, vol. 8, p. d559-d576). Protein microarrays also come in many structural forms. These include two-dimensional microarrays constructed on a planar surface, and three-dimensional microarrays which use a Flow-through support.

Types of protein microarray set-ups: reverse phase arrays (RPAs) and forward phase arrays (FPAs) (Liotta et al. 2003; *Cancer Cell*, vol. 3, no. 4, pp. 317-325). In RPAs a small amount of a tissue or cell sample is immobilized on each array spot, such that an array is composed of different patient samples or cellular lysates. In the RPA format, each array is incubated with one detection protein (e.g., labeled-PG probe), and a single analyte endpoint is measured and directly compared across multiple samples. In FPAs capture agents e.g. a labeled PG probe, are immobilized onto the surface and act as a capture molecule. Each spot contains one type of immobilized capture protein. Each array is incubated with one test sample, and multiple analytes are measured at once.

In other examples, a microarray can be produced in two forms, either by a sandwich assay or by direct labeling approach. The sandwich assay approach may utilize two different capture agents that bind the target protein. One agent is immobilized on a solid support and captures its target molecule from the biological sample. Using the appropriate detection system, the labeled-PG probe detects the bound targets. The main advantage of the sandwich assay is its high specificity and sensitivity (Templin, Stoll, Bachmann, & Joos 2004; *Comb. Chem. High Throughput. Screen.*, vol. 7, no. 3, pp. 223-229). High sensitivity is achieved by a dramatic reduction of background yielding a high signal-to noise ratio. The sandwich immunoassay format can also be easily amenable to the field of microarray technology, and such immunoassays can be applied to the protein microarray format to quantify citrullinated proteins in patient sera (Huang et al. 2001; *Clin. Chem. Lab Med.*, vol. 39, no. 3, pp. 209-214; Schweitzer et al. 2002; *Nat Biotechnol.*, vol. 20, no. 4, pp. 359-365).

In the direct labeling approach, citrullinated proteins in a sample are labeled by a PG probe having a reporter moiety, for example, a fluorophore. Proteins that bind to the PG probes on the microarray are then directly detected by fluorescence. An adaptation of the direct labeling approach is described by Haab and co-workers (Haab, Dunham, & Brown 2001; *Genome Biol.*, vol. 2, no. 2, p). In this approach, proteins from two different biological samples are labeled with either PG probes comprising Cy3 or Cy5 fluorophores. These two labeled samples can then be equally mixed together and applied to a microarray. This approach, for example, allows comparisons to be made between diseased and healthy, or treated and untreated samples. Miniaturized and multiplexed immunoassays may also be used to screen a biological sample for the presence or absence of citrullinated proteins (Joos et al. 2000; *Electrophoresis*, vol. 21, no. 13, pp. 2641-2650; Robinson et al. 2002; *Nat. Med.*, vol. 8, no. 3, pp. 295-301).

The detection or capture agents such as the probes are immobilized on a solid support, such as for example on a polystyrene surface. Examples of solid supports include, but are not limited to, membranes, filters, slides, paper, nylon, wafers, fibers, magnetic or nonmagnetic beads, gels, tubing, polymers, polyvinyl chloride dishes, etc.

In a method according to the invention, an individual has an increased risk of developing the symptoms of a disease associated with high PAD activity if the citrullination of proteins is increased or the overall expression pattern changes as compared to normal healthy controls or to a baseline sample from a patient. An overall expression pattern is classified as different when the expression pattern of the citrullinated product is statistically significantly increased or decreased or changed in an individual compared to the level of the same expression product found in control individuals or baseline sample of the individual. The term "significantly" or "statistically significant" refers to statistical significance and generally means a two standard deviation (SD) above normal, or higher, or below, or lower concentration of the expression product.

It is also possible to determine an increased risk of developing the symptoms of a disease associated with PAD activity by determining or identifying the proteins which become citrullinated over a period of time, the expression patterns of these citrullinated proteins by determining if the changes, be it, for example, increased citrullination, citrullination of previously uncitrullinated proteins, differ significantly from the same number in control individuals. In this way, biomarkers of different diseases associated with PAD activity can be identified and used as prognostic or diagnostic markers, as well as identifying whether a specific treatment is effective or even predicting whether a certain drug would be effective in treating that particular patient.

In other embodiments, the methods of the invention include obtaining a sample and contacting the sample with a PG probe having a labeled moiety under conditions effective to allow the labeling of citrullinated proteins. Details of such conditions are provided in the examples section which follows. The methods include methods for detecting or quantifying the amount of citrullinated proteins in a sample, via the detection or quantitation of any labeled complexes formed during the contact or incubating process, using an ELISA method. ELISA methods provide rapid, sensitive, and cost effective analyses of citrullinated proteins. In addition, the ELISA method is targeted to detect citrullinated proteins, rather than free citrulline, in the test sample, due to the small size of citrulline.

The test or biological sample analyzed may be any sample that is suspected of containing a citrullinated protein, including, but are not limited to, blood, plasma, serum, skin, urine, hair follicles, and other accessible tissues. The sample can be taken from any mammal, including humans, mice, rats, and nonhuman primates.

In the clinical diagnosis or monitoring of patients, the detection of varying or changed levels or overall patterns of citrullinated proteins, in comparison to the levels in a corresponding test sample from a control subject, is indicative of the patient's diagnosis or prognostic outcome.

Proteins from individuals can be isolated using techniques that are well-known to those of skill in the art. Expression of various biomarkers in a sample can be analyzed by a number of methodologies, many of which are known in the art and understood by the skilled artisan, including but not limited to, immunohistochemical and/or Western analysis, quantitative blood based assays (as for example Serum ELISA), biochemical enzymatic activity assays, as well as any one of the wide variety of assays that can be performed by protein and/or tissue array analysis. Typical protocols for evaluating the status of genes and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). A skilled artisan can readily adapt known protein/antibody detection methods for use in determining whether cells express a marker of the present invention and the relative concentration of that specific polypeptide expression product in blood or other body tissues.

The presence of the biomarker may be detected in a number of ways, such as, for example, by Western blotting, enzyme assays, spectrometry, and ELISA procedures for assaying a wide variety of tissues and samples, including plasma or serum.

Samples:

In some embodiments the samples used in the methods of the present invention are pre-fractionated. Exemplary pre-fractionated samples include, but are not limited to, gel electrophoresis bands, column chromatography fractions, and the like.

The methods of the present invention are performed on one or more biologically-derived samples, including, but not limited to, proteomics and metabolomics samples. These samples are complex compositions having a plurality of components, unlike organic reaction mixtures of chemical syntheses intermediates. As such, the methods of the present invention can be employed with samples having a plurality of sample members, e.g., biologically-derived preparations having at least 25 constituents, or at least 50 constituents, or at least 100 constituents, or at least 1,000 constituents, or even more complex populations of tens of thousands of constituents (for example, at least 10,000 components, 100,000 components, 1 million components, or more).

Exemplary embodiments of biologically-derived samples for use in the present invention include, but are not limited to, cell culture media which has been exposed to a cell/tissue/organism, various bodily fluids, waste products and/or excretions (e.g., blood, serum, urine, saliva, cerebrospinal fluid, interstitial fluid, and the like). Optionally, the samples can be collected from cells (or organisms) that have been treated with one or more members of a compound library.

In many embodiments, a cell lysate is used to provide a proteomics or metabolomics sample for use as the biologically-derived sample. Optionally, the sample is treated, e.g., using proteolytic enzymes or chemical cleavage reagents, to generate peptide fragments or to introduce a chemical functionality into a species to be analyzed.

In some embodiments of the present invention, the biologically-derived sample is treated with one or more proteinases prior to incubating with the PG probes having a reporter moiety. Exemplary proteolytic enzymes for use in the present methods include, but are not limited to, trypsin, chymotrypsin, endoprotease ArgC, aspN, glue, and lysC. Optionally, these proteinases (as well as any additional enzymes not specifically listed) can be used in combination to generate proteolytic fragments of the sample proteins.

Alternatively, constituents of the biological sample can be fragmented using a chemical cleavage reagent, such as cyanogen bromide, formic acid, trifluoroacetic acid, or S-ethyl trifluorothioacetate. Chemical cleavage of peptide bonds as well is a process known and described in the art (see, for example, Hunt et al. (1986) *Proc. Natl. Acad. Sci.* USA 83:6233-6237; and Tsugita et al. (2001) *Proteomics* 1:1082-1091).

Screening for Candidate Therapeutic Agents

In embodiments, a method of identifying a candidate therapeutic agent comprises contacting a biological sample with a PG probe of general formula I and assaying for the modulation of citrullination of proteins and/or PAD activity in the sample in the presence or absence of the candidate therapeutic agent.

In other embodiments, the candidate therapeutic agent inhibits PAD activity as measured by the citrullination of proteins.

In some embodiments, a pharmaceutical composition comprises a therapeutically effective amount of one or more agents identified by the methods herein, in the treatment of diseases associated with PAD activity.

In other embodiments, a high throughput screening method of identifying a candidate therapeutic agent comprises contacting a support surface comprising a PG probe with a biological sample that have been pre-treated or not pre-treated with a candidate therapeutic agent; assaying for citrullination of the proteins in the biological sample as compared to a baseline control, thereby, identifying a candidate therapeutic agent.

In embodiments, the support surface is any support for conducting assays. For example, if the assay is an immunoassay, the support is a typical multi-well plate. In other cases, the support is a bead to which molecules can be attached. The variations and types of assays are not limited. Thus, the support comprises: plastic, glass, beads, fibers, gels, electrochemical detectors, nanotubes, porous strips, paper, matrices or combinations thereof.

In other embodiments, a pharmaceutical composition comprises an agent in a therapeutically effective amount, identified by any of the methods embodied herein.

Candidate/Test Agents:

Candidate agents include numerous chemical classes, though typically they are organic compounds including small organic compounds, nucleic acids including oligonucleotides, and peptides. Small organic compounds suitably may have e.g. a molecular weight of more than about 40 or 50 yet less than about 2,500. Candidate agents may comprise functional chemical groups that interact with proteins and/or DNA.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced.

Chemical Libraries:

Developments in combinatorial chemistry allow the rapid and economical synthesis of hundreds to thousands of discrete compounds. These compounds are typically arrayed in moderate-sized libraries of small molecules designed for efficient screening. Combinatorial methods, can be used to generate unbiased libraries suitable for the identification of novel compounds. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, *Chem Rev* 96:555-600, 1996; Kenan et al., Exploring molecular diversity with combinatorial shape libraries, *Trends Biochem Sci* 19:57-64, 1994; Janda, Tagged versus untagged libraries: methods for the generation and screening of combinatorial chemical libraries, *Proc Natl Acad Sci* USA. 91:10779-85, 1994; Lebl et al., One-bead-one-structure combinatorial libraries, *Biopolymers* 37:177-98, 1995; Eichler et al., Peptide, peptidomimetic, and organic synthetic combinatorial libraries, *Med Res Rev.* 15:481-96, 1995; Chabala, Solid-phase combinatorial chemistry and novel tagging methods for identifying leads, *Curr Opin Biotechnol.* 6:632-9, 1995; Dolle, Discovery of enzyme inhibitors through combinatorial chemistry, *Mol Divers.* 2:223-36, 1997; Fauchere et al., Peptide and nonpeptide lead discovery using robotically synthesized soluble libraries, *Can J. Physiol Pharmacol.* 75:683-9, 1997; Eichler et al., Generation and utilization of synthetic combinatorial libraries, *Mol Med Today* 1: 174-80, 1995; and Kay et al., Identification of enzyme inhibitors from phage-displayed combinatorial peptide libraries, *Comb Chem High Throughput Screen* 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci. USA*, 90:6909-6913 (1993)); vinylogous polypeptides (Hagihara, et al., *J. Amer. Chem. Soc.* 114:6568 (1992)); nonpeptidal peptidomimetics with β-D-glucose scaffolding (Hirschmann, et al., *J. Amer. Chem. Soc.,* 114:9217-9218 (1992)); analogous organic syntheses of small compound libraries (Chen, et al., *J. Amer. Chem. Soc.,* 116:2661 (1994)); oligocarbamates (Cho, et al., *Science,* 261: 1303 (1993)); and/or peptidyl phosphonates (Campbell, et al., *J. Org. Chem.* 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., *Nature Biotechnology,* 14(3):309-314 (1996) and PCT/US96/10287); carbohydrate libraries (see, e.g., Liang, et al., *Science,* 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569, 588); thiazolidinones and metathiazanones (U.S. Pat. No. 5,549,974); pyrrolidines (U.S. Pat. Nos. 5,525,735 and 5,519, 134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

The screening assays of the invention suitably include and embody, animal models, cell-based systems and non-cell based systems.

In another preferred embodiment, a method of identifying candidate therapeutic agents for treatment of disease, comprises culturing an isolated cell expressing a target molecule, administering a candidate therapeutic agent to the cultured cell; measuring the citrullination of target molecules with the PG probes embodied herein; correlating the target molecules citrullination and/or citrullination profiles in the presence or absence of a candidate therapeutic agent as compared to control cells, wherein a drug is identified based on desirable therapeutic outcomes. For example, a drug which modulates PAD activity and/or citrullination of target proteins, whereby PAD activity is responsible for the disease state, or, the target molecule modulates the activity of another molecule whether upstream or downstream in a pathway.

In another preferred embodiment, a patient's fluid (e.g. blood, plasma, secretions etc.), cell or tissues from a patient are isolated and contacted with a candidate therapeutic molecule. The citrullination of proteins as measured by the PG probes embodied herein, are monitored to identify the PAD activity and/or citrullination profiles affected by the candidate drug.

High-Throughput Screening:

The assays embodied herein are suitable for drug screening in a high throughput screening of agents which modulate the PAD activity as measured by the citrullination of target molecules. In this method, large numbers of different small test compounds are synthesized on a solid substrate. The test compounds are reacted with target molecules, or fragments thereof, and washed. Bound molecules are then detected by the methods embodied herein.

The methods of screening of the invention comprise using screening assays to identify, from a library of diverse molecules, one or more compounds having a desired activity. A "screening assay" is a selective assay designed to identify, isolate, and/or determine the structure of, compounds within a collection that have a preselected activity. By "identifying" it is meant that a compound having a desirable activity is isolated, its chemical structure is determined (including without limitation determining the nucleotide and amino acid sequences of nucleic acids and polypeptides, respectively) the structure of and, additionally or alternatively, purifying compounds having the screened activity). Biochemical and biological assays are designed to test for activity in a broad range of systems ranging from protein-protein interactions, enzyme catalysis, small molecule-protein binding, to cellular functions. Such assays include automated, semi-automated assays and HTS (high throughput screening) assays.

In HTS methods, many discrete compounds are preferably tested in parallel by robotic, automatic or semi-automatic methods so that large numbers of test compounds are screened for a desired activity simultaneously or nearly simultaneously. It is possible to assay and screen up to about 6,000 to 20,000, and even up to about 100,000 to 1,000,000 different compounds a day using the integrated systems of the invention.

Typically in HTS, target molecules are administered or cultured with biological samples, including the appropriate controls.

In one embodiment, screening comprises contacting each biological sample with a diverse library of member compounds, under conditions where complexes between the target and PG probes can form, and identifying which members of the libraries are present in such complexes. In another non limiting modality, screening comprises contacting a target with a diverse library of member compounds, some of which are inhibitors (or activators) of the target, under conditions where a product or a reactant of the reaction produce a detectable signal. In the latter modality, inhibitors of target molecules decrease the signal from a detectable product or increase a signal from a detectable reactant (or vice-versa for activators).

The methods disclosed herein can be used for screening a plurality of test compounds. In certain embodiments, the plurality of test compounds comprises between 1 and 200,000 test compounds, between 1 and 100,000 test compounds, between 1 and 1,000 test compounds, between 1 and 100 test compounds, or between 1 and 10 test compounds. In certain embodiments, the test compounds are provided by compound libraries, whether commercially available or not, using combinatorial chemistry techniques. In certain embodiments, the compound libraries are immobilized on a solid support.

As discussed above, the target can be present in any substrate as the assay parameters can be manipulated or optimized for each type of substrate. For example, if the target is at the surface of or in a cell, or secreted by a cell, the following parameters would be determined: the optimal cell line, cell density, culture medium, serum concentration, final reagents volumes, compound incubation times (for example 12, 24 or 36 hours). If the target is in a cell-free solution, the optimal composition of the solution can be determined as well as the range of concentrations of the positive control standard. In preferred embodiments, the target is in a solution or semi-solid. Other parameters that can be determined are ligand concentrations, temperature of incubation and incubation times of the ligands (for example 1 to 4 hours). The set-up of the reading instrument, for example a time-resolved fluorimeter, is optimized for the measurement window and time delay, excitation parameters (e.g. number of flashes delivered), gain adjustment, and reader head positioning with respect to the receptacle. The proper pharmacological control, if available, needs to be determined.

In another aspect, the present invention provides a method for analyzing citrullination profiles or locations of citrullinated proteins in cells comprising providing an array of locations which contain multiple cells wherein the cells contain one or more PG probes with reporter molecules; scanning multiple cells in each of the locations containing cells to obtain reporter e.g. fluorescent signals from a fluorescent reporter molecule in the cells; converting the signals into digital data; and utilizing the digital data to determine the distribution, environment or activity of the PG probe with a reporter molecule within the cells.

Microarrays:

Microarrays may be prepared, used, and analyzed using methods known in the art (see, e.g., Brennan et al., 1995, U.S. Pat. No. 5,474,796; Schena et al., 1996, *Proc. Natl. Acad. Sci.* U.S.A. 93: 10614-10619; Baldeschweiler et al., 1995, PCT application WO95/251116; Shalon, et al., 1995, PCT application WO95/35505; Heller et al., 1997, *Proc. Natl. Acad. Sci.* U.S.A. 94: 2150-2155; and Heller et al., 1997, U.S. Pat. No. 5,605,662). In other embodiments, a microarray comprises peptides, or other desired molecules which can be assayed to identify a candidate agent.

Kits

In further embodiments, the invention provides kits for use with the methods described above. The kits may comprise, in suitable container means, a phenyl glyoxal probe having a reporter moiety, and reagents for conducting an assay, such as an immunoassay, blot, and the like. In certain embodiments, the PG probe that binds to citrullinated proteins may be bound to a solid support, such as a column matrix or well of a microtiter plate.

The kits may contain PG-labeled probes either in fully linked form, in the form of intermediates, or as separate moieties to be conjugated by the user of the kit. The components of the kits may be packaged either in aqueous media or in lyophilized form.

The container means of the kits may generally include at least one vial, test tube, flask, bottle, syringe or other container means, into which the probes may be placed, and may be suitably aliquoted. Where a second or third component is provided, the kit will also generally contain a second, third or other additional container into which this component may be placed.

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Embodiments of the invention may be practiced without the theoretical aspects presented. Moreover, any theoretical aspects are presented with the understanding that Applicants do not seek to be bound by the theory presented.

Example 1

Figure 2:
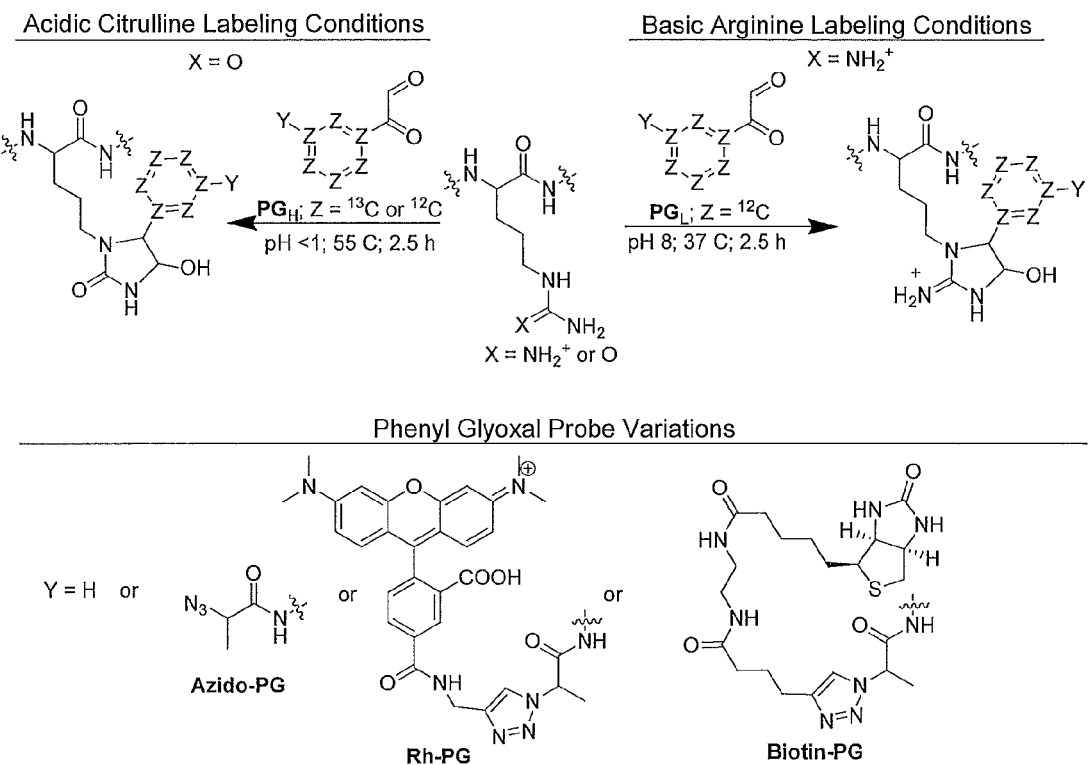
FIG. 2 is a schematic representation showing how arginine and citrulline react with the phenyl glyoxal (PG) probe preferentially at high and low pH, respectively. This technique is modular in that nearly any isotopic, fluorescent, or affinity tagged PG probe can be used. PG tag examples shown include $^{13}C$ as well as rhodamine and biotin. The latter reporter tags, which possess an alkyne group, can be "clicked" to an azide bearing PG probe either before or after the PG is appended to the arginine or citrulline. [(light phenylglyoxal ($PG_L$): Y=H, Z=$^{12}C$) (heavy phenylglyoxal ($PG_H$): Y=H, Z=$^{13}C$) (rhodamine phenylglyoxal (Rh-PG): Y=rhodamine, Z=$^{12}C$) (biotin phenylglyoxal: (biotin-PG): Y=biotin; Z=$^{12}C$)].
Figure 11A:
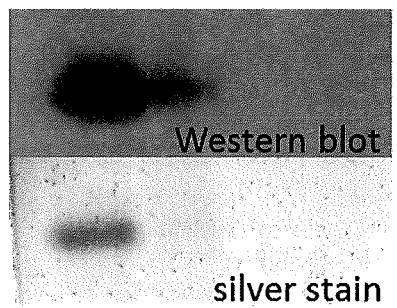
FIG. 11A shows a gel-based assay to compare the sensitivity of the Biotin-PG probe (top) to silver staining (bottom) with respect to deiminated histone H3.
Figure 11B:
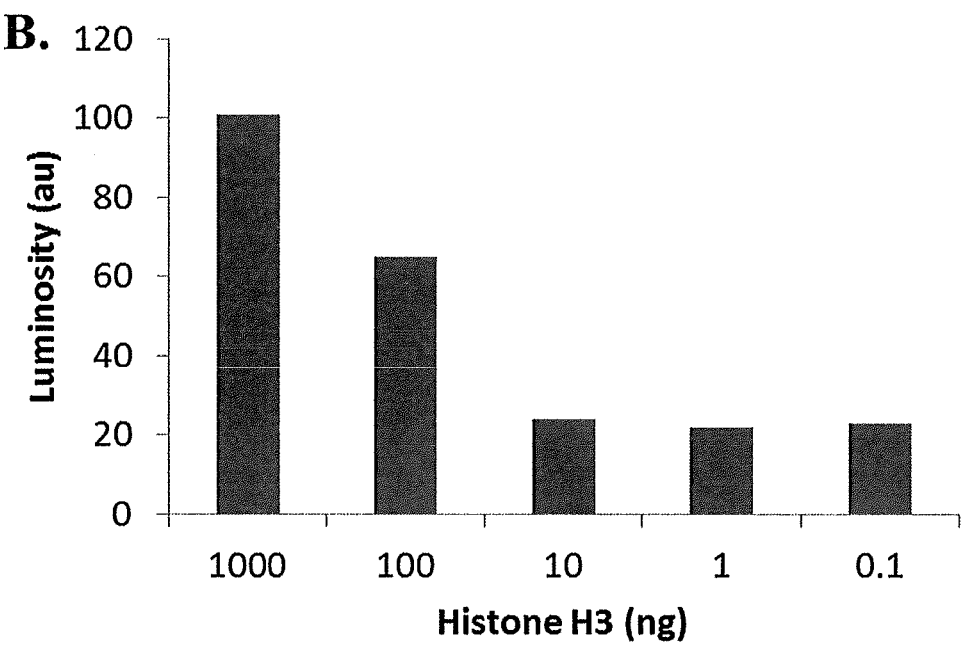
FIG. 11B: Quantitation of the data indicates that the limit of detection for citrulline by the Biotin-PG probe is 100 ng of deiminated histone H3.

The Design, Synthesis, and Method Development of Novel Phenyl Glyoxal Probes: Tools for the Investigation of Cellular Citrullination Design of Phenylglyoxal Probe The design of the citrulline specific probes described herein is based on the chemoselective reaction that occurs between glyoxals and either citrulline or arginine under acidic or basic conditions, respectively (FIG. 2; FIGS. 11A, 11B) (Tutturen, A. E. V., et al. (2010), *Anal. Biochem.* 403, 43-51). Given this well established chemistry, work began for the development of phenylglyoxal (PG) probes derivatized with fluorescent and biotin reporter tags (FIG. 2). A $^{13}$C-tagged heavy PG probe (PG$_H$) (FIG. 2) was also synthesized to aid the identification of citrullinated residues in standard and quantitative mass spectrometry/proteomics experiments. Though the probes shown each serve a specific purpose (Table 1), it should be understood that any type of functionalized tag can be readily appended to the PG moiety.

TABLE 1

Phenylglyoxal probe utilities that have been validated within the scope of this disclosure, as well as potential uses.

| Probe | Validated Uses | Potential Uses |
| --- | --- | --- |
| Isotope ($PG_L$, $PG_H$) | Monitoring peptide or small molecule citrullination. | Site of modification identification; Quantitative proteomics. |
| Rhodamine-PG | Identification of citrullinated proteins by SDS-PAGE. | Immunohistochemistry; Tissue or serum classification based on citrullination. |
| Biotin-PG | Isolating and enriching citrullinated proteins from complex matrices. | Isolation and differential proteomics for the identification of citrullinated proteins. |

The utility of the isotopically labeled probe, $PG_H$, comes from the fact that protein citrullination only results in a 0.98 Da mass increase, which is difficult to differentiate from $^{13}C$-isotopes; here the mass increase is 0.992 Da. Additionally, this mass change is indistinguishable from that obtained after the hydrolysis of the side chain amides present in Asn and Gln. In contrast, with $PG_L$ and $PG_H$ the mass increase is 116.1 Da and 122.1 Da, respectively, which are readily detectable. Furthermore, comparison of samples differentially labeled with $PG_L$ and $PG_H$ enables the quantitative determination of the extent of protein citrullination.

The utility of the fluorescent and biotin-tagged probes comes from the fact that they can be used to identify citrullinated proteins under a variety of circumstances (see Table 1). For their synthesis, initially considered was a route similar to the one described by Fleckenstein et al., (*Analytical Biochemistry* 403, 43-51 (2010)) where the PG moiety is derivatized to a solid phase resin via the para position. However, this chemistry was not amenable to solution phase chemistry (see below), so the focus was on synthesizing compounds where the phenylgloxal was linked to the reporter tag via the meta position. To simplify the chemistry (see below) and permit functionalization to reporter tags before or after reaction with either citrulline or arginine, we focused on synthesizing azide bearing PG probes that can be "clicked" to an alkyne bearing reporter tag using the copper catalyzed azide-alkyne cycloaddition reaction (Rostovtsev, V. V., et al. (2002), *Angew Chem Int Ed Engl* 41, 2596-2599; Tornoe, C. W., et al. (2002), *J Org Chem* 67, 3057-3064).

Synthesis of Heavy Phenylglyoxal ($PG_H$) Probe

The synthesis of heavy phenylglyoxal ($PG_H$; Scheme 1A) was completed by oxidizing commercially available $^{13}C_6$-acetophenone (1) with $SeO_2$ in dioxane/$H_2O$ (4:1). The reaction was heated to reflux under $N_2$ atmosphere for 16 h filtered through a plug of celite/$SiO_2$ and purified by reverse phase HPLC using $H_2O$/ACN plus 0.05% TFA as the eluent to give the title product in 50% yield.

Scheme 1:

A.

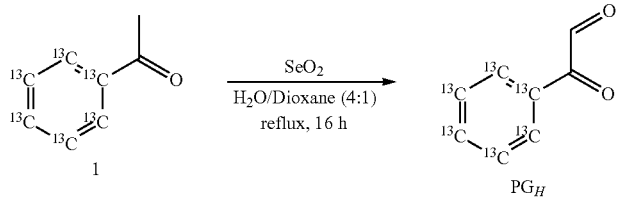

B.

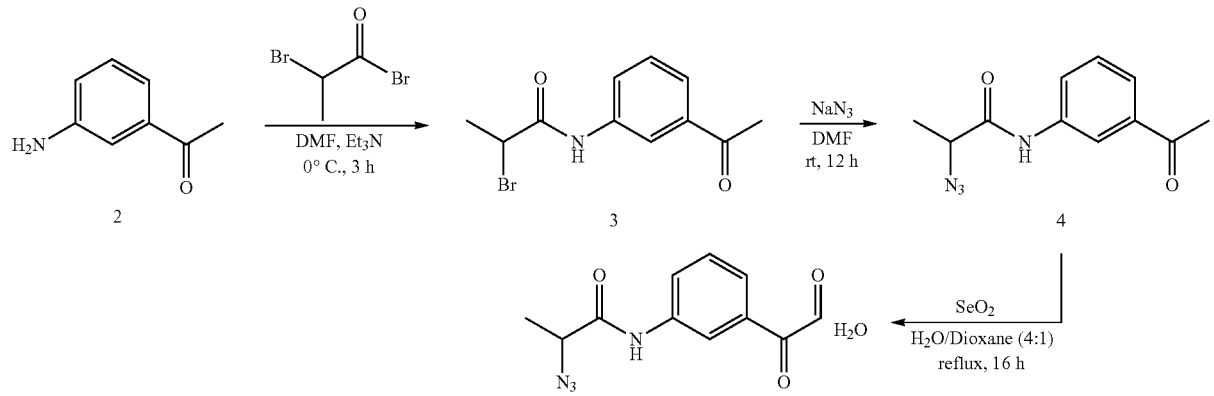

C.
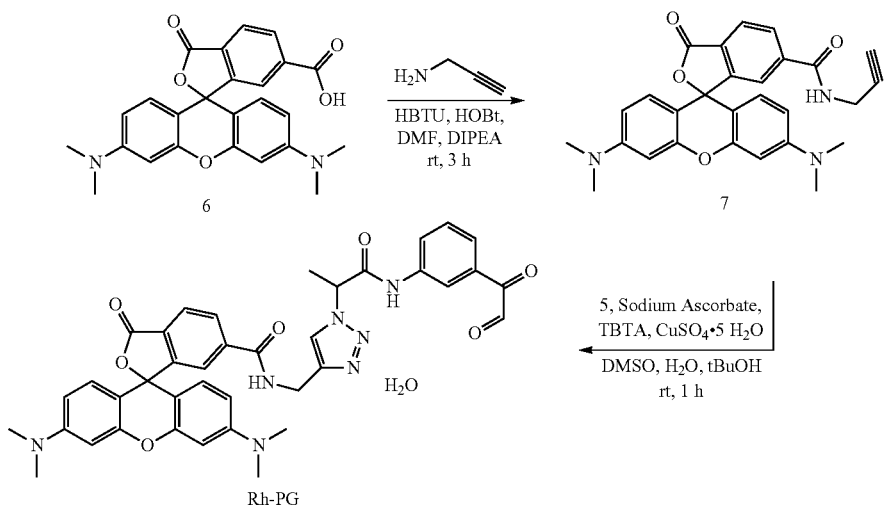
D.
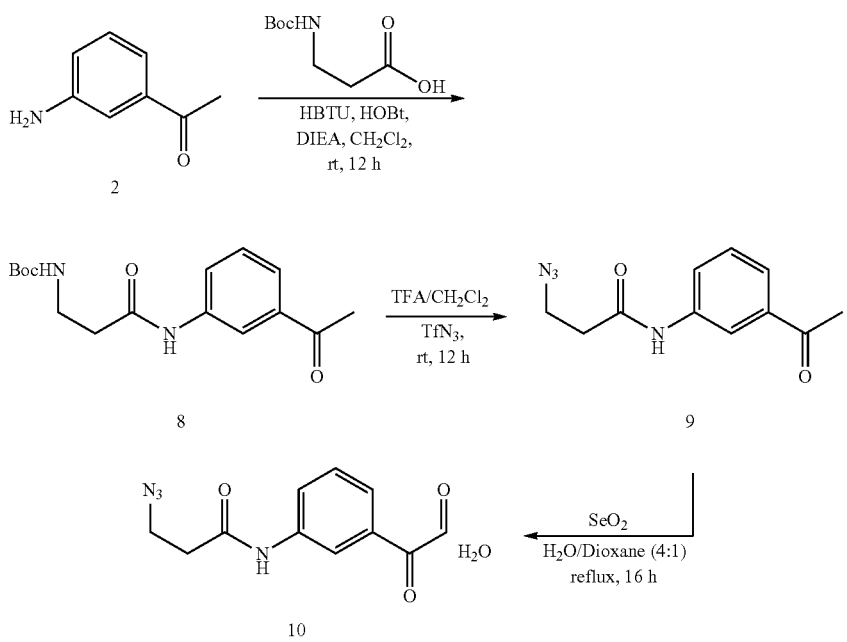
E.
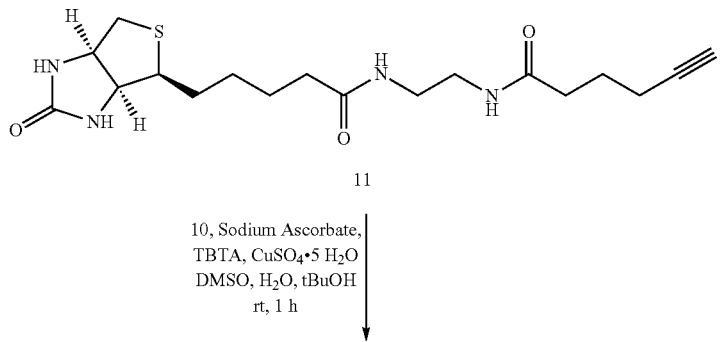

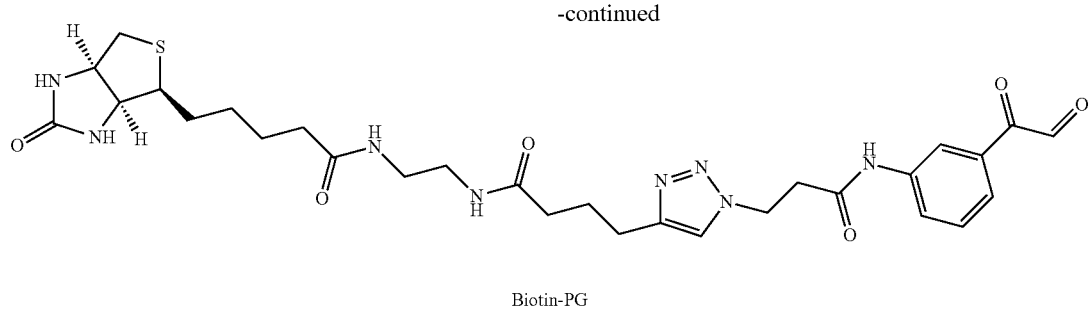

Biotin-PG

Scheme 1 shows the synthesis of phenylglyoxal probes.

Synthesis of Rhodamine and Biotin-Tagged Phenylglyoxal Probes (Rh-RG and Biotin-PG)

The synthesis of an alkyne derivatized PG probe was initially approached as described in the literature, starting with 4-hydroxy-phenylglyoxal (HPGA) (Tutturen, A. E. V., et al. (2010) *Analytical Biochemistry* 403, 43-51). However, when 4-hydroxy phenylglyoxal was treated with propargyl bromide under basic conditions no alkyne product was observed. A variety of bases and/or solvents screened in this step offered little or no help (Scheme 2A). Therefore, 4-hydroxy-acetophenone was initially converted to the corresponding propargyl acetophenone by treatment with propargyl bromide and potassium carbonate in dry DMF. However, refluxing the propynyloxy acetophenone with $SeO_2$ resulted in complete decomposition of the starting material (Scheme 2B). In a similar fashion the commercially available 4-ethynyl acetophenone underwent complete decomposition under the same $SeO_2$ reaction conditions (Scheme 2C).

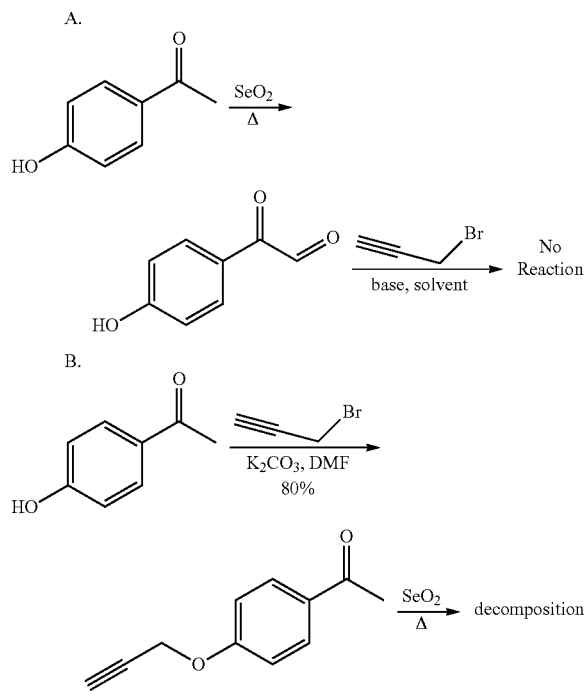

Scheme 2

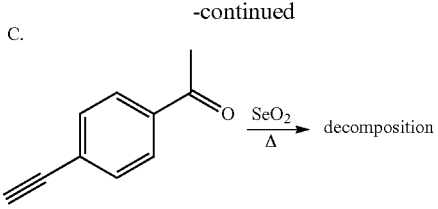

Several attempts were made to synthesize alkyne-containing PG probes linked to reporter tags via the para position, however, none of these synthetic routes resulted in the desired compounds.

The lack of reactivity and/or decomposition of the 4-hydroxy derivatives is likely due to conjugation between the 4-hydroxy and 1-ketone moieties, as well as the relative thermodynamic instability of alkyne groups. The inability to synthesize para alkyne bearing PGs prompted the reinvestigation of the synthetic strategy and to identify a more amenable route to the desired PG probes. It was hypothesized that azido acetophenones would serve as suitable replacements for alkyne substituted acetophenones since azido groups are more stable than alkynes under most conditions and could be employed in cycloaddition chemistry to give the desired PG probes. Commercially available 3-amino-acetophenone was selected as a starting material because the amine is readily converted to an azido group.

Synthesis of the azido-PG precursors (5 and 9) to be clicked to rhodamine-alkyne (7) and biotin-alkyne (11) began with commercially available 3-amino acetophenone (Scheme 1). To begin, 3-amino acetophenone (2) was dissolved in DMF with triethylamine ($Et_3N$) at 0° C. 2-bromopropionyl bromide was then slowly added (Scheme 1B). The reaction was stirred at room temperature under $N_2$ atmosphere for 3 h and then diluted with water. The pale brown precipitate was filtered and dried to give the product (3) in 80% yield. The compound was dissolved in DMF and $NaN_3$ added to initiate the reaction. The reaction was stirred at room temperature under $N_2$ atmosphere for 12 h, and then diluted with water. The precipitated solid was filtered and dried to give the product (4) in 50% yield. Compound 8 was obtained by coupling 3-amino acetophenone with Boc-β-alanine under standard amide forming conditions. The Boc group was cleaved with TFA and subsequent azido transfer gave the azido acetophenone (9) in 60% yield. These compounds (4 and 9) were subsequently refluxed in dioxane/$H_2O$ (4:1) under $N_2$ with $SeO_2$ for 24 h. The reaction mixture was filtered through a $SiO_2$/celite plug, concentrated and purified by reverse phase HPLC, using a linear gradient of $H_2O$/ACN plus 0.05% TFA to give the product (5 or 10) in 40% yield. Note that the reporter, tags and PG moieties could be linked through a variety of linkers and are not limited to the two linkers described above.

Synthesis of rhodamine-alkyne (7) was completed from 5(6)-carboxytetramethyl rhodamine (6) in DMF with DIPEA, propargyl amine, HBTU, and HOBt (Scheme 1C). The reaction was stirred at room temperature under $N_2$ atmosphere for 3 h and diluted with $H_2O$/ACN (3:2) and purified by reverse phase HPLC to give the product (7) in 84% yield. To a stirred solution of rhodamine-alkyne (7) was added azido-PG (5) in DMSO/$H_2O$ (1:1). Subsequently, sodium ascorbate in $H_2O$ and TBTA in DMSO/$H_2O$/$^t$BuOH (3:1:1) were added. $CuSO_4.5H_2O$ was then added and the reaction stirred at rt for 1 h, before diluting with ACN/$H_2O$ (2:1, with 0.05% TFA). The product was purified by reverse phase HPLC to give the rhodamine-PG probe (Rh-PG; Scheme 1C) in 90% yield.

Synthesis of the biotin-PG probe (Biotin-PG; Scheme 1E) began from alkyne functionalized biotin (11), which was synthesized previously (Jones, J. E., et al. (2011), *ACS Chemical Biology* 7, 160-165). To a stirred solution of alkyne functionalized biotin (11) was added azido PG (10) in DMSO/$H_2O$ (1:1). Subsequently, sodium ascorbate in $H_2O$ and TBTA in DMSO/$H_2O$/$^t$BuOH (3:1:1) were added, followed by $CuSO_4.5H_2O$. The reaction was stirred at room temperature for 1 h, diluted with ACN/$H_2O$ (2:1 plus 0.05% TFA), and purified by reverse phase HPLC to give the biotin-PG in 50% yield.

MALDI spectra of H4-13 (Ac-SGRGKGGKGLGKG-NH2; SEQ ID NO: 1) and H4-13-Cit (Ac-SGCitGKG-GKGLGKG-NH2; SEQ ID NO: 2) labeled under basic or acid conditions with PGL at 37° C. 3 h, indicate that arginine is specifically labeled under basic conditions and citrulline is specifically labeled under acidic conditions.

LC-MS analysis of PG isotopically labeled H4-13 peptide incubated with PAD4 for various times (i.e., 0, 5, 15, and 30 min), three m/z peaks were observed for the H4-13 Arg peptide (Ac-SGRGKGGKGLGKG-NH2; SEQ ID NO: 1) labeled with $PG_L$ (i.e., 330 (+4), 439 (+3), and 659 (+2)) and only two were observed for H4-13-Cit peptide (Ac-SGCit-GKGGKGLGKG-NH2; SEQ ID NO: 2) labeled with $PG_H$ (i.e., 442 (+3) and 662 (+2)). Three spectra are provided for each time point, highlighting the [M+2], [M+3], and [M+4] peaks. The relative ratio of these peaks is then used to determine the percent citrullination of the given peptide at any one time point.

Labeling of Citrullinated Peptides with $PG_H$

Figures 3A, 3B:
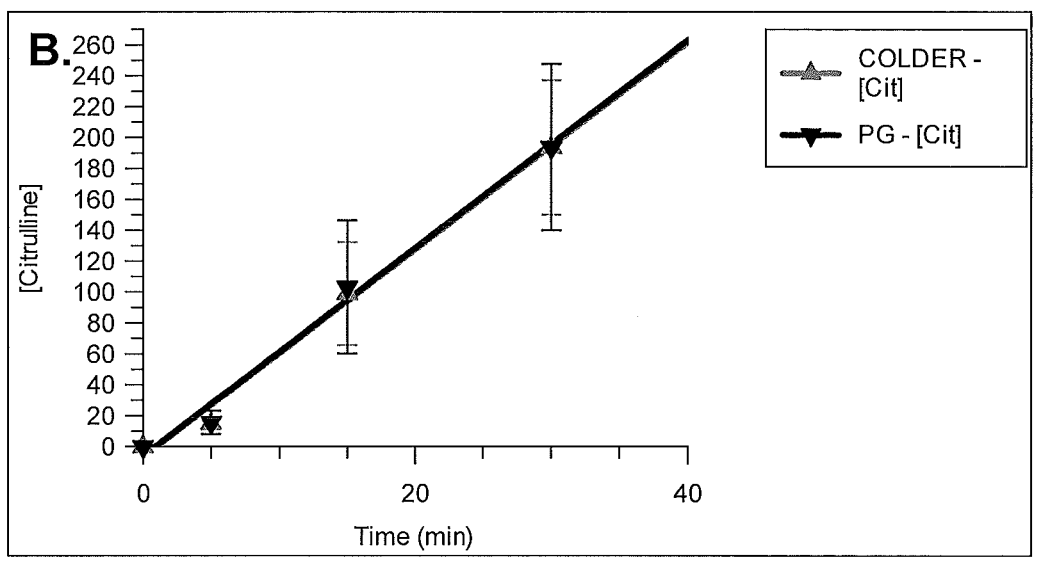
FIG. 3A shows the sequence of the PAD4 substrate H4-13 peptide (SEQ ID NO: 1).
FIG. 3B shows the comparison of the traditional COLDER analysis with PG analysis indicating that PG labeling followed by LC-MS is a viable way to determine the rate and degree of citrullination.

The utility of the isotopically-labelled PG probe, $PG_H$, in determining the degree of peptide citrullination, was demonstrated. Initially, the H4-13 peptide was tested (FIG. 3A). The sequence of this peptide is based on the N-terminus of histone H4 and contains a single arginine residue, as well as several other potential nucleophiles. For these studies, PAD4 (0.2 μM) was incubated with the H4-13 peptide in reaction buffer (50 mM HEPES, 50 mM NaCl, 10 mM $CaCl_2$, and 2 mM DTT) at 37° C. At various times (t=0, 5, 10, 15, and 30 min) a 50 μL aliquot was removed and quenched by flash freezing in $N_{2(l)}$. At the same time, a 100 μL aliquot was removed and quenched with 50 mM EDTA. The 50 μL aliquot was analyzed by traditional COLDER analysis (Kearney, P. L., et al. (2005), *Biochemistry* 44, 10570-10582; Knipp, M., and Vasak, M. (2000), *Anal. Biochem.* 286, 257-264) and the 100 μL aliquot was divided into two equal parts. To one half was added light PG (2 mM; $PG_L$; FIG. 2) and to the other half, 20% trichloroacetic acid (TCA) and $PG_H$ (2 mM)). Both samples were incubated at 37° C. for 3 h and then recombined and analyzed by LC-MS. The percent citrullination was calculated by dividing the peak height of $PG_H$ labeled citrulline containing peptide by the sum of $PG_L$ and $PG_H$ labeled peptides. Comparison of this method of analysis with the traditional COLDER analysis (FIG. 3B) indicates that both methods can detect the levels of citrullinated peptides equally well. Thus, these PG probes can be used to quantify the citrullination of a specific residue by MS, which will undoubtedly be useful for quantitative proteomics.

Labeling of Citrullinated Proteins with Rh-PG

Figure 4:
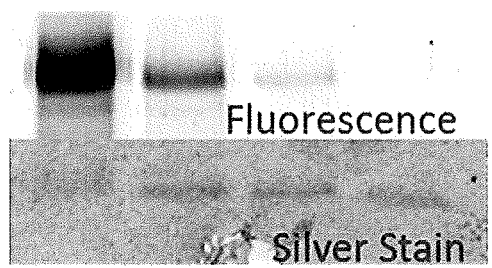
FIG. 4 shows that Rh-PG labels citrullinated PAD4 in a concentration dependent fashion.

Having shown that PG probes were capable of selectively reacting with either arginine or citrulline in a pH dependent manner, the next step taken was to demonstrate the utility of the rhodamine functionalized PG probe, Rh-PG (FIG. 2), in labeling citrulline containing proteins. To demonstrate the utility of the Rh-PG probe as a proteomic tool, the ideal probe concentration, probe sensitivity/limit of detection (LOD), and ideal labeling time were identified. To determine the ideal probe concentration, PAD4 was completely autodeiminated in reaction buffer at 37° C. for 1 h; the reaction was then quenched with 50 mM EDTA. Autodeiminated PAD4 (30 μL, 0.2 μM or 0.45 μg) was mixed with TCA (20% final, 6.0 μL) and various concentrations of Rh-PG (100, 10, 1, or 0.1 μM Rh-PG). Samples were incubated at 37° C. for 3 h. Note that incubations at higher temperatures led to the formation of SDS insoluble aggregates that could not be separated by SDS-PAGE. After the 3 h incubation, the acidic solutions were cooled on ice for 30 min to complete the TCA precipitation, and proteins isolated by centrifugation at 14,000 rpm for 15 min at 4° C. The supernatant was removed and samples were washed with cold acetone and dried at 100° C. for 5 min Proteins were resuspended in 25 μL of 50 mM HEPES. All samples were then boiled with 6×SDS loading dye and analyzed by gel electrophoresis (170 V; 50 min) and fluorescent imaging on a Typhoon Imager (Ex. 532 nm; Em. 580 nm) (FIG. 4). The Rh-PG probe labels citrullinated PAD4 in a concentration dependent fashion. Fluorescent bands were clearly visible down to 1 μM probe, and given that the band at 100 μM probe is strong, yet not saturated, this was the concentration of probe used in subsequent Rh-PG labeling experiments.

Figure 5A:
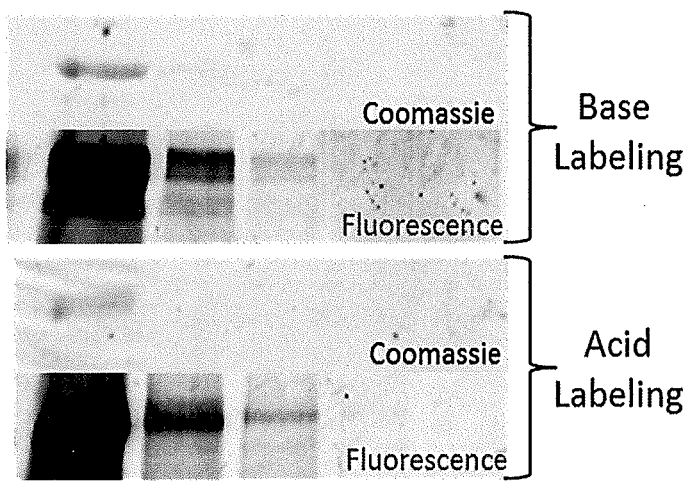
FIGS. 5A and 5B show that Rh-PG was used to label autodeiminated PAD4 under both acidic and basic labeling conditions.
Figure 5B:
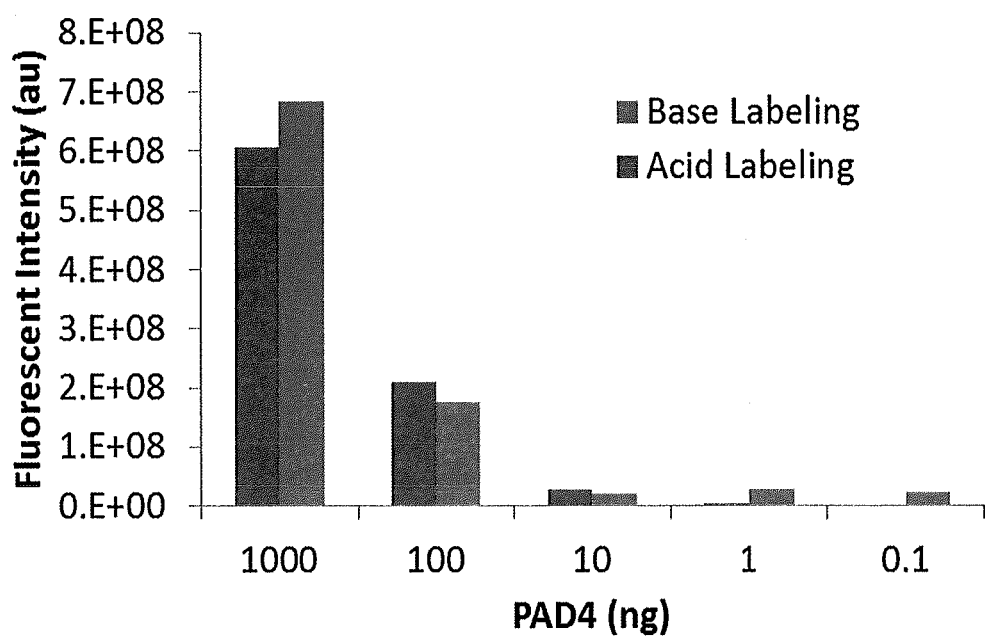

The sensitivity of the probe was analyzed next (FIGS. 5A, 5B). Autodeiminated PAD4, prepared as described above, was diluted into 50 mM HEPES pH 8.0 to final concentrations of 1.6 μM, 0.16 μM, 16 nM, 1.6 nM, and 0.16 nM. To one set of samples was added 0.1 mM Rh-PG, and to a second set, 20% TCA and 0.1 mM Rh-PG. The samples were then incubated at 37° C. for 3 h. To TCA precipitate autodeiminated PAD4, the acidic solutions were cooled on ice for 30 min and then centrifuged at 14,000 rpm for 15 min at 4° C. The supernatant was removed and samples were washed with cold acetone and dried at 100° C. for 5 min. Proteins were resuspended in 25 μL of 50 mM HEPES. Both basic and acidic samples were then boiled with 6×SDS loading dye and various amounts of protein (i.e., 1000, 100, 10, 1, and 0.1 ng) loaded onto a 12% SDS-PAGE gel. Gel electrophoresis was performed at 170 V for 60 min and the gels analyzed on a Typhoon Imager (Ex. 532 nm; Em. 580 nm) (FIGS. 5A, 5B). Fluorescent bands could be clearly seen at 10 ng of protein for both base and acid labeled samples, and a faint band was visible for 1 ng of protein under the acid labeling conditions. Defining the limit of detection (LOD) as three times the noise gave an LOD of 1 ng for the Rh-PG probe labeling of autodeiminated PAD4, making this probe significantly more sensitive than traditional coomassie staining. Note that the sensitivity of the probe under the acidic labeling conditions depends on the extent of citrullination and may vary from protein to protein.

Figure 6:
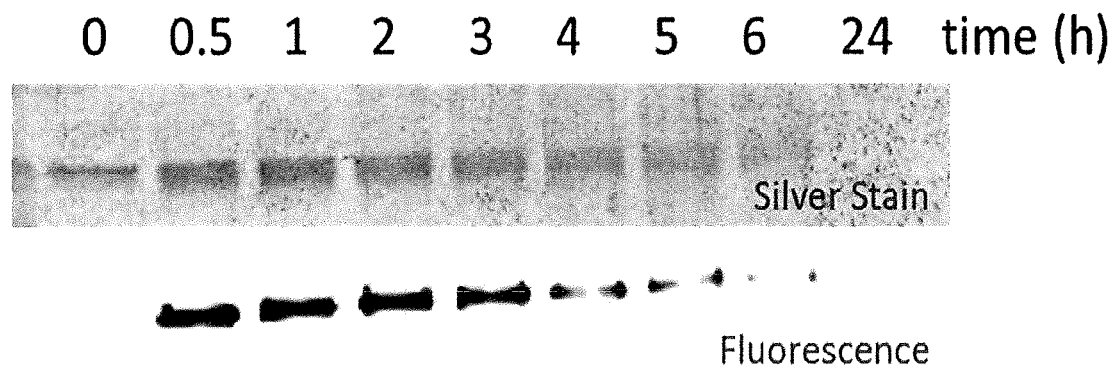
FIG. 6 is a gel showing the Rh-PG labeling time course. Protein loading levels decrease as a function of time, thereby accounting for the decreased fluorescence intensity at times≥3 h. The top panel is the silver stained gel and the bottom panel is the fluorescent image.

Having identified the optimal probe concentration (i.e., 100 μM) and protein loading amount (i.e., 100 ng; 1.33 picomoles), the next step taken was to determine the time dependence of protein labeling with the Rh-PG probe (FIG. 6). Autodeiminated PAD4, prepared as above, was incubated with 20% TCA and 100 μM Rh-PG, and 30 μL aliquots removed at various times (i.e., 0, 0.5, 1, 2, 3, 4, 5, 6, and 24 h). The labeling reactions were quenched with 100 mM citrulline for 30 min. To precipitate the proteins, the samples were then cooled on ice for 30 min, and centrifuged at 14,000 rpm for 15 min at 4° C. The supernatant was removed and samples were washed with cold acetone and dried at 100° C. for 5 min. Samples were stored at −20° C. until analyzed. Proteins were resuspended in 25 μL of 50 mM HEPES, boiled with 6×SDS loading dye and analyzed by gel electrophoresis (170 V; 50 min) and imaged on a Typhoon Imager (Ex. 532 nm; Em. 580 nm) (FIG. 6). Interestingly, although there was a significant increase in fluorescent intensity after 0.5 h, little increase was seen beyond this time point. However, silver staining indicated that protein loading was decreasing as a function of labeling time, presumably due to the formation of insoluble protein precipitates. In fact, no protein was observed in the gel after 24 h of labeling, either by silver staining or Rh-PG labeling. Given that fluorescent intensity and protein loading appeared to fall off after 3 h, this time appeared to be optimal for Rh-PG labeling.

Figures 7A, 7B:
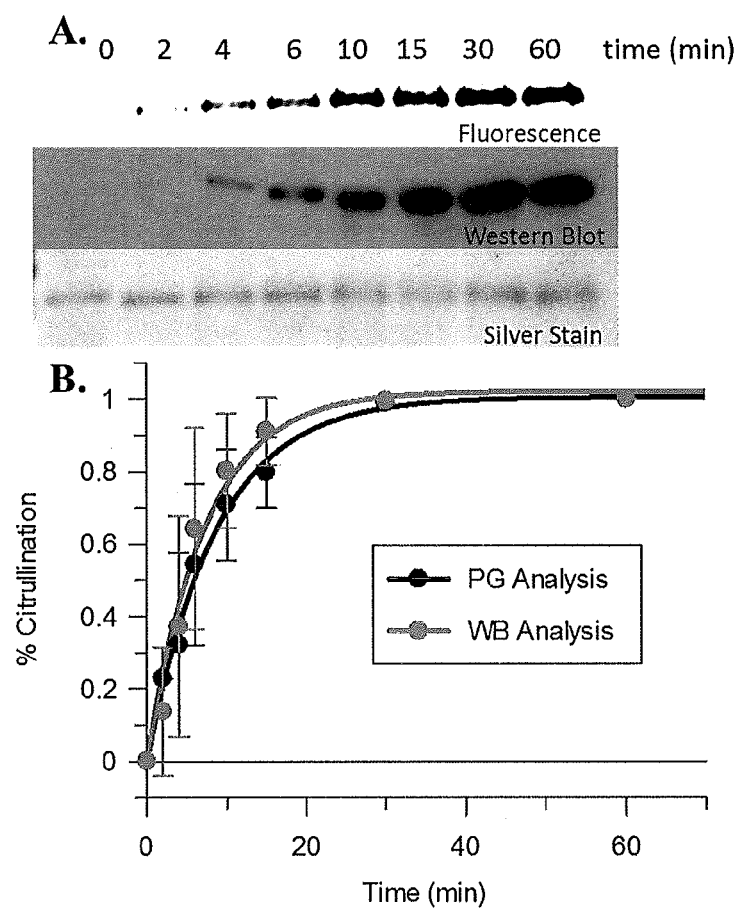
FIG. 7A shows the time course for the autodeimination of PAD4 monitored by either Rh-PG labeling (upper) or the Anti-Citrulline (Modified) Detection Kit (middle). Silver staining (lower) indicates equal protein loading.
FIG. 7B shows the quantitation of the data which indicate that the two methods provide similar rates of PAD4 autodeimination.

Next the Rh-PG anti-citrulline detection method was compared with the Anti-Citrulline (Modified) Detection Kit (Millipore; Billerica, Mass.) in determining the rate of PAD4 autodeimination (FIGS. 7A, 7B). For these experiments, PAD4 (0.2 μM) was incubated in reaction buffer at 37° C. and 50 μL aliquots were removed and quenched with 50 mM EDTA at various times (i.e., 0, 2, 4, 6, 10, 15, 30, and 60 min). Each aliquot was then divided to give two replicates of the time series. One replicate was incubated at 37° C. for 3 h in 20% TCA with 0.1 mM Rh-PG. Solutions were cooled on ice for 30 min to complete the TCA precipitation, followed by centrifugation at 14,000 rpm for 15 min at 4° C. The supernatant was removed and samples were washed with cold acetone and dried at 100° C. for 5 min. Proteins were resuspended in 25 μL of 50 mM HEPES, boiled with 6×SDS loading dye, and analyzed by gel electrophoresis (170 V for 60 min) and fluorescent imaging (Ex. 532 nm; Em. 580 nm) (FIG. 7A).

The other time series replicates were separated by gel electrophoresis and electrotransferred to polyvinylidene difluoride (PVDF; tris-glycine buffer; 80 V; 70 min) Autodeiminated PAD4 was then detected using the Anti-Citrulline (Modified) Detection Kit (FIG. 7A). For this analysis, the PVDF membrane was washed with water twice. Citrulline modification solution was then prepared by combining 5 mL of Reagent A (0.025% $FeCl_3$ in water/98% $H_2SO_4$/85% $H_3PO_4$ (55%/25%/20%); prepared in house) with 5 mL of Reagent B (0.5% 2,3-butanedione monoxime, 0.25% antipyrine, and 0.5 M acetic acid; provided). This solution was added to the blot and incubated without agitation overnight at 37° C. The blot was then washed with water (5×5 min) and blocked with 5% milk in TBST for 1 h at rt with constant agitation. After blocking, the blot was incubated with the primary anti-citrulline (modified) antibody at a dilution of 1:1000 in 5% milk in TBST for 1 h at rt. This solution was removed and the blot washed with TBST (3×5 min). The blot was then incubated with HRP conjugated goat anti-rabbit IgG at a dilution of 1:4000 in 5% milk in TBST for 1 h at rt. After washing the blot with TBST (5×5 min) citrullinated proteins were visualized by enhanced chemoluminescence (ECL). These experiments were performed in duplicate. Quantification of fluorescent images was done using ImageQuant 5.2 and Western blots were analyzed with Adobe Photoshop 7.0. Plots of the data (FIG. 7B) show that both the Rh-PG labeling and Anti-Citrulline (Modified) Kit give similar data for the rate of autodeimination of PAD4, indicating that this method of detecting peptidyl-citrulline was comparable to the commercially available Anti-Citrulline (Modified) Detection Kit. Note that compared to this kit, the Rh-PG labeling method took significantly less time (~5 h versus ≥25 h), required fewer steps (6 versus 12), and simpler analysis (fluorescent imaging versus Western blotting).

Biotin-PG Pulldown and Labeling

Figure 8A:
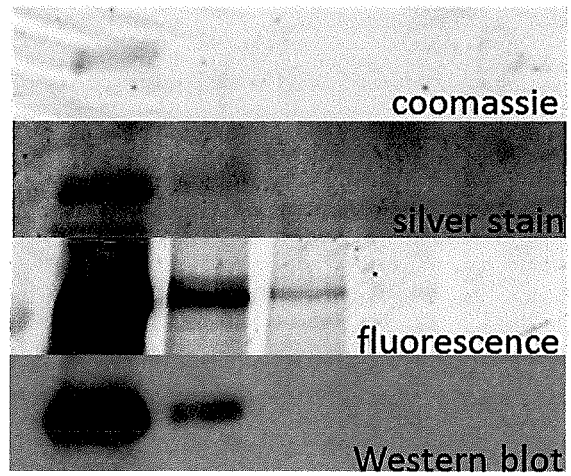
FIG. 8A shows a gel-based assay which compares the sensitivities of the Rh-PG (lower middle) and Biotin-PG (bottom) probes to coomassie (top) and silver staining (upper middle).
Figure 8B:
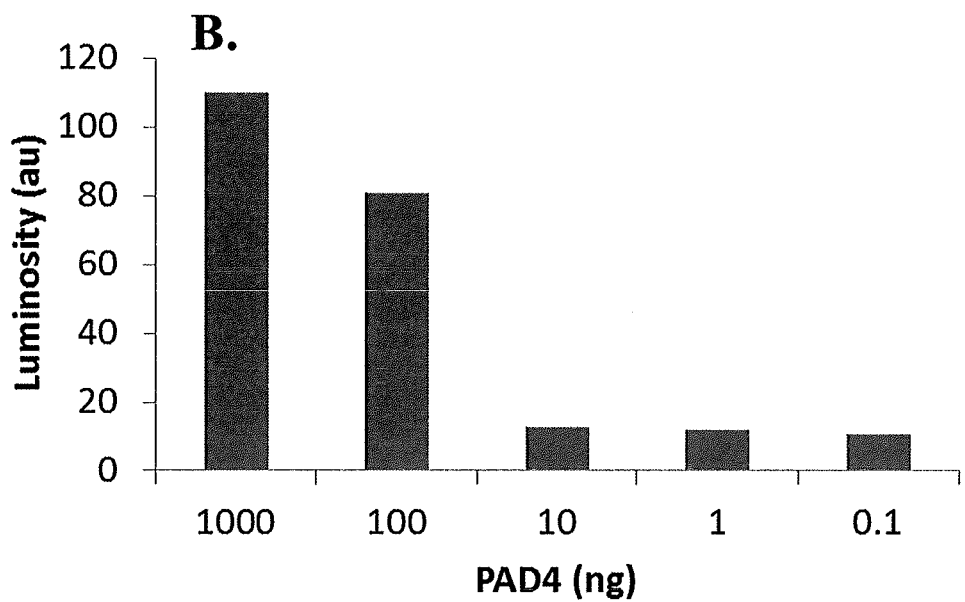
FIG. 8B: Quantitation of the data indicates that the limit of detection for citrulline by the Biotin-PG probe is 100 ng of autodeiminated PAD4.

It was next set out to determine the utility of the biotin-tagged PG probe, Biotin-PG (FIG. 2), as a tool for labeling, isolating, and enriching citrullinated proteins. As with the Rh-PG probe, the LOD of this probe was first determined with respect to autodeiminated PAD4. For these studies, autodeiminated PAD4, prepared as described above, was diluted into 50 mM HEPES pH 8.0 to final concentrations of 1.6 μM, 0.16 μM, 16 nM, 1.6 nM, and 0.16 nM. These samples were then incubated at 37° C. for 3 h with 20% TCA and 0.1 mM Biotin-PG. Solutions were quenched, cooled on ice for 30 min, and centrifuged at 14,000 rpm for 15 min at 4° C. The supernatant was removed and samples were washed with cold acetone and dried at 100° C. for 5 min Proteins were resuspended in 25 μL of 50 mM HEPES and boiled with 6×SDS loading dye and various amounts of protein (i.e., 1,000, 100, 10, 1, and 0.1 ng) loaded onto a 12% SDS-PAGE gel. Gel electrophoresis was performed at 200 V for 50 min and proteins were subsequently electrotransferred to nitrocellulose (tris-glycine buffer; 80 V; 70 min) and the membrane blocked with 5% BSA in PBS for 1 h at rt. After washing 2× with PBS (10 min), the blot was treated with streptavidin-HRP (1:20, 000) in 5% BSA in PBS for 1 h at rt. The blot was then washed 3× with PBS (10 min) and 1× with water (5 min) before visualizing with ECL (FIGS. 8A, 8B). The LOD for the Biotin-PG probe is 100 ng of autodeiminated PAD4.

Figure 9:
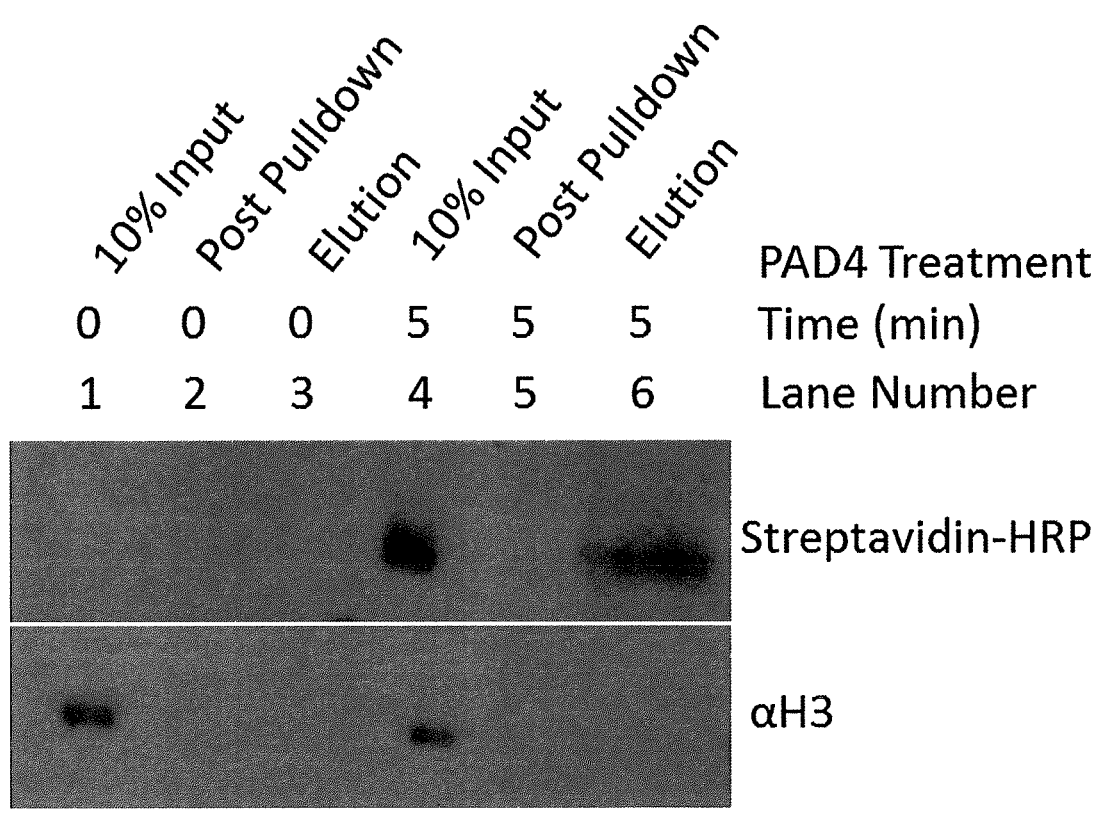
FIG. 9 shows the biotin-PG labeling and isolation of PAD4 deiminated histone H3.

Having determined the LOD of the biotin-PG probe, the utility of this probe was demonstrated in pulling down and isolated citrullinated proteins. For these studies, recombinant bacterially expressed histone H3 was used, because this protein is efficiently modified by PAD4, but is not citrullinated (or subject to autodeimination) during expression in *Escherichia coli*, thereby providing an excellent proof-of-concept for the isolation of novel PAD substrates. Note that the LOD for the Biotin-PG probe with H3 was similar to the LOD for autodeiminated PAD4 (FIGS. 11A, 11B). Initially, histone H3 (5 μM), a known substrate of PAD4, was treated with PAD4 (0.2 μM) in reaction buffer at 37° C. for 0 or 5 min. These samples were then incubated at 37° C. for 3 h with 20% TCA and 0.1 mM biotin-PG. Biotin-PG was quenched with 100 mM citrulline for 30 min and solutions were cooled on ice for 30 min to complete the TCA precipitation, followed by centrifugation at 14,000 rpm for 15 min at 4° C. The supernatant was removed and samples were washed with cold acetone and dried at 100° C. for 5 min. Proteins were resuspended in 70 μL of 1% SDS in PBS and denatured at 95° C. for 5 min, at which point a 30 μL aliquot was removed to serve as a pre-pulldown control. A second 30 μL aliquot was then added to 50 μL of High Capacity Streptavidin Agarose Resin (Thermo Scientific) equilibrated in PBS and rocked at room temperature for 30 min. The supernatant was removed and 30 μL set aside as a post-pulldown control. The resin was then washed 1× with 0.2% SDS in PBS (10 min) and 3× with PBS (1 min). Isolated proteins were eluted from the resin in elution buffer (1% SDS, 150 mM biotin, 100 mM thiourea, 3 M urea) at 42° C. for 30 min, followed by 30 min at 95° C. The supernatant was collected and the resin washed 3× with water. These fractions were combined and dried using a SpeedVac evaporator. Samples were resuspended in PBS, boiled with 6×SDS loading dye, and separated by gel electrophoresis (210 V for 45 min). Proteins were then electrotransferred to nitrocellulose (tris-glycine buffer; 80 V; 70 min) and the blot blocked with 5% BSA in PBS for 1 h at rt. After washing 2× with PBS (10 min), the blot was treated with streptavidin-HRP (1:5000) in 5% BSA in PBS for 1 h at rt. The blot was then washed 3× with PBS (10 min) and 1× with water (5 min) before visualizing by ECL (FIG. 9). To confirm equal loading amounts of histone H3 at both time 0 and 5 min, this same blot was probed with an anti-histone H3 antibody. Briefly, the blot was treated 2× with acidic stripping buffer (0.2 M glycine, 10 mM Tween-20, 0.1% SDS, pH 2.2) (10 min), washed 2× with PBS (10 min), and 2× with TBST (5 min) The blot was subsequently blocked with 5% milk in TBST for 1 h at room temperature and treated with anti-histone H3 polyclonal antibody (1:5000; catalogue #ab1791, Abcam, Cambridge, Mass.) in 2.5% milk in TBST for 1 h at room temperature. After washing 3× with TBST (5 min), the blot was treated with goat anti-rabbit (HRP) secondary antibody (1:10,000) in 2.5% milk in TBST for 1 h at room temperature. The blot was then washed 3× with TBST (5 min) and visualized by ECL (FIG. 9). These data indicated that the biotin-PG probe selectively bound to peptidyl-citrulline moieties on histone H3 deiminated by PAD4 for 5 min but not 0 min. The anti-H3 blot indicated that equal amounts of histone were loaded in lanes 1 and 4, yet only deiminated H3 was apparent in the streptavidin-HRP blot, indicating that this probe was selectively binding to citrulline. Most importantly, a significant, although not quantitative band was observed for citrullinated H3 in the elution from the streptavidin-agarose resin (lane 6), meaning that citrullinated proteins could be isolated and enriched. Interesting to note was that the eluted H3 was not recognized by the H3 antibody, perhaps due to modification by the Biotin-PG probe or some other modification that occurred during pulldown and elution.

Figure 10:
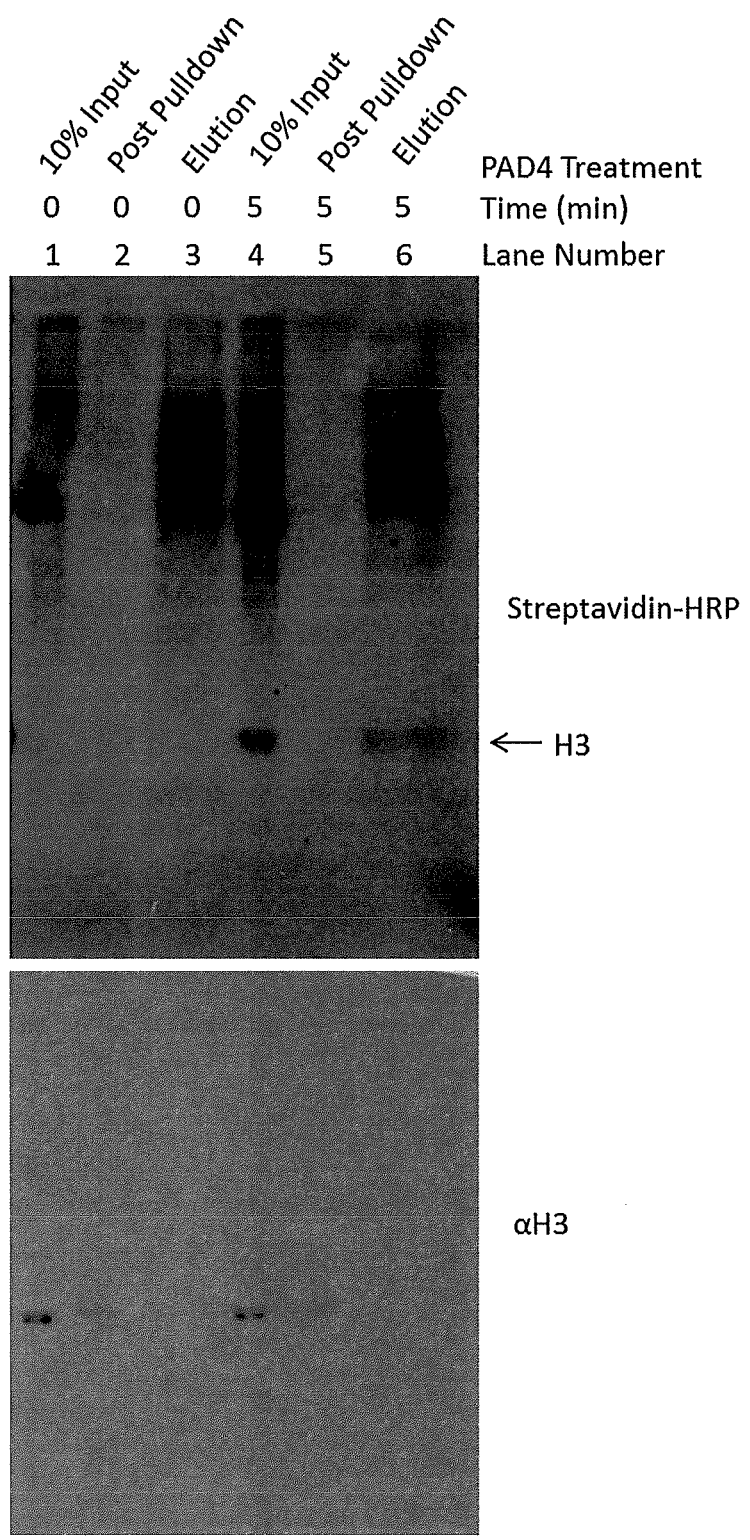
FIG. 10 shows the biotin-PG labeling and isolation of deiminated histone H3 from MCF7 WCE.

Having isolated deiminated histone H3 from a simple solution, the next step taken was to isolate the same amount of protein (~5 µg) from a complex proteome (~70 µg of MCF7 whole cell extract). For these studies, the experiment was performed as described above, except that MCF7 whole cell extracts (WCE; 70 µg) were added to the samples of deiminated histone H3 (0 and 5 min) prior to incubation at 37° C. for 3 h with 20% TCA and 0.1 mM biotin-PG. Samples were quenched, cooled, precipitated, centrifuged, washed, dried, and resuspended as described above. After removing a 30 µL aliquot (pre-pulldown control), a second 30 µl, aliquot was added to 50 µL of High Capacity Streptavidin Agarose Resin (Thermo Scientific) equilibrated in PBS and rocked at room temperature for 30 min. The supernatant was removed and 30 µL set aside as a post-pulldown control. The resin was then washed 1× with 0.2% SDS in PBS (10 min) and 3× with PBS (1 min). Isolated proteins were eluted from the resin in elution buffer (1% SDS, 150 mM biotin, 100 mM thiourea, 3 M urea) at 42° C. for 30 min, followed by 30 min at 95° C. The supernatant was collected and the resin washed 3× with water. These fractions were combined and dried using a SpeedVac evaporator. Samples were resuspended in PBS, boiled with 6×SDS loading dye, and separated by gel electrophoresis (210 V for 45 min). Proteins were then electrotransferred to nitrocellulose (tris-glycine buffer; 80 V; 70 min) and the blot blocked with 5% BSA in PBS for 1 h at room temperature. After washing 2× with PBS (10 min), the blot was treated with streptavidin-HRP (1:5000) in 5% BSA in PBS for 1 h at room temperature. The blot was then washed 3× with PBS (10 min) and 1× with water (5 min) before visualizing with ECL (FIG. 10). Again, to confirm equal loading amounts of histone H3 at both time points, we probed this same blot with an anti-histone H3 antibody, as described above. Briefly, the blot was treated 2× with acidic stripping solution, washed 2× with PBS (10 min), and 2× with TBST (5 min), and blocked with 5% milk in TBST for 1 h at room temperature. The blot was then probed with anti-histone H3 polyclonal antibody (1:5000) in 2.5% milk in TBST for 1 h at room temperature and goat anti-rabbit (HRP) secondary antibody (1:10000) in 2.5% milk in TBST for 1 h at room temperature (rt). The blot was then washed 3× with TBST (5 min) and visualized by ECL (FIG. 10). These results appeared quite similar to the pulldown of H3 from a simple solution. Again, equal amounts of histone were observed at both time points before the pull-down (lanes 1 and 4; anti-histone H3) while only histone H3 deiminated by PAD4 for 5 min was observed when probed with the streptavidin-HRP (lanes 1 and 4; streptavidin-HRP). Again, the anti-histone H3 antibody did not recognize eluted histone, presumably due to Biotin-PG or an alternative modification. Interesting to note was that a significant number of proteins from the WCE were labeled and isolated by the Biotin-PG probe, indicating that certain proteins were citrullinated in vivo by endogenous PADs and that this probe can be used to isolate these proteins. These data taken together provide evidence that the Biotin-PG probe is a highly advantageous tool for labeling, isolating, and detecting citrullinated proteins even in complex matrices (i.e., WCE) and at low amounts (i.e., ~5 µg of histone H3 in 70 µg of WCE).

Conclusions

The design and synthesis of several PG based probes which undergo chemoselective reactions with either citrullines or arginines under acidic and basic conditions, respectively, were described. The probes successfully synthesized include heavy PG ($PG_H$), rhodamine-modified (Rh-PG), and biotin-modified (Biotin-PG). Furthermore, demonstrated were methods to utilize these probes for a host of applications, including monitoring of peptide citrullination by LC-MS, visualization and identification of citrullinated proteins by SDS-PAGE, and isolation of citrullinated proteins by streptavidin pulldown and Western blot analysis. These probes are necessary tools for investigating protein citrullination and are superior to current methods for studying citrullination (i.e., COLDER analysis and anti-citrulline (modified) detection kits). The probes described, as well as derivatives of them, will undoubtedly aid the PAD field of research and further the understanding of the role of these enzymes in rheumatoid arthritis, Alzheimer's disease, ulcerative colitis, and cancer, as well as other diseases in which abnormal protein citrullination plays a role.

Example 2

Probe Synthesis and Characterization

Abbreviations

High-performance liquid chromatography (HPLC); Dimethylformamide (DMF); Dimethylsulfoxide (DMSO); Trifluoroacetic acid (TFA); Acetonitrile (ACN); O-Benzotriazole-N,N,N',N'-tetramethyl-uronium-hexafluoro-phosphate (HBTU); N-Hydroxybenzotriazole (HOBt); Methanol (MeOH); t-Butanol ($^t$BuOH); Tris-(benzyltriazolylmethyl) amine (TBTA)

Heavy Phenylglyoxal Hydrate:

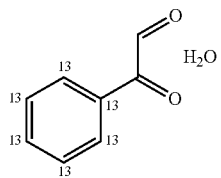

To a stirred solution of $^{13}C_6$-acetophenone (100 mg, 0.79 mmol) in dioxane/$H_2O$ (4:1, 5.0 mL) was added $SeO_2$ (151 mg, 1.35 mmol). The reaction was heated to reflux under $N_2$ atmosphere for 16 h and then was filtered through a plug of celite/$SiO_2$ and purified by reverse phase HPLC using a linear gradient of $H_2O$/ACN plus 0.05% TFA to give the title product in 50% yield. $^1$H NMR ($CD_3OD$, 400 MHz): 8.27-8.25 (m, 1H), 7.88-7.83 (m, 1H), 7.74-7.69 (m, 1H), 7.44-7.43 (m, 1H), 7.34-7.29 (m, 1H), 5.57 (s, 1H). HRMS [EI]$^+$ calcd for $^{13}C_6C_2H_6O_2$ 141.0647. found 141.0650.

N-(3-Acetylphenyl)-2-bromopropionamide

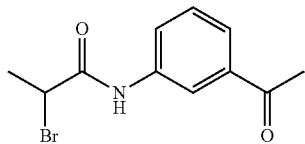

To a stirred solution of 3-amino acetophenone (1.0 g, 7.35 mmol) in dimethylformamide (DMF) (10.0 mL) was added triethylamine ($Et_3N$) (1.11 g, 11.03 mmol) at 0° C. followed by the slow addition of 2-bromopropionyl bromide (1.75 g, 8.08 mmol). The reaction was stirred at room temperature (rt) under $N_2$ atmosphere for 3 h, diluted with water (50.0 mL) and the precipitated pale brown solid was filtered and dried to give the title product in 80% yield. $^1$H NMR ($CDCl_3$, 400 MHz): 8.47 (br s, NH), 8.09-8.08 (m, 1H), 7.92 (dd, J=8.0 Hz, J=1.2 Hz, 1H), 7.73 (dd, J=8.0 Hz, J=1.2 Hz, 1H), 7.46 (t, J=8.0 Hz, 1H), 4.60 (q, J=6.8 Hz, 1H), 2.62 (s, 3H), 1.96 (d, J=7.2 Hz, 3H). $^{13}$C NMR ($CDCl_3$, 100 MHz): 198.0, 167.8, 137.8, 137.7, 129.5, 124.8, 124.6, 119.5, 44.8, 26.7, 22.7. ESI-MS calcd for $C_{11}H_{12}BrNO_2$ (M+Na)$^+$291.99. found 292.0.

N-(3-Acetylphenyl)-2-azidopropionamide

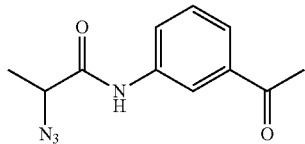 [SMILES: CC(=O)c1cccc(NC(=O)C(C)N=[N+]=[N-])c1]

To a stirred a solution of N-(3-Acetylphenyl)-2-bromopropionamide (800 mg, 2.97 mmol) in DMF (10.0 mL) was added $NaN_3$ (290 mg, 4.46 mmol). The reaction was stirred at room temperature under $N_2$ atmosphere for 12 h, diluted with water, and the precipitated solid was filtered and dried to give the title product in 50% yield. $^1$H NMR ($CDCl_3$, 400 MHz): 8.36 (br s, NH), 8.08-8.07 (m, 1H), 7.90-7.87 (m, 1H), 7.74-7.71 (m, 1H), 7.44 (t, J=8.0 Hz, 1H), 4.25 (q, J=6.8 Hz, 1H), 2.61 (s, 3H), 1.65 (d, J=6.8 Hz, 3H). $^{13}$C NMR ($CDCl_3$, 100 MHz): 197.7, 168.2, 137.8, 137.5, 129.4, 124.6, 124.5, 119.5, 59.4, 26.7, 17.1. ESI-MS calcd for $C_{11}H_{11}N_4O_2$ (M-H)$^+$ 231.09. found 231.1.

2-Azido propionamido-N-3-phenylglyoxyl hydrate

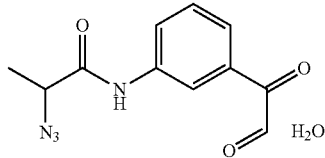

To a stirred solution of azidoacetophenone (200 mg, 0.86 mmol) in dioxane/$H_2O$ (4:1, 10.0 mL) was added $SeO_2$ (145 mg, 1.29 mmol) and the reaction was refluxed under $N_2$ atmosphere for 24 h. The reaction mixture was filtered through $SiO_2$/celite plug, concentrated and purified by reverse phase HPLC using a linear gradient of $H_2O$/ACN plus 0.05% TFA to give the title product in 40% yield. $^1$H NMR ($CD_3OD$, 400 MHz): 8.37 (br s, 1H), 7.92-7.84 (m, 2H), 7.52-7.47 (m, 1H), 5.54 (s, 1H), 4.09-4.06 (m, 1H), 1.57-1.52 (m, 3H). $^{13}$C NMR ($CD_3OD$, 100 MHz): 195.3, 171.6, 139.7, 135.7, 130.2, 126.6, 126.5, 122.2, 96.5, 59.8 17.2. ESI-MS calcd for $C_{11}H_{11}N_4O_4$ (M-H)$^+$263.08. found 263.1.

N-Boc-3-amino-3-propylcarboxamido acetophenone

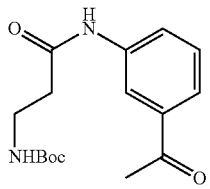 [SMILES: CC(=O)c1cccc(NC(=O)CCNC(=O)OC(C)(C)C)c1]

To a stirred solution of 3-amino acetophenone (1.0 g, 7.35 mmol) in $CH_2Cl_2$ (30.0 mL) was added Boc-β-alanine (1.39 g, 7.35 mmol) followed by Hunig's base (3.85 mL, 22.05 mmol, 3.0 eq). To this solution HBTU (3.48 g, 9.2 mmol, 1.25 eq) and HOBt (992 mg, 7.35 mmol, 1.0 eq) were added at 0° C. and the reaction was stirred at rt under $N_2$ atmosphere for 12 h. The reaction mixture was diluted with $CH_2Cl_2$ (70.0 mL), washed with sat $NaHCO_3$ (100.0 mL), 2 M HCl (50.0 mL) followed by saturated NaCl (50.0 mL). The organic portion was dried over $MgSO_4$, evaporated and the crude material was purified by column chromatography ($SiO_2$, 230-400 mesh) using EtOAc/hexanes as an eluent to give the title product in 80% yield. $^1$H NMR ($CDCl_3$, 400 MHz): 8.36 (br s, NH), 8.10 (s, 1H), 7.90 (d, J=7.6 Hz, 1H), 7.69 (d, J=7.2 Hz, 1H), 7.42 (t, J=8.0 Hz, 1H), 5.21 (br s, NH), 3.51 (q, J=6.0 Hz, 2H), 2.65 (t, J=6.0 Hz, 2H), 2.61 (s, 3H), 1.44 (s, 9H). $^{13}$C NMR ($CDCl_3$, 100 MHz): 198.0, 170.0, 156.5, 138.5, 137.7, 129.3, 124.4, 124.1, 119.3, 79.8, 37.7, 36.4, 28.4, 26.7. ESI-MS calcd for $C_{16}H_{22}N_2O_4$ (M+Na)$^+$329.16. found 329.2.

N-3-Azido-3-propylcarboxamido acetophenone

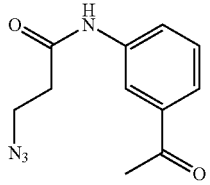

To a stirred solution of N-Boc-3-amino-3-propylcarboxamido acetophenone (1.2 g, 3.92 mmol) in $CH_2Cl_2$ (10.0 mL) was added TFA (10.0 mL). The reaction was stirred at rt for 1 h and evaporated to dryness. To this stirred solution of amine salt in $MeOH/H_2O$ (2:1, 15.0 mL) was added $K_2CO_3$ (1.62 g, 11.76 mmol, 3.0 eq) and a catalytic amount of $CuSO_4.5H_2O$. A freshly prepared $TfN_3$ in $CH_2Cl_2$ was added slowly to this solution and the reaction mixture was stirred at rt for 12 h then acidified with 2M HCl, extracted with $CH_2Cl_2$ (100 mL), washed with saturated NaCl (100 mL) and dried over $MgSO_4$. The solvents were evaporated to dryness and the crude material was crystallized from hexanes to give the title product in 60% yield. $^1$H NMR ($CDCl_3$, 400 MHz): 8.03 (s, NH), 7.94 (d, J=8.0 Hz, 2H), 7.70 (d, J=8.0 Hz, 1H), 7.44 (t, J=8.0 Hz, 1H), 3.74 (t, J=6.4 Hz, 2H), 2.66 (t, J=6.4 Hz, 2H), 2.61 (s, 3H). $^{13}$C NMR ($CDCl_3$, 100 MHz): 198.1, 168.6, 138.2, 137.7, 129.4, 124.7, 124.5, 119.3, 47.2, 36.8, 28.4, 26.7. ESI-MS calcd for $C_{11}H_{12}N_4O_2$ (M+Na)$^+$255.09. found 255.1.

N-3-Azido-3-propylcarboxamido phenylglyoxal hydrate

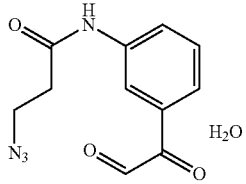

To a stirred solution of azidoacetophenone (200 mg, 0.86 mmol) in dioxane/$H_2O$ (1.5:1, 10.0 mL) was added $SeO_2$ (145 mg, 1.29 mmol, 1.5 eq) and the reaction was refluxed under $N_2$ atmosphere for 24 h, then filtered through $SiO_2$/celite plug, concentrated and purified by reverse phase HPLC ($H_2O$/ACN with 0.05% TFA as a linear gradient) to give the title product in 40% yield. $^1$H NMR ($CD_3OD$, 400 MHz): 8.32 (br s, 1H), 8.31-7.84 (m, 2H), 7.82-7.32 (m, 1H), 5.54 (s, 1H), 3.73-3.64 (m, 2H), 2.82-2.56 (m, 2H). $^{13}$C NMR ($CD_3OD$, 100 MHz): 195.4, 171.6, 140.2, 135.7, 130.1, 127.1, 126.2, 126.1, 121.8, 115.7, 96.4, 38.9, 37.1. ESI-MS calcd for $C_{11}H_{11}N_4O_4$(M−H)$^+$263.08. found 263.0.

N-(Prop-2-ynyl)-5(6)-carboxamidotetramethyl rhodamine (rhod-YNE)

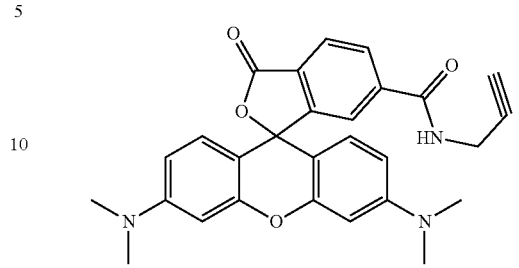

To a stirred solution of 5(6)-carboxytetramethyl rhodamine (50 mg, 0.12 mmol) in DMF (1.0 mL) were added Hunig's base (61 µL, 0.36 mmol, 3.0 eq), propargyl amine (19 mg, 0.36 mmol, 3.0 eq) followed by HBTU (132 mg, 0.36 mmol, 3.0 eq) and HOBt (48 mg, 0.36 mmol, 3.0 eq). The reaction was stirred at rt under $N_2$ atmosphere for 3 h and then diluted with $H_2O$/ACN plus 0.05% TFA (3:2), and purified by reverse phase HPLC using a linear gradient of $H_2O$/ACN plus 0.05% TFA to give the title product in 84% yield. $^1$H NMR ($CD_3OD$, 400 MHz, major isomer): 8.81 (d, J=1.6 Hz, 1H), 8.29 (dd, J=1.6 Hz, J=8.0 Hz, 1H), 7.55 (d, J=8.0 Hz, 1H), 7.18-7.16 (m, 2H), 7.08 (dd, J=9.2 Hz, J=2.4 Hz, 2H), 7.01 (d, J=2.4 Hz, 2H), 4.27 (d, J=2.8 Hz, 2H), 3.32-3.33 (4 s, 12H, 4NCH$_3$), 2.69 (t, J=2.4 Hz, 1H). $^{13}$C NMR ($CD_3OD$, 100 MHz): 167.7, 167.3, 160.5, 159.1, 159.0, 138.4, 137.2, 133.0, 133.4, 131.9, 131.4, 115.6, 114.7, 97.5, 80.5, 72.4, 40.9, 30.2. ESI-MS calcd for $C_{28}H_{26}N_3O_4$ (M+H)$^+$468.18. found 468.2.

N-(3-Glyoxyl)phenylamino)propionyl)-1H-1,2,3-triazol-4-yl)methyl-5(6)-carboxamidotetramethyl rhodamine hydrate (Rh-PG)

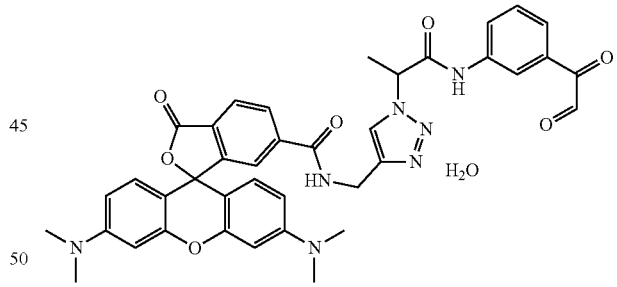

To a stirred solution of rhod-YNE (6.0 mg, 12.84 mmol) and 2-Azido propionamido-N-3-phenylglyoxyl hydrate (4.2 mg, 16.06 mmol) in DMSO/$H_2O$ (1:1, 1.0 mL) were added sodium ascorbate (9.0 mg, 38.54 mmol) in $H_2O$ (500 µL) followed by TBTA (1.3 mg, 2.57 mmol) in DMSO/$H_2O$/$^t$BuOH (3:1:1, 500 µL). To this stirred solution $CuSO_4.5H_2O$ (0.6 mg in 100 µL $H_2O$) was added and the reaction was stirred at rt for 1 h then diluted with ACN/$H_2O$ (2:1, containing 0.05% TFA) and purified by reverse phase HPLC to give the title product in 90% yield. $^1$H NMR ($CD_3OD$, 400 MHz, mixture): 8.83 (d, J=1.6 Hz, 1H), 8.35-8.30 (m, 2H), 8.23 (s, 1H), 7.88-7.84 (m, 2H), 7.54 (d, J=7.6 Hz, 1H), 7.48 (d, J=8.0 Hz, 1H), 7.17-7.14 (m, 2H), 7.08 (dd, J=6.4 Hz, J=3.2 Hz, 2H), 7.0 (d, J=2.4 Hz, 2H), 5.64 (q, J=7.2 Hz, 1H), 5.51 (s, 1H), 4.79 (s, 2H), 3.33 (s, 12H), 1.94 (d, J=6.8 Hz, 3H). $^{13}$C NMR (CD$_3$OD, 100 MHz): 193.7, 167.8, 166.6, 159.1, 157.5, 157.4, 138.2, 134.3, 130.4, 128.7, 120.4, 114.1, 113.2, 95.9, 95.1, 59.6, 39.4, 34.9, 17.0. HRMS calcd for C$_{39}$H$_{38}$N$_7$O$_8$ (M+H)$^+$ 732.2782. found 732.2789.

N-(2-(4-(1-(3-Glyoxyl)phenylamino)propyl)-1H-1,2,3-triazol-4-yl)butanamido)ethyl)-5-D-biotin

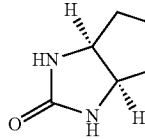 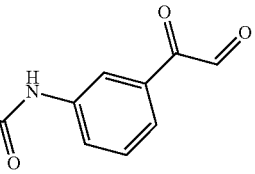

To a stirred solution of biotin-YNE (8.0 mg, 21.05 mmol), prepared as previously described (Jones, J. E., et al. (2011), *ACS Chemical Biology* 7, 160-165), and N-3-Azido-3-propylcarboxamido phenylglyoxal hydrate (7.0 mg, 26.32 mmol) in DMSO (800 µL) were added sodium ascorbate (14.6 mg, 73.68 mmol) in H$_2$O (500 µL) followed by TBTA (1.6 mg, 2.99 mmol) in DMSO/H$_2$O/$^t$BuOH (3:1:1, 500 µL). To this stirred solution, CuSO$_4$.5H$_2$O (0.90 mg in 100 µL H$_2$O) was added and the reaction was stirred at rt for 1 h then diluted with ACN/H$_2$O (2:1, containing 0.05% TFA) and purified by reverse phase HPLC using a linear gradient of H$_2$O/ACN plus 0.05% TFA to give the title product in 50% yield. $^1$H NMR (DMSO-D$_6$, 400 MHz): 10.20 (s, 1H), 8.09 (s, 1H), 7.74 (s, 1H), 7.73-7.71 (m, 2H), 7.56-7.54 (m, 1H), 7.37-7.35 (m, 1H), 7.0 (s, 1H), 6.5 (br s, 1H), 6.18 (s, 1H), 4.54 (t, J=6.4 Hz, 2H), 4.25-4.22 (m, 1H), 4.07-4.04 (m, 1H), 3.00 (s, 4H), 2.91 (t, J=6.4 Hz, 2H), 2.75-2.69 (m, 1H), 2.52 (s, 2H), 2.50 (s, 2H), 2.09-1.93 (m, 5H), 1.71 (t, J=6.4 Hz, 2H), 1.6-1.5 (m, 1H), 1.49-1.30 (m, 2H), 1.28-1.11 (m, 3H). $^{13}$C NMR (CD$_3$OD, 100 MHz): 195.9, 194.8, 172.1, 171.9, 168.4, 162.7, 146.3, 139.3, 135.0, 134.6, 128.9, 124.1, 123.5, 122.2, 61.0, 59.2, 55.3, 45.2, 40.1, 38.3, 36.3, 35.2, 34.7, 28.1, 27.9, 25.1, 25.0, 24.5, 24.1. HRMS calcd for C$_{29}$H$_{38}$N$_8$O$_6$S (M+H)$^+$ 626.2713. found 627.2695.

Example 3

Development of a Phenylglyoxal-Based Probe to Visualize Protein Citrullination Materials and Methods Abbreviations:

High-performance liquid chromatography (HPLC); Dimethylformamide (DMF); Dimethylsulfoxide (DMSO); Trifluoroacetic acid (TFA); Acetonitrile (ACN); Methanol (MeOH); t-Butanol ($^t$BuOH); Tris-(benzyltriazolylmethyl)amine (TBTA); Biotin-Phenylglyoxal (Biotin-PG); Dithiothreitol (DTT); Trichloroacetic acid (TCA); Ethylenediaminetetraacetic acid (EDTA); Ulcerative colitis (UC); Streptavidin-horseradish peroxidase (SA-HRP); Bovine serum albumin (BSA); Phosphate buffered saline (PBS); Enhanced chemiluminescence (ECL).

Chemoselectivity of Phenylglyoxal:

To examine the chemoselectivty of phenylglyoxal, this compound was reacted with two peptides (H4-13 and H4-13-Cit) under neutral and acidic pH. The H4-13 peptide (Ac-SGRGKGGKGLGKG-NH$_2$; SEQ ID NO: 1) and a derivative, H4-13-Cit (Ac-SGRGKGGKGLGKG-NH$_2$; SEQ ID NO: 2), based off of the 13 N-terminal residues of histone H4, were synthesized using standard Fmoc strategies and purified by reverse-phase HPLC. Three samples of each peptide (50 µM) in 50 mM HEPES (50 µL; pH 7.6) was prepared. One sample of each peptide was treated as follows; 1. untreated; 2. with phenylglyoxal (5 mM) at pH 7.6; and 3. with phenyl glyoxal (5 mM) and 20% trichloroacetic acid (TCA; pH<1). Samples were incubated at 37° C. for 3 h and analyzed by MALDI-TOF using α-cyano-4-hydroxycinamic acid (CHCA) as the matrix.

Data from MALDI spectra of H4-13 (Ac-SGRGKG-GKGLGKG-NH$_2$; SEQ ID NO: 1 and H4-13-Cit (Ac-SGCit-GKGGKGLGKG-NH$_2$; SEQ ID NO: 2) labeled under basic or acid conditions with PGL at 37° C. 3 h, indicate that arginine is specifically labeled under basic conditions and citrulline is specifically labeled under acidic conditions.

Data from LC-MS analysis of PG isotopically labeled H4-13 peptide incubated with PAD4 for various times (i.e., 0, 5, 15, and 30 min) showed that there were three m/z peaks observed for the H4-13 Arg peptide (Ac-SGRGKG-GKGLGKG-NH$_2$; SEQ ID NO: 1) labeled with PG$_L$ (i.e., 330 (+4), 439 (+3), and 659 (+2)) and only two were observed for H4-13-Cit peptide (Ac-SGCitGKGGKGLGKG-NH$_2$; SEQ ID NO: 2) labeled with PG$_H$ (i.e., 442 (+3) and 662 (+2)). Three spectra are provided for each time point, highlighting the [M+2], [M+3], and [M+4] peaks. The relative ratio of these peaks is then used to determine the percent citrullination of the given peptide at any one time point.

Amino Acid Selectivity of Rh-PG:

Various amino acids (100 mM; i.e., citrulline, Arg, Lys, Asp, Glu, Thr, Ser, Tyr, Gln, Asn, Cys, Met, His, cystine, and homocitrulline) were prepared in 50 mM HEPES (250 µL; pH 7.6). To this was added 20% TCA and 0.1 mM Rh-PG and samples were incubated at 37° C. for 30 min Samples were analyzed by LC-MS (H2O:ACN+0.1% formic acid gradient) and the ratio of unmodified to amino acid modified Rh-PG determined.

Peptide Analysis of Cysteine Cross-Reactivity:

To test the hypothesis that the Cys-Rh-PG complex was not stable at neutral pH, a peptide containing both citrulline and Cys (i.e., Ac-AHACitACARA-NH$_2$) was synthesized using standard Fmoc strategies and purified by reverse-phase HPLC. Three aliquots of this peptide (0.5 mM) were prepared in 50 mM HEPES (pH 7.6). Samples were treated as follows; 1. untreated; 2. treated with PG (5 mM) and 20% TCA; and 3. treated with PG (5 mM) and 20% TCA. Samples were incubated at 37° C. for 30 min. Samples 1 and 2 were analyzed directly by MALDI-TOF. Sample 3 was first neutralized to a pH of ~7.5 using 3 M NaOH, followed by MALDI-TOF analysis.

Rh-PG Probe Concentration Dependence:

To determine the ideal probe concentration, histone H3 (2 µM) was treated with PAD4 (0.2 µM) in reaction buffer (30 µL; 50 mM HEPES; 50 mM NaCl; 10 mM CaCl$_2$, and 2 mM DTT; pH 7.6) at 37° C. for 1 h and the reaction was then quenched with 50 mM EDTA. This solution of citrullinated H3 and autodeiminated PAD4 was treated with trichloroacetic acid (TCA) (6.0 µL) and various concentrations of Rh-PG (100, 10, 1, or 0.1 µM Rh-PG). Samples were incubated at 37° C. for 30 min. Note that incubations at higher temperatures led to the formation of SDS insoluble aggregates that could not be separated by SDS-PAGE. Excess probe was quenched with 100 mM citrulline before cooling the solutions on ice for 30 min to complete the TCA precipitation. Proteins were isolated by centrifugation at 14,000 rpm for 15 min at 4° C. The supernatant was removed and samples were washed with cold acetone and dried at 100° C. for 5 min. Proteins were resuspended in 25 µL of 50 mM HEPES. All samples were then boiled with 6×SDS loading dye and analyzed by SDS-PAGE (15%; 170 V; 50 min) and fluorescent imaging on a Typhoon Imager (Ex. 532 nm; Em. 580 nm).

Rh-PG Labeling Time Dependence:

Citrullinated H3 and autodeiminated PAD4, prepared as above, were incubated with TCA and 0.1 mM Rh-PG at 37° C. Aliquots (30 µL) were removed at various times (i.e., 0, 0.5, 1, 2, 3, and 4 h) and quenched with 100 mM citrulline for 30 min Samples were then cooled on ice for 30 min, and centrifuged at 14,000 rpm for 15 min at 4° C. The supernatant was removed and samples were washed with cold acetone and dried at 100° C. for 5 min. Proteins were resuspended in 25 µL of 50 mM HEPES, boiled with 6×SDS loading dye and analyzed by SDS-PAGE (15%; 170 V; 50 min) and imaged on a Typhoon Imager (Ex. 532 nm; Em. 580 nm).

Rh-PG Limit of Detection:

Citrullinated H3 and autodeiminated PAD4, prepared as described above, were diluted into 50 mM HEPES pH 7.6 to final concentrations of (2.2 µM, 0.22 µM, 22 nM, 2.2 nM, and 0.22 nM H3) and (0.16 µM, 16 nM, 1.6 nM, 0.16 nM, and 0.016 nM PAD4). These samples were treated TCA and 0.1 mM Rh-PG at 37° C. for 30 min. Solutions were quenched with 100 mM citrulline, cooled on ice for 30 min, and centrifuged at 14,000 rpm for 15 min at 4° C. The supernatant was removed and samples were washed with cold acetone and dried at 100° C. for 5 min. Proteins were resuspended in 25 µL of 50 mM HEPES, boiled with 6×SDS loading dye and various amounts of protein (i.e., 1000, 100, 10, 1, 0.1, and 0 ng citrullinated H3 and 150, 15, 1.5, 0.15, 0.015, and 0 ng autodeiminated PAD4) loaded onto a 15% SDS-PAGE gel. Gel electrophoresis was performed at 170 V for 50 min and the gels analyzed on a Typhoon Imager (Ex. 532 nm; Em. 580 nm).

Temperature Dependence of TCA Precipitations:

To determine the effect of temperature during trichloroacetic acid (TCA) precipitation on protein loading onto a gel, TCA precipitations were carried out at five different temperatures for three different proteins. For this, protein samples (i.e., PAD4 (4.44 µM); H3 (22.2 µM); and H4 (27.9 µM)) were prepared in 50 mM HEPES. To this was added 20% TCA and samples were incubated at various temperatures (i.e., 0, 23, 37, 42, and 55° C.) for 30 min. Samples were cooled on ice 30 min, centrifuged at 14000 rpm at 4° C. for 15 min, and the supernatant was removed. After washing with cold acetone, samples were again centrifuged for 5 min, the supernatant was removed, and samples were dried at 100° C. for 5 min. Proteins were resuspended in 50 mM HEPES, boiled in 6×SDS loading dye for 10 min, and separated by SDS-PAGE (15%; 210 V; 50 min). Gels were Coomassie stained and analyzed by Adobe Photoshop 7.0.

Autodeimination Time Course Experiments:

For these experiments, PAD4 (0.2 µM) was incubated in reaction buffer at 37° C. and 50 µL aliquots were removed and quenched with 50 mM EDTA at various times (i.e., 0, 2, 4, 6, 10, 15, 30, and 60 min). Each aliquot was then divided to give two replicates of the time series. One replicate was incubated at 37° C. for 30 min in 20% TCA with 0.1 mM Rh-PG. Solutions were quenched with citrulline, cooled on ice for 30 min, and centrifuged at 14,000 rpm for 15 min at 4° C. The supernatant was removed and samples were washed with cold acetone and dried at 100° C. for 5 min. Proteins were resuspended in 25 µL of 50 mM HEPES, boiled with 6×SDS loading dye, and analyzed by gel electrophoresis (12%; 170 V; 50 min) and fluorescent imaging (Ex. 532 nm; Em. 580 nm).

The other time series replicates were separated by gel electrophoresis (12% 200 V; 45 min) and electrotransferred to polyvinylidene difluoride (PVDF; tris-glycine buffer; 80 V; 70 min) Autodeiminated PAD4 was then detected using the Anti-Citrulline (Modified) Detection Kit. For this analysis, the PVDF membrane was washed with water twice. Citrulline modification solution was then prepared by combining 5 mL of Reagent A (0.025% $FeCl_3$ in water/98% $H_2SO_4$/85% $H_3PO_4$ (55%/25%/20%); prepared in house) with 5 mL of Reagent B (0.5% 2,3-butanedione monoxime, 0.25% antipyrine, and 0.5 M acetic acid; provided). This solution was added to the blot and incubated without agitation overnight at 37° C. The blot was then washed with water (5× 5 min) and blocked with 5% milk in TBST for 1 h at rt with constant agitation. After blocking, the blot was incubated with the primary anti-citrulline (modified) antibody at a dilution of 1:1000 in 5% milk in TBST for 1 h at rt. This solution was removed and the blot washed with TBST (3×5 min). The blot was then incubated with HRP-conjugated goat anti-rabbit IgG at a dilution of 1:4000 in 5% milk in TBST for 1 h at rt. After washing the blot with TBST (5× 5 min) citrullinated proteins were visualized by enhanced chemoluminescence (ECL). These experiments were performed in duplicate on different days.

Histone H3 Deimination Time Course Experiments:

For these experiments, histone H3 (1.0 µM) was incubated with PAD4 (0.2 µM) in reaction buffer at 37° C. and 75 µL aliquots were removed and quenched with 50 mM EDTA at various times (i.e., 0, 2, 4, 6, 10, 15, 30, and 45 min). Each aliquot was then divided to give two replicates of the time series. One replicate was incubated at 37° C. for 30 min in 20% TCA with 0.1 mM Rh-PG. Solutions were quenched with citrulline, cooled on ice for 30 min, and centrifuged at 14,000 rpm for 15 min at 4° C. The supernatant was removed and samples were washed with cold acetone and dried at 100° C. for 5 min. Proteins were resuspended in 25 µL of 50 mM HEPES, boiled with 6×SDS loading dye, and analyzed by gel electrophoresis (12%; 170 V; 50 min) and fluorescent imaging (Ex. 532 nm; Em. 580 nm).

The second replicate was analyzed by the Anti-Citrulline (Modified) Detection Kit as described above. The third replicate was probed first with anti-H3 (Cit) antibody (catalogue #ab5103; Abeam, Cambridge, Mass.) and an anti-H3 antibody (catalogue #ab1791, Abeam, Cambridge, Mass.). For this analysis, samples were separated by gel electrophoresis (12% 200 V) and electrotransferred to PVDF (tris-glycine buffer; 80 V; 70 min). The blot was blocked with 5% milk in TBST for 1 h at rt before treating with anti-H3 (Cit) polyclonal antibody (2 µL; 1:5000; catalogue #ab5103; Abeam, Cambridge, Mass.) in 2.5% milk in TBST for 1 h at rt. After washing with TBST, the blot was then incubated with HRP-conjugated goat anti-rabbit IgG (2 µL; 1:5000) in 5% milk in TBST for 1 h at rt. After washing the blot with TBST (5× 5 min) citrullinated proteins were visualized by enhanced chemoluminescence (ECL). To confirm equal loading amounts of histone H3, this same blot was stripped and probed with an anti-histone H3 antibody. Briefly, the blot was treated 2× with acidic stripping buffer (0.2 M glycine, 10 mM Tween-20, 0.1% SDS, pH 2.2) (10 min), washed 2× with PBS (10 min), and 2× with TBST (5 min). The blot was subsequently blocked with 5% milk in TBST for 1 h at rt and treated with anti-histone H3 polyclonal antibody (2 µL; 1:5000; catalogue #ab1791, Abcam, Cambridge, Mass.) in 2.5% milk in TBST for 1 h at rt. After washing 3× with TBST (5 min), the blot was treated with goat anti-rabbit (HRP) secondary antibody (2 µL; 1:5,000) in 2.5% milk in TBST for 1 h at rt. The blot was then washed 3× with TBST (5 min) and visualized by ECL. These experiments were performed in duplicate on different days.

Kinetic Assays:

For kinetic measurements, a citrulline standard was first generated to convert fluorescent intensity to citrulline concentration. For this histone H3 (100 µM) was treated with PAD4 (0.2 µM) in reaction buffer at 37° C. for 1 h, followed by quenching with 50 mM EDTA. A portion of this was then analyzed by COLDER in duplicate at two different dilutions to determine the concentration of citrulline in the solution. This value was determined to be 25.6 µM citrulline.

To assure that rate measurements for $k_{cat}/K_m$, were obtained during the linear phase of histone citrullination, a time course assay was performed. For this assay, histones H3 or H4 (50 µM) in reaction buffer were preincubated at 37° C. for 10 min before treatment with PAD4 (0.2 µM). Aliquots (10 µL) were removed at time 0, 2, 4, 6, 8, 10, and 15 min and quenched with EDTA (50 mM) and placed on ice. An aliquot of each sample was then diluted 60 fold in 50 mM HEPES (0.5 µL in 29.5 µL buffer) and treated with 20% TCA and 0.1 mM Rh-PG probe at 37° C. for 30 min. All samples were quenched with citrulline, cooled, centrifuged, washed and dried, as described above. After resuspending in 50 mM HEPES, samples were separated by SDS-PAGE (15%; 170V; 50 min) and imaged on a Typhoon Imager (Ex. 532 nm; Em. 580 nm). These experiments were performed in duplicate.

For the kinetic assay, varying concentrations of both histone H3 and histone H4 (i.e., 0, 10, 23, 50, 75, 100, and 125 µM) were preincubated at 37° C. for 10 min before treatment with and without PAD4 (0.2 µM) in reaction buffer (30 µL) at 37° C. for 6 min. Reactions were quenched with 50 mM EDTA and placed on ice. An aliquot of each sample was then diluted 60 fold in 50 mM HEPES (0.5 µL sample in 29.5 µL buffer) and treated with 20% TCA and 0.1 mM Rh-PG probe at 37° C. for 30 min. Also, a dilution series of citrullinated histone H3 in 50 mM HEPES (25.6 µM stock; 0, 0.25, 0.5, 1.0, and 1.5 µM final) was treated in parallel with 20% TCA and 0.1 mM Rh-PG probe at 37° C. for 30 min to serve as a citrulline standard. All samples were quenched with citrulline, cooled, centrifuged, washed and dried, as described above. After resuspending in 50 mM HEPES, samples were separated by SDS-PAGE (15%; 170 V; 50 min) and imaged on a Typhoon Imager (Ex. 532 nm; Em. 580 nm) Images were analyzed using ImageQuant 5.2 and the initial rates fit to equation 1:

$$v = V\max[S]/(K_m + [S]) \quad \text{(Equation 1)},$$

using Grafit 5.0.1.1. All experiments were done in duplicate on different days.

Rh-PG Analysis of Murine Ulcerative Colitis Serum Samples:

Serum samples Cl-amidine efficacy in a mouse model of ulcerative colitis were obtained and analyzed by the Rh-PG method. Briefly, the protein concentration of serum samples was first obtained using a standard Lowry assay. A sample (2 mg/mL; 30 µL) of each serum sample (i.e., 14 total; 7 DSS; 7 DSS+Cl-amidine) was prepared in 50 mM HEPES and treated with 20% TCA and 0.1 mM Rh-PG for 30 min at 37° C. Samples were then quenched with citrulline, cooled, centrifuged, washed, and dried. After resuspending in 50 mM HEPES, samples were separated by SDS-PAGE (12%; 170V; 50 min) and imaged on a Typhoon Imager (Ex. 532 nm; Em. 580 nm). Images were analyzed using ImageQuant 5.2 and correlation coefficients were determined using Microsoft Excel. These experiments were run in duplicate on different days. Subsequent statistical analysis was done using STATISTICA, utilizing two-tailed, independent student's t-tests to determine significance (i.e., P-value) between diseased and Cl-amidine treated samples. Correlation coefficients were calculated in Microsoft Excel, utilizing a table of critical values of Pearson's r with a degree of freedom value of 12 (n−2) to determine the significance (i.e., P-value) of the correlation between the fluorescence of a particular protein and a disease score.

Results and Discussion

Figure 12:
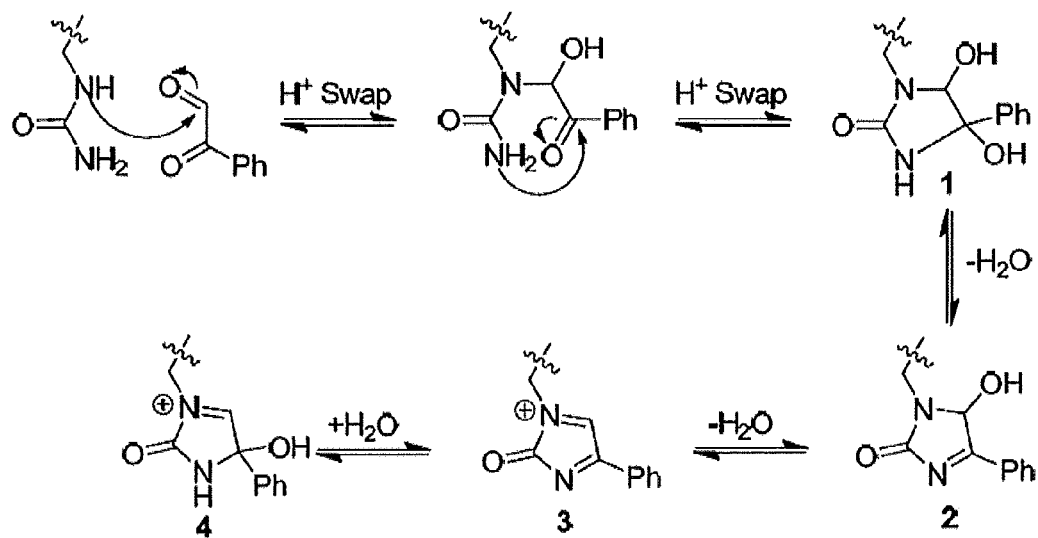
FIG. 12 shows the proposed reaction mechanism between citrulline and phenylglyoxal. Note that four possible structures, all in equilibrium, are possible. Mass spectral analysis indicate that structure 2 is the most likely structure.

The design of the citrulline specific probe described herein is based on the chemoselective reaction that occurs between glyoxals and either citrulline or arginine under acidic or basic conditions, respectively. Although Fleckenstein et al., (*Anal. Biochem.* 2010, 403, 43) reported the derivatization of phenylglyoxal onto the solid phase via the para position, this chemistry was not amenable to the solution phase. Therefore the focus was on synthesizing phenylglyoxal compounds with an azido group on the meta position that could be reacted with alkyne modified rhodamine via the copper catalyzed azide-alkyne cycloaddition. Without wishing to be bound by any theory, it is hypothesized that the reaction between citrulline and phenylglyoxal likely proceeds as shown in FIG. 12.

Figure 13:
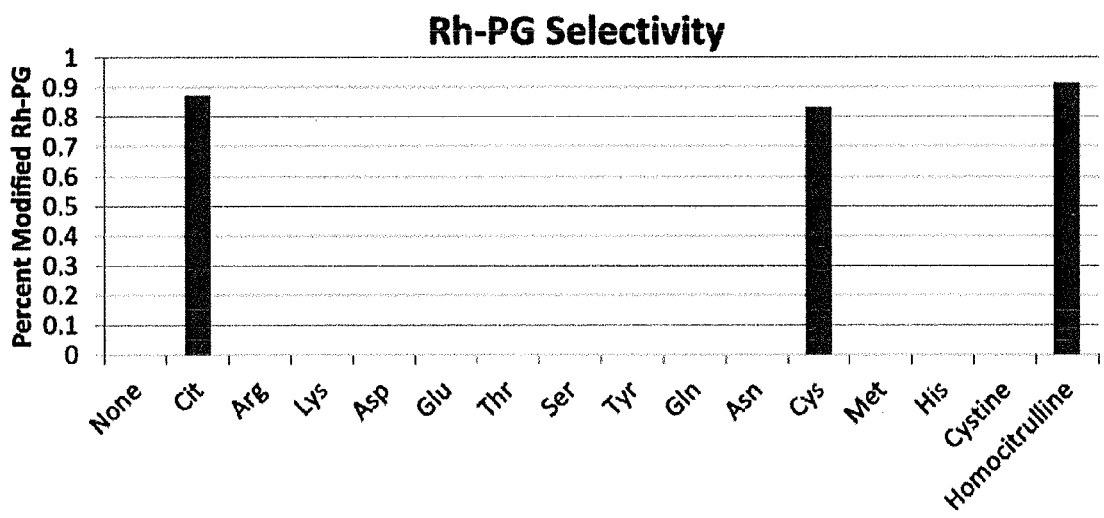
FIG. 13 shows the selectivity of the Rh-PG probe. Rh-PG treated with excess amino acid under acidic conditions for 30 min at 37° C. followed by analysis by LC-MS to determine the percent of Rh-PG modified by the amino acid.
Figure 14:
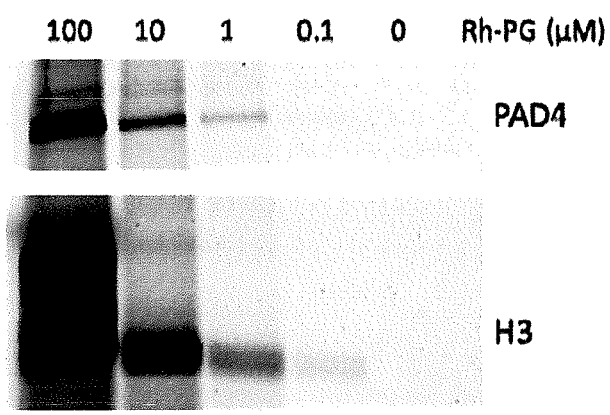
FIG. 14 shows that the Rh-PG probe labels autodeiminated PAD4 and citrullinated histone H3 in a concentration dependent manner. Histone H3 and PAD4 were deiminated by PAD4, followed by treatment with varying concentrations of Rh-PG under acidic conditions for 30 min at 37° C. Samples were separated by SDS-PAGE and analyzed on a fluorescent scanner.
Figure 15:
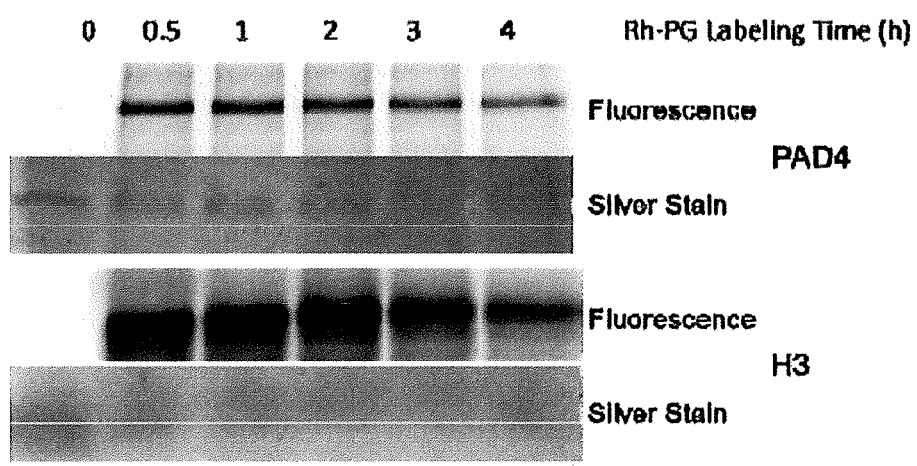
FIG. 15 shows that the Rh-PG labeling of autodeiminated PAD4 and deiminated histone H3. Samples were treated with Rh-PG under acidic conditions at 37° C. for varying times, separated by SDS-PAGE, and imaged. Rh-PG labeling is essentially complete after 0.5 h and extended labeling times lead to decreased protein loading on the gel.
Figure 16A:
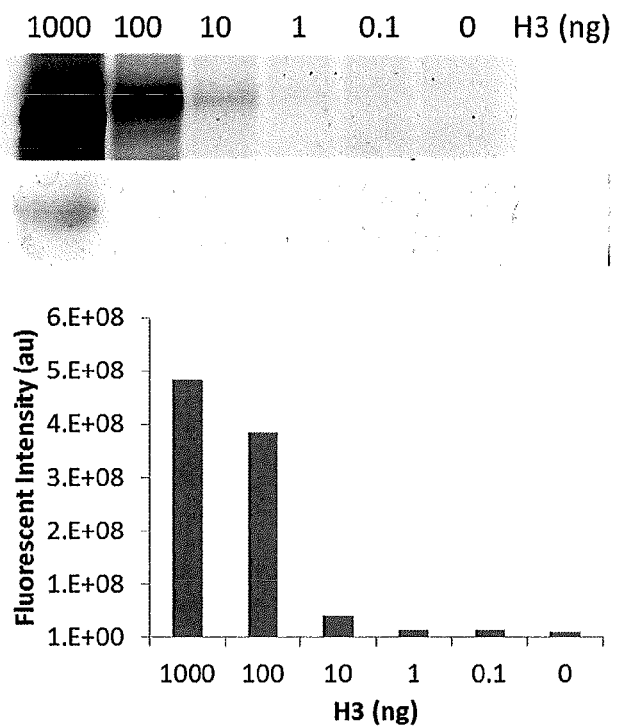
FIGS. 16A and 16B show the limit of detection of the Rh-PG probe.
Figure 16B:
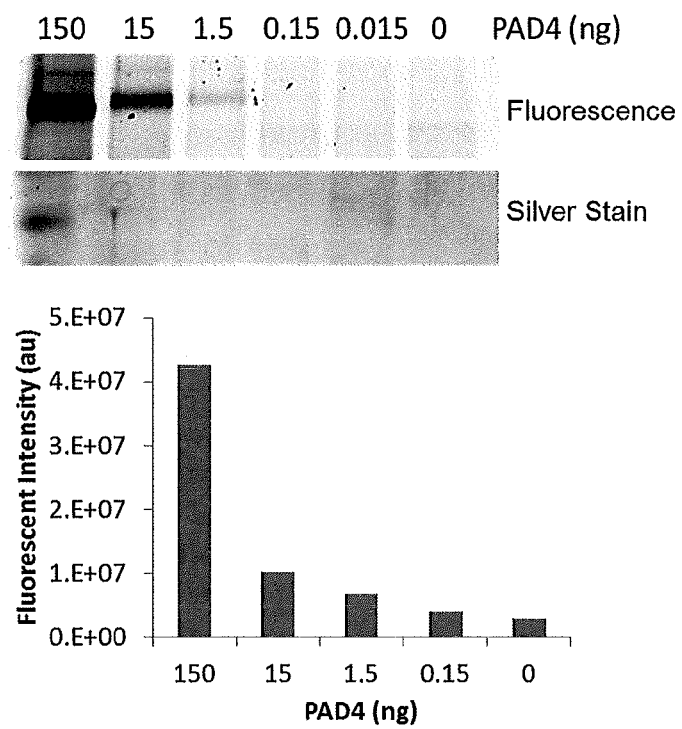
Figure 17:
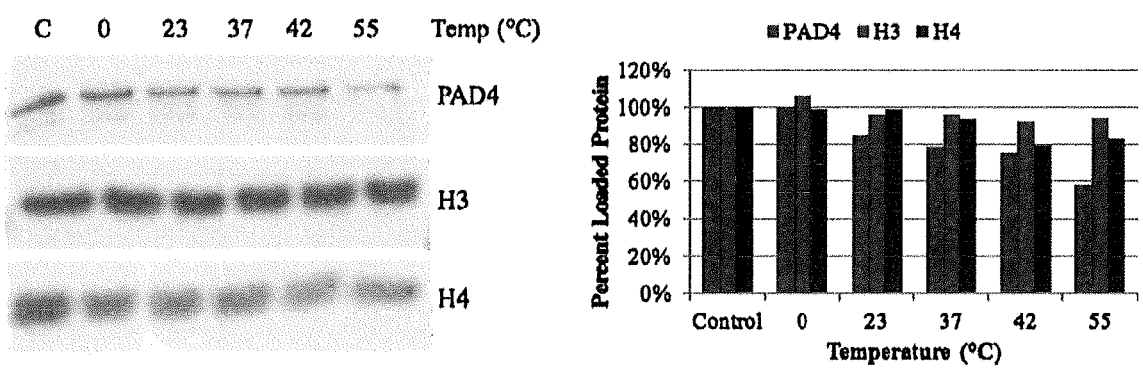
FIG. 17 shows TCA precipitations of various proteins at different temperatures to show that increased temperature during TCA precipitations decreases protein loading. Recombinant PAD4, H3, and H4 were treated with 20% TCA at varying temperatures for 30 min. Samples were washed and analyzed by SDS-PAGE and coomassie staining.

Probe selectivity was first determined against commonly reactive amino acids, showing that under acidic conditions, Rh-PG reacted selectively with citrulline, homo-citrulline, and cysteine (FIG. 13). Using a peptide substrate containing both citrulline and cysteine, it was shown that the thiohemiacetal generated between Rh-PG and Cys is hydrolyzed at neutral pH, while the cyclic system formed between Rh-PG and citrulline is not. Since the gel-based screening method includes a neutralization step prior to gel loading, the problem of cysteine cross-reactivity is effectively negated; the selectivity versus Cys under these conditions is ≥650-fold. After demonstrating that the PG probe is capable of selectively reacting with either arginine or citrulline in a pH dependent manner, conditions for probe labeling were optimized, including the ideal probe concentration (i.e., 100 µM; FIG. 14), ideal labeling time (i.e., 30 min; FIG. 15), and the probe sensitivity/LOD (i.e., ~10 ng (0.67 pmol) of citrullinated histone H3 and ~1 ng (12.7 fmol) of autodeiminated PAD4; FIGS. 16A, 16B). The different LODs are due to differences in the citrulline content of the two proteins. Since Rh-PG labeling is performed in 20% trichloroacetic acid (TCA) at 37° C., it is noted that increased labeling temperatures and times lead to the formation of SDS insoluble protein aggregates and decreased gel loading (FIG. 17). Also, quenching of excess probe with citrulline after labeling reduced background labeling of arginine residues upon resuspension of the protein (data not shown).

Figures 18A, 18B:
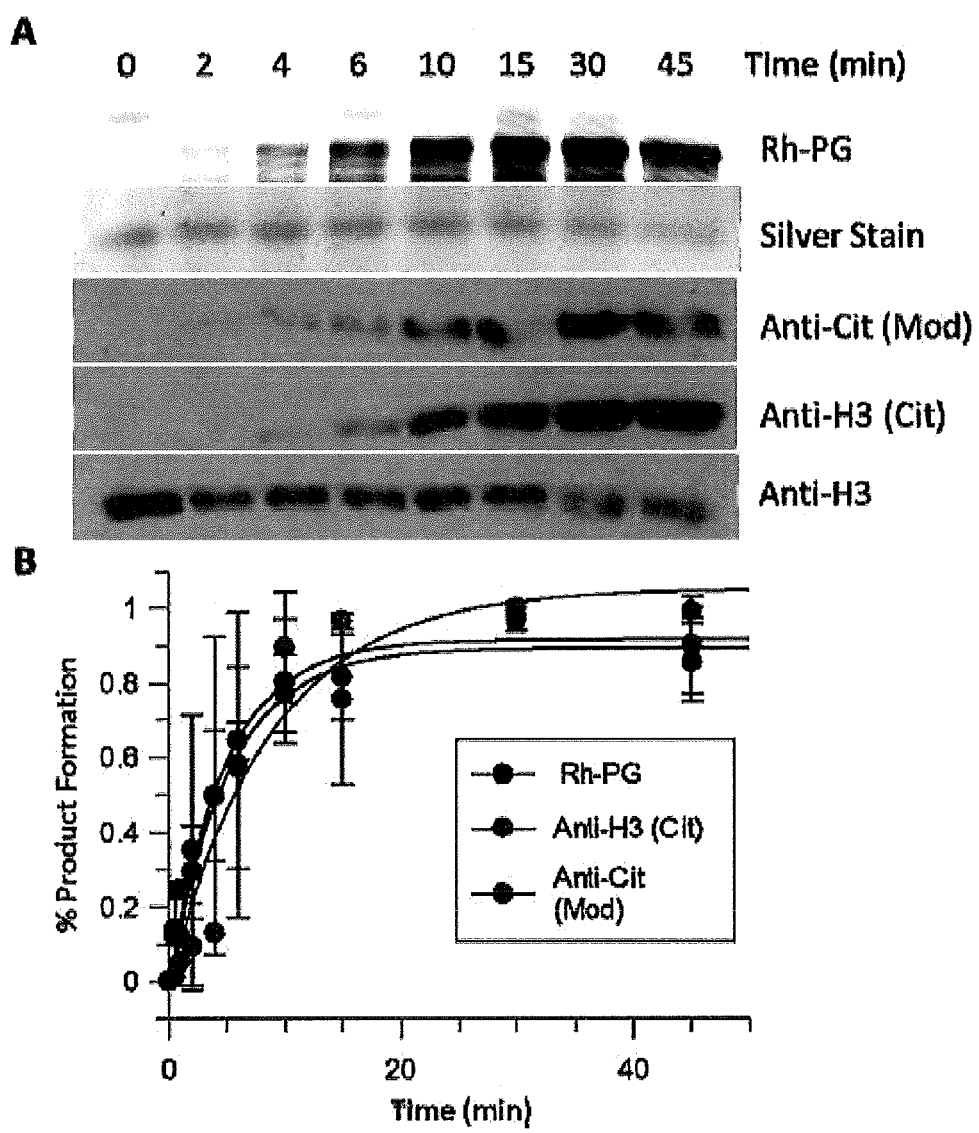
FIG. 18A shows the time course of histone H3 citrullination by PAD4 analyzed by the Rh-PG method (top), ACM kit (middle), and anti-H3 (cit) antibody (lower middle). Silver staining (upper middle) confirms equal protein loading for the Rh-PG method of detection and probing by an anti-H3 antibody (bottom) confirms equal protein loading for the antibody based analysis.
FIG. 18B: Analysis of all three methods for analysis of H3 citrullination, showing that they compare favorably.

To demonstrate that the Rh-PG probe detection method compares favorably to the commercially available ACM kit, a comparative analysis of the two methods was conducted using PAD4 autodeimination as the endpoint. PAD4, autodeiminated for various amounts of time, was analyzed with Rh-PG and the ACM kit according to the manufacturer's instructions. Silver staining of the fluorescent gel was done to confirm equal protein loading. Analysis of this data indicates that the two techniques provide virtually identical results. The rate of recombinant histone H3 citrullination was also followed and the results of the two methods again show essentially identical results (FIGS. 18A, 18B). These data indicate that the Rh-PG method is comparable to commercially available techniques. However, compared to the ACM kit, the Rh-PG labeling method takes significantly less time (~3 h versus ≥25 h), requires fewer steps (6 versus 12), and simpler analysis (fluorescent imaging versus Western blotting).

Given the high sensitivity of Rh-PG, it was next determined whether this methodology could be used to accurately quantify changes in citrullination by determining the steady state kinetic parameters for a protein substrate. Although the traditional COLDER assay has been used in do this type of analysis on protein substrates (Slack, J. L.; et al., *Biochemistry* 2011, 50, 3997), it is difficult to obtain highly accurate rates due to the limited sensitivity of the COLDER assay and the high concentrations of proteins required to accurately measure citrulline production. For the Rh-PG kinetic experiments, H3 citrullination was first monitored as a function of time to ensure that the kinetic parameters were determined under initial velocity conditions. Note that Rh-PG fluorescence was converted to citrulline concentration, using a citrulline standard curve. Having identified a specific time that could be used to obtain the initial rates, this method was used to determine the steady-state kinetic parameters for the citrullination of histone H3 by PAD4. The results of this analysis provided a $k_{cat}/K_m$ value of $4800 \pm 1100$ $M^{-1}$ $s^{-1}$. Similar analyses performed on the PAD4 catalyzed deimination of histone H4 gave a value of $2800 \pm 200 M^{-1}$ $s^{-1}$. Given the poor sensitivity and high signal to noise ratios of current methods for determining the rates of protein citrullination (i.e., the COLDER analysis and ammonia detection methods; Kearney, P. L.; et al., *Biochemistry* 2005, 44, 10570; Hou, Y.-C.; et al., *Eur. J. Nutr.* 2012, DOI: 10.1007/s00394-012-0416-3), the accuracy and excellent sensitivity of the method herein (note that samples were diluted 60 fold before analysis) provides a unique tool to study protein deimination because it permits the determination of $K_m$ values for high affinity protein substrates and allows for the study of proteins that are difficult to produce in large quantities.

Figures 19A, 19B:
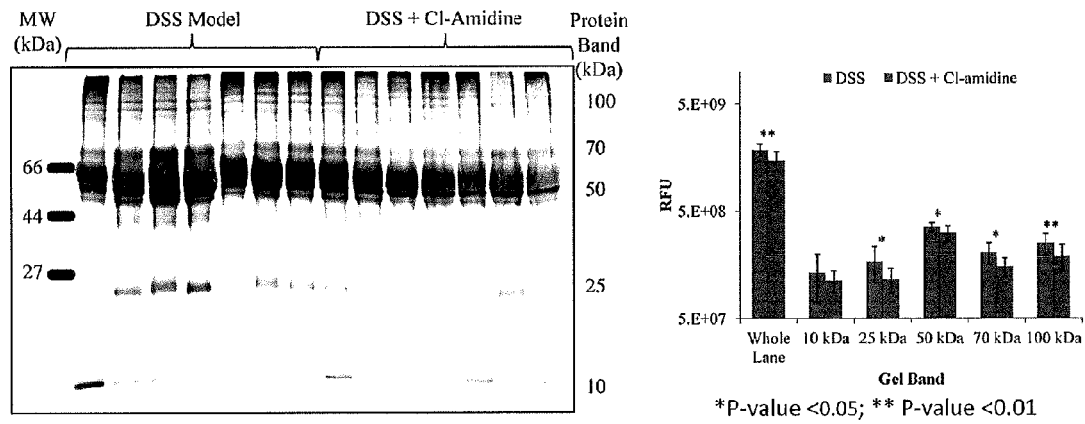
FIGS. 19A, 19B show protein citrullination in serum samples.

It was envisioned that a key advantage of this probe would be its facile ability to visualize target engagement (i.e., decreased citrullination upon inhibitor treatment) as well as the detection/identification of disease-associated biomarkers. To demonstrate its utility for these types of analyses, changes in protein citrullination were evaluated using serum samples from a previous study demonstrating that Cl-amidine, a PAD inhibitor, reduces disease severity in the DSS mouse model of ulcerative colitis (Chumanevich, A. A. et al., *J. Am. J. Physiol: Gastrointest. Liver Physiol.* 2011, 300, G929). Citrullinated proteins present in these samples were labeled with the Rh-PG probe, separated by SDS-PAGE, and fluorescent proteins imaged (FIG. 19A). Whole lane fluorescence was analyzed as a function of the addition of Cl-amidine (FIG. 19B). Consistent with the previous studies, which used the COLDER assay to measure changes in total protein citrullination, analysis of whole lane fluorescence revealed a significant (P-value<0.01) reduction in fluorescence intensity for the serum samples treated with Cl-amidine. Note that selectivity analysis indicated the Cl-amidine itself does not react with the probe. Unlike the previous analysis, which only measures total protein citrullination, the Rh-PG method allowed for the monitoring of effects on specific proteins, as opposed to global serum citrullination. Based on visual inspection of the fluorescent images, five protein bands (at 10, 25, 50, 70, and 100 kDa) were visualized within each lane that appeared to show a marked change in protein citrullination as a function of Cl-amidine. From a comparison of the fluorescent intensities of these bands between the two groups, it was observed that 4 out of the 5 protein bands show statistically significant decreases in citrullination in response to Cl-amidine (P-value<0.05; Table 2). The only protein band analyzed that did not show a significant decrease in response to Cl-amidine (P-value 0.44) was the band at 10 kDa.

TABLE 2

| P-values between DSS and DSS + Cl-amidine samples. | | | | | |
|---|---|---|---|---|---|
| | Whole Lane | 10 kDa | 25 kDa | 50 kDa | 70 kDa | 100 kDa |
| P-values | 0.00613 | 0.436 | 0.046 | 0.0195 | 0.0112 | 0.00823 |

TABLE 3

Disease scoring of mice from the DSS induced ulcerative colitis study.

| Group | ##/Sex | Weight (start) | Weight (end) | Colon Length (cm) | Weight Diff. (g) | WBC (m/mm³) | Lym (m/mm³) | Inflam. Score | Treatment |
|---|---|---|---|---|---|---|---|---|---|
| Group 7 | 7.1M | 20.2 | 20.3 | 7.8 | 0.1 | 9.43 | 4.99 | 21 | 2% DSS + PBS |
| WT | 7.2M | 21.6 | 19.4 | 8 | −2.2 | 6.82 | 4.37 | 32 | |
| | 7.3M | 20.3 | 20.3 | 5 | 0 | 51.7 | 21.92 | 24 | |
| | 7.4M | 22.1 | 21.4 | 6 | −0.7 | 17.13 | 9.28 | 24 | |
| | 7.5M | 23.9 | 23.9 | 8 | 0 | 12.97 | 7.19 | 32 | |
| | 7.6M | 21 | 18.7 | 7 | −2.3 | 12.52 | 7.85 | 16 | |
| | 7.7M | 24.6 | 20.4 | 8 | −4.2 | 10.96 | 6.04 | 16 | |
| Average | | 22.0 | 20.6 | 7.1 | −1.3 | 17.4 | 8.8 | 23.6 | |
| Group 8 | 8.1M | 22.6 | 23.4 | 7.6 | 0.8 | 9.75 | 5.68 | 14 | 2% DSS + |
| WT | 8.2M | 21.9 | 22.05 | 7.6 | 0.15 | 9.08 | 3.87 | 24 | Cl-Amidine |
| | 8.3M | 21.9 | 22.7 | 8.1 | 0.8 | 18.14 | 11.35 | 14 | @ 75 mg/kg |
| | 8.4M | 22.8 | 24.1 | 8.2 | 1.3 | 15.12 | 9.4 | 12 | |
| | 8.5M | 24.5 | 25 | 8.6 | 0.5 | 11.46 | 6.87 | 10 | |
| | 8.9M | 21.8 | 22.5 | 8 | 0.7 | 15.91 | 9.35 | 16 | |
| | 8.10M | 23.3 | 23.6 | 8.4 | 0.3 | 16.41 | 10.83 | 12 | |
| Average | | 22.7 | 23.3 | 8.1 | 0.7 | 13.7 | 8.2 | 14.6 | |

Figures 20A, 20B:
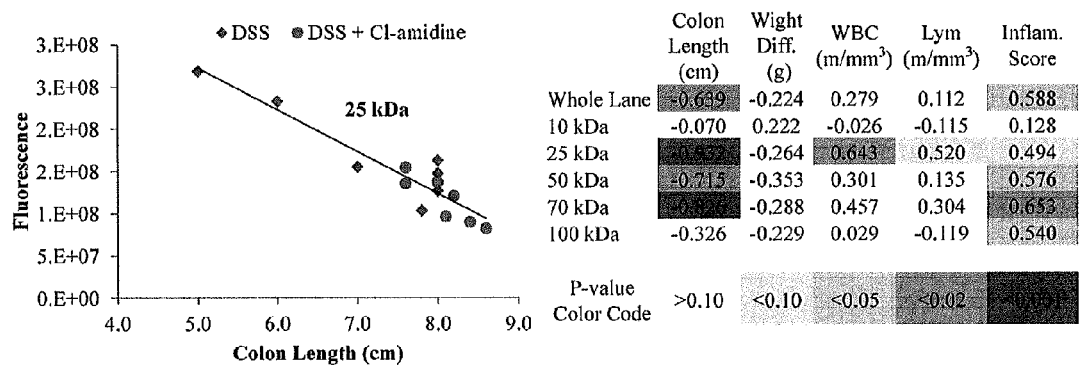
FIGS. 20A, 20B show the correlation of protein citrullination with disease severity.

Given these findings, it was hypothesized that direct correlations between the citrullination of these proteins and disease severity may exist. To test this hypothesis, the fluorescence intensity data for the five proteins described above was compared to each of five different disease metrics obtained for the mice in this study (i.e., colon length, weight difference, white blood cell count, lymphocyte count, and inflammation score) (Table 3). Correlation plots (FIG. 20A) and correlation coefficients (FIG. 20B) were generated, and colon length (4 out of 6 significant correlations) and inflammation scores (5 out of 6 significant correlations) showed the highest correlations between disease severity and citrulline levels. Note that these two endpoints are the key indicators of disease severity.

Interestingly, the 10 kDa protein, the only protein with no significant decrease in citrullination in response to Cl-amidine, also has no significant correlation to any of the disease scores, meaning it essentially serves as a negative control. The highest correlation coefficients, and therefore the most relevant correlations, exist between colon length and the levels of the citrullinated 25 kDa and 70 kDa proteins (correlation coefficients=−0.932 and −0.826, respectively) Important to note is that the average protein levels, as analyzed by coomassie staining, did not change between untreated and Cl-amidine treated samples for either of these protein bands, indicating that the change in fluorescence is indeed due to a change in citrullination. The 25 kDa band also showed the greatest number of significant correlations with disease severity (i.e., 4 out of 5 disease activity scores). The only outlier is weight loss, which also did not correlate with any of the other protein bands analyzed. The strong correlation between citrullination of the 25 kDa protein and common disease activity scores, especially colon length, provides evidence that this protein is a biomarker of ulcerative colitis.

Although the Rh-PG probe is clearly useful for studying recombinant proteins, which is itself beneficial to the PAD field, this work demonstrates its true utility in studying more complex samples from disease states (e.g., UC, RA, Alzheimer's disease, Parkinson's disease, and cancer, to name a few) in which dysregulated PAD activity plays a role. For example, while anti-citrulline protein antibodies (ACPAs) are well established biomarkers for RA, less is understood about the targets of these antibodies. Additionally, the identities of citrullinated protein biomarkers for the other diseases in which the PADs are involved, the compositions and methods provided herein would provide the identification of such biomarkers.

In total, these data demonstrate that the Rh-PG probe is a powerful chemical probe of protein citrullination that will undoubtedly be useful for providing robust and telling insights into the role of particular PAD substrates in PAD related diseases. Further work is currently underway to determine the identity of that 25 kDa protein and identify and characterize unique disease biomarkers in other diseases in which the PADs play a role.

Example 4

Biotin-PG

Materials and Methods

Biotin-PG Limit of Detection:

Histone H3 (10 µM) was treated with PAD2 (0.2 µM) in Reaction Buffer (50 mM HEPES, 50 mM NaCl, 10 mM $CaCl_2$, 2 mM DTT; pH 7.6) at 37° C. for 5 min before quenching the reaction with 50 mM EDTA. Protein was diluted into 50 mM HEPES pH 7.6 to final concentrations of 0.22 µM, 22 nM, 2.2 nM, and 0.22 nM H3. These samples were treated with TCA and 0.1 mM Biotin-PG at 37° C. for 30 min Solutions were quenched with 100 mM citrulline, cooled on ice for 30 min, and centrifuged at 14,000 rpm for 15 min at 4° C. The supernatant was removed and samples were washed with cold acetone and dried at 100° C. for 2 min. Proteins were resuspended in 50 mM HEPES containing 100 mM arginine, boiled with 6×SDS loading dye, and various amounts of protein (i.e., 100, 10, 1, 0.1, and 0 ng) loaded onto a SDS-PAGE gel. Separated proteins were transferred to nitrocellulose (tris-glycine buffer; 80V; 60 min). The blot was blocked in 5% BSA in PBS 1 h at room temperature (rt) before treatment with Streptavidin (SA)-HRP (0.5 µL; 1:20000) in 5% BSA in PBS for 10 min at rt. The blot was washed 3× with PBS (5 min), 1× with water (5 min), and visualized by enhanced chemiluminescence (ECL).

Biotin-PG Pulldown from Lysates:

Histone H3 (10 µM) was treated with PAD2 (0.2 µM) in Reaction Buffer and aliquots removed at various times (i.e., 0, 1, and 3 min) and PAD2 activity quenched with 50 mM EDTA. Aliquots were divided evenly and to one set was added 1 mg/mL MCF7 whole cell extracts. All samples were then treated with 20% TCA and 0.1 mM Biotin-PG for 30 min and 37° C. before quenching with citrulline, cooling, centrifuging, washing, and drying as described above. Proteins were resuspended in 50 mM HEPES containing 100 mM arginine and 0.1% SDS, boiled for 10 min, and sonicated in a bath sonicator for 2-5 s. A small aliquot was removed to serve as a loading control. The remaining sample was added to 50 µL of high capacity streptavidin agarose (Thermo Fisher Scientific Inc.), equilibrated in PBS and tumbled gently overnight at 4° C. Samples were then centrifuged at 2,500 rpm for 2 min at 4° C. and the supernatant removed. Samples were then washed with 0.2% SDS in PBS for 10 min at rt, 3× with PBS, and 3× with water. Proteins were eluted from the resin in fresh Elution Buffer (50 µL; 6 M urea, 2 M thiourea, 30 mM biotin, and 2% SDS) at 42° C. for 1 h. After brief centrifugation, the supernatant was then transferred to a 10 kDa micro-concentrator, the resin washed 1× with water (100 µt), centrifuged again, and the water combined with the previous eluant in the micro-concentrator. To complete removal of excess chaotropic agents, the micro-concentrators were centrifuged at 16×g for 10 min and the sample diluted with water (100 µL) and centrifuged twice more. Proteins were collected from the micro-concentrator and boiled with 6×SDS loading buffer for 10 min. The samples were then separated by SDS-PAGE and transferred to nitrocellulose (tris-glycine buffer; 80 V; 60 min) The blot was blocked in 5% BSA in PBS for 1 h at rt before treatment with SA-HRP (0.5 µL; 1:20000) in 5% BSA in PBS for 10 min at rt. The blot was washed 3× with PBS (5 min), 1× with water (5 min), and visualized by ECL.

Biotin-PG Pulldown of Murine Ulcerative Colitis Serum Samples:

Serum samples from a previously published study (A. A. Chumanevich, et al., *American Journal of Physiology—Gastrointestinal and Liver Physiology* 2011, 300, G929-G938) of Cl-amidine efficacy in a mouse model of DSS-induced ulcerative colitis (UC) were analyzed by Biotin-PG pulldown. Specifically, diseased mouse 7.3, reported earlier to have elevated levels of citrullination that correlate strongly with UC severity (K. L. Bicker, et al., *J Am Chem Soc* 2012, 134, 17015-17018), was analyzed. Briefly, the serum sample (500 µg total serum protein) was first diluted 1:1 with 50 mM HEPES pH 7.6 (25 mM HEPES final concentration), and then combined with TCA (20% final concentration) and Biotin-PG (0.1 mM final concentration) for 30 min at 37° C. before quenching with citrulline, cooling, centrifuging, washing, and drying as described above. Proteins were resuspended in 50 mM HEPES containing 100 mM arginine and 0.1% SDS, boiled for 10 min, and sonicated in a bath sonicator for 2-5 s. A small aliquot was removed to serve as a loading control. The remaining sample was added to 50 μL of high capacity streptavidin agarose, equilibrated in PBS and tumbled gently overnight at 4° C. Resin was washed and the proteins eluted as described above. Proteins were separated by SDS-PAGE, stained with GelCode Blue Stain Reagent (Thermo Fisher Scientific Inc.) for 1 h at rt, and destained with water.

For Western blotting analysis, a parallel SDS-PAGE gel of the eluted proteins was transferred to nitrocellulose (tris-glycine; 80 V; 60 min) and blocked with 5% BSA in PBS for 1 h at rt. The blot was treated with SA-HRP (0.5 μL; 1:20000) in 5% BSA in PBS for 10 min at rt, washed 3× with PBS (5 min), 1× with water (5 min), and visualized by ECL. To probe for ApoA1, the blot was treated 2× with acidic stripping buffer (0.2 M glycine, 10 mM Tween-20, 0.1% SDS, pH 2.2) (10 min), washed 2× with PBS (10 min), and 2× with TBST (5 min). The blot was subsequently blocked with 5% milk in TBST for 1 h at rt and treated with anti-apolipoprotein A-1 polyclonal antibody (2.5 μL; 1:4000; catalogue #NB600-609, Novus Biologicals, Littleton, Colo.) in 2.5% milk in TBST for 1 h at rt. After washing 3× with TBST (5 min), the blot was treated with bovine anti-goat (HRP) secondary antibody (2.5 μL; 1:4000) in 2.5% milk in TBST for 1 h at rt. The blot was then washed 3× with TBST (5 min) and visualized by ECL.

In-Gel Digestion and Proteomic Identification:

To identify proteins isolated with the Biotin-PG probe, protein bands of interest were cut from the gel after GELCODE Blue staining. Gel pieces were prepared for digestion by treating with dehydrating solution (50 μL; 2:1 acetonitrile:25 mM ammonium bicarbonate) for 15 min, rehydrating in 25 mM ammonium bicarbonate (50 μL) 10 min, and treating again with dehydrating solution (50 μL) for 15 min before drying the pieces in a Speed-Vac. To this was added DTT (25 μL; 10 mM) in 25 mM ammonium bicarbonate and the sample incubated at 56° C. for 1 h, followed by treatment with iodoacetamide (25 μL; 55 mM) in 25 mM ammonium bicarbonate for 45 min in the dark. The sample was then washed with 25 mM ammonium bicarbonate (25 μL) and dehydrated, rehydrated, dehydrated, and dried in the Speed-Vac as described above. To the dried sample was added enough trypsin solution (12.5 ng/μL in 25 mM ammonium bicarbonate) to completely rehydrate the gel piece (~5-10 μL). After 20 min, a minimal amount of 25 mM ammonium bicarbonate was added to completely submerge the gel piece and the sample incubated at 37° C. for 4.5 h. Digested samples were analyzed on a nanoLC (Eksigent Technologies; Dublin, Calif.) interfaced with an ESI-LTQ Orbitrap mass spectrometer (Thermo Fisher Scientific; San Jose, Calif.) and the proteins identified by searching the product ion data against the SwissProt database using MASCOT (Matrix Science; London, UK). Results were viewed in Scaffold 3.5.2 (Proteome Software; Portland, Oreg.) with the threshold for protein identification set to a minimum of 5 peptides, 99% min protein, and 95% min peptide.

Results and Discussions

Figure 21A:
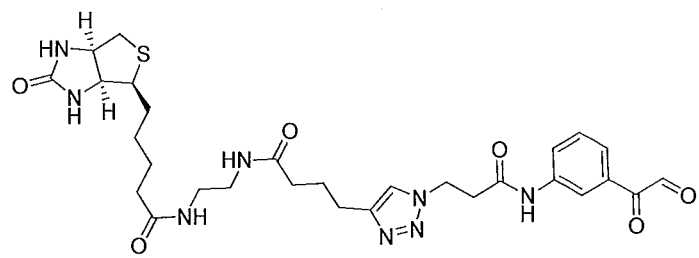
FIGS. 21A to 21C show the limit of detection of a biotin-PG probe.
Figure 21B:
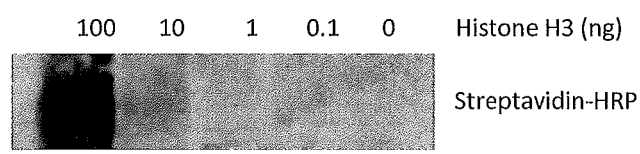
Figure 21C:
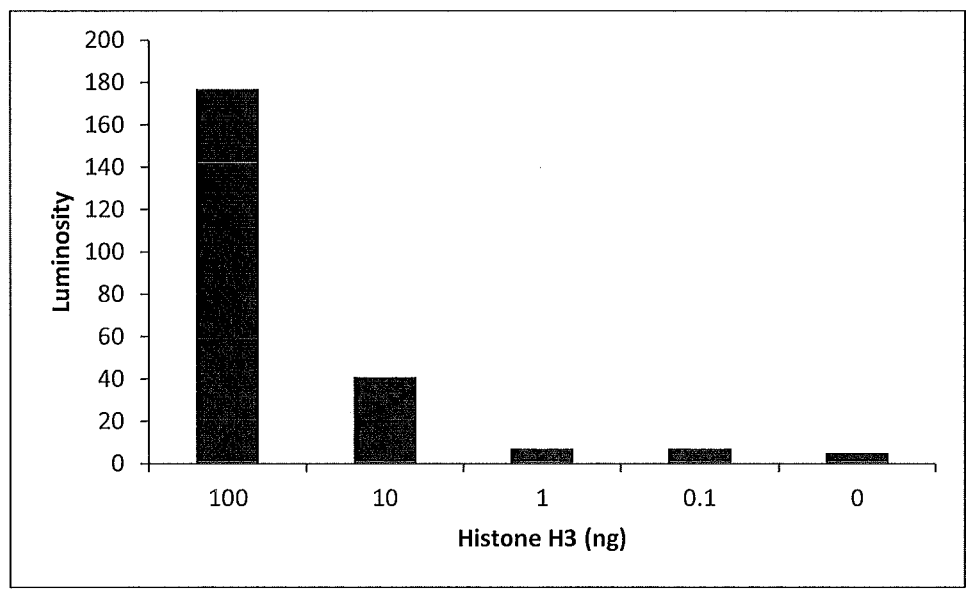

It was first set out to determine the limit of detection of the Biotin-PG probe. Serial dilutions of citrullinated H3 were labeled with Biotin-PG and analyzed by streptavidin-HRP Western blotting (FIGS. 21A-21C). These results indicate that the limit of detection for the Biotin-PG probe is 10 ng of citrullinated H3. This puts the limit of detection of Biotin-PG in the femtomole range, similar to Rh-PG.

Figures 22A, 22B, 22C:
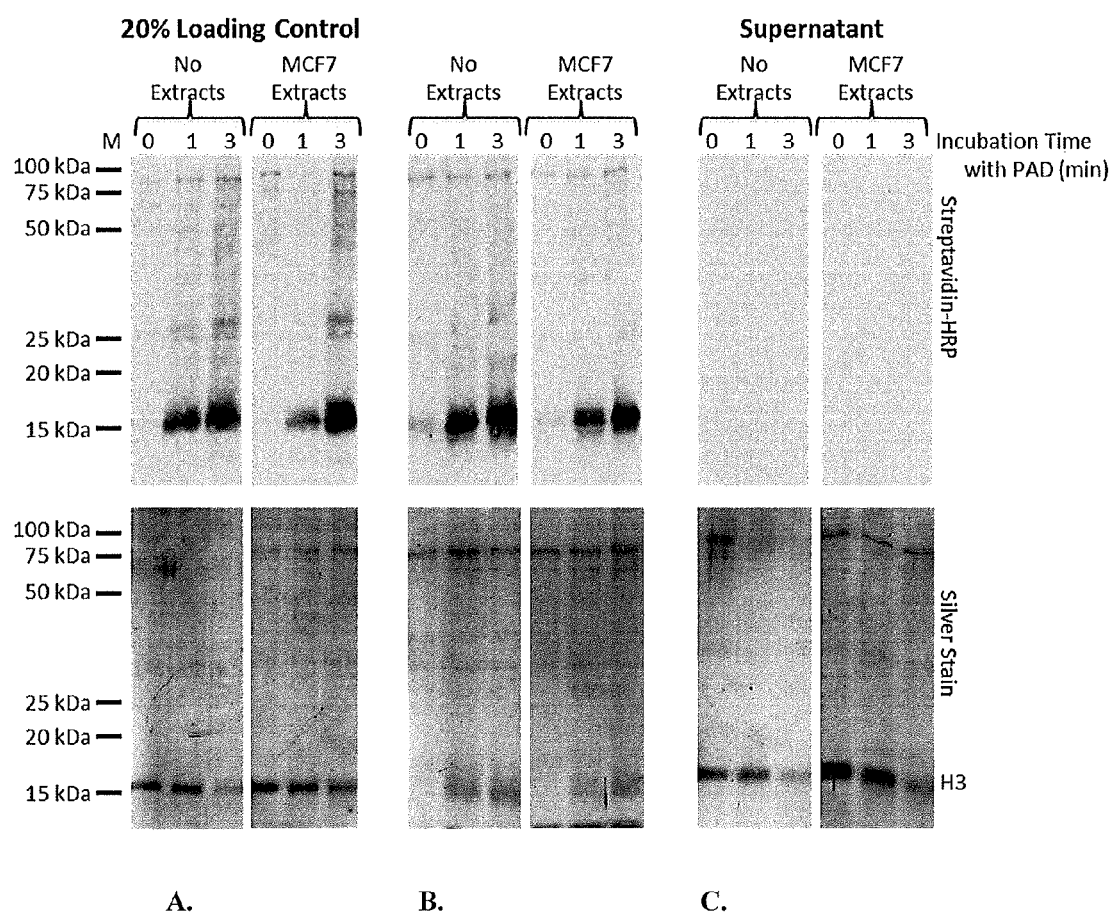

Having optimized conditions for using the probe, it was desired to demonstrate the ability of Biotin-PG to isolate citrullinated proteins via streptavidin-agarose pulldown. Histone H3, citrullinated by PAD2 for 0, 1, or 3 minutes, was treated with Biotin-PG with or without MCF whole cell extracts. Western blotting using streptavidin-HRP indicates that H3 is labeled by Biotin-PG (FIG. 22A) and is readily isolated (FIG. 22B) in a citrulline dependent manner, even from MCF7 extracts. Western blot analysis of the supernatant from the pulldown indicates complete isolation of Biotin-PG labeled citrullinated H3 (FIG. 22C). Overall, these data show that Biotin-PG is capable of selectively labeling and isolating citrullinated proteins.

Figures 23A, 23B:
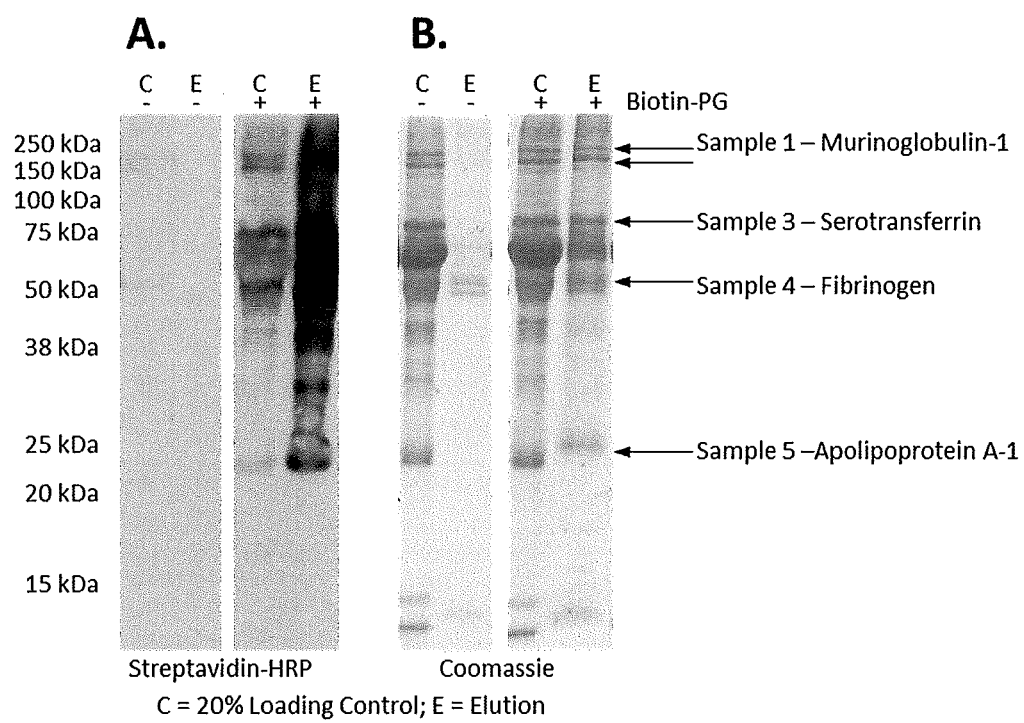
FIGS. 23A and 23B are blots showing Biotin-PG enrichment and proteomic identification of citrullinated proteins from ulcerative colitis mouse model. Serum samples from an ulcerative colitis mouse model study previously analyzed with the Rh-PG probe were treated with Biotin-PG, citrullinated proteins enriched with streptavidin agarose, and the eluted samples analyzed by (FIG. 23A) streptavidin-HRP Western blotting and (FIG. 23B) coomassie staining. Protein bands of good intensity that aligned with proteins previously correlated with UC disease severity were cut out and analyzed by tryptic digest and proteomic identification. Protein identity is indicated on the far right.

The true utility of the Biotin-PG probe lies in the ability to isolate and identify citrullinated biomarkers from various inflammatory diseases. To demonstrate this, serum samples from an ulcerative colitis mouse model study, previously analyzed with the Rh-PG probe, were treated with Biotin-PG. Citrullinated proteins were then enriched with streptavidin-agarose, and the eluted samples analyzed by Western blotting with streptavidin-HRP (FIG. 23A) and by coomassie staining (FIG. 23B). Protein bands with strong intensity that aligned with proteins previously correlated with UC disease severity were isolated from the SDS-PAGE gel and their identities determined by mass spectrometry of the in gel tryptic digests. Of the proteins identified, two were the proteinase inhibitors murinoglobulin and alpha-2-macroglobulin, which were labeled collectively as 100 kDa in the Rh-PG analysis. These proteins play a key role in regulating a number of proteases as well as altering the balance between pro- and anti-inflammatory cytokines (LaMarre, J et al., *Lab Invest* 1991, 65 (1), 3-14). The 70 kDa protein is serotransferrin, an iron transporter whose levels are known to be decreased during inflammation (Thanan, R., *Free Radic Biol Med* 2012, 52 (8), 1465-72). Fibrinogen-beta chain, a known PAD substrate was identified as the 50 kDa protein. Of particular interest was the protein at 25 kDa, which showed the strongest correlation with UC disease severity in the inventors' earlier studies (Bicker, K. L. et al., *J Am Chem Soc* 2012, 134 (41), 17015-8). This protein was identified as apolipoprotein-A1 (ApoA1), a key component of High Density Lipoprotein (HDL) which is important for homeostatic lipid metabolism. Destabilization of ApoA1 results in amyloid formation (Eriksson, M. et al., *J Mol Diagn* 2009, 11 (3), 257-62), and it may be that ApoA1, and other Apo family members, have protective roles in several inflammatory diseases such as ulcerative colitis and cancer (Vowinkel, T. et al., *J Clin Invest* 2004, 114 (2), 260-9).

Figures 24A, 24B, 24C:
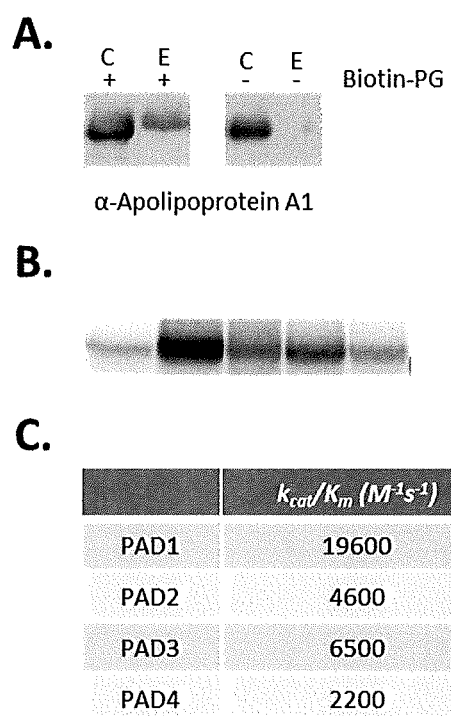
FIGS. 24A to 24C show the verification of novel disease biomarkers for ulcerative colitis. Verification of Apolipoprotein A1 (ApoA1) as a PAD substrate. The 25 kDa band from the Rh-PG analysis, which was the most correlative with UC disease severity, was identified as ApoA1 using the Biotin-PG probe.

To verify that ApoA1 is the modified 25 kDa protein in the UC samples, anti-ApoA1 Western blotting of Biotin-PG pulldown samples was performed (FIG. 24A). These results indicate that ApoA1 is only present in the pulldown sample first treated with Biotin-PG. This data confirms that citrullinated ApoA1 is present in the UC serum samples. To test human ApoA1 as a PAD substrate, recombinant huApoA1 was first treated ±PADs 1-4 and then analyzed with the Rh-PG probe (FIG. 24B). The strong increase in fluorescence observed with PAD1, indicates that ApoA1 is an excellent substrate for this enzyme. PADs 2, 3, and 4 also modified ApoA1, albeit to a lesser extent. To further evaluate citrullination of ApoA1, the steady state kinetic parameters were determined using Rh-PG. Consistent with the labeling data, ApoA1 is a highly efficient substrate for PAD1($k_{cat}/K_m$=19600 $M^{-1}s^{-1}$) and a modest substrate of PADs 2-4; the $k_{cat}/K_m$ values obtained with these enzymes are similar to those obtained for the histones (Slack, J. L. et al., *Biochemistry* 2011, 50 (19), 3997-4010). Taken together, these data provide evidence that ApoA1 citrullination strongly correlates with disease severity in a mouse model of ulcerative colitis and could serve as a potential biomarker for this and potentially other diseases.

What is claimed:

1. A method of synthesizing labeled phenylglyoxal (PG) probes, comprising:

reacting an acetophenone with a bromopropionyl bromide under a nitrogen (N2) atmosphere;

precipitating a resultant product, dissolving the product in a solvent, initiating a reaction by adding sodium azide (NaN$_3$) and producing a compound having a general structure 4:

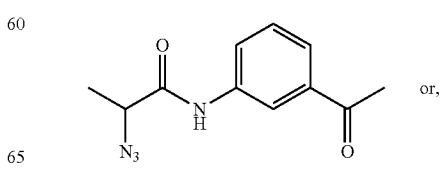

or,

-continued

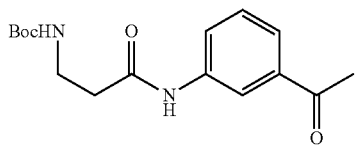

coupling a compound having a general structure 8 with a Boc-β-alanine; and, cleaving the Boc group and producing an azido-PG precursor having a general structure 9:

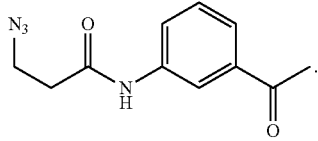

2. The method of claim 1, wherein the compound having the general structure 4 is refluxed under N₂ with a selenium dioxide (SeO₂), producing an azido phenylglyoxal (azido-PG) having a general structure 5:

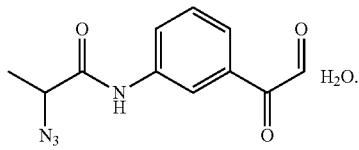

3. The method of claim 1, wherein the compound having the general structure 9 is refluxed under N₂ with a selenium dioxide (SeO₂), producing an azido-PG having a general structure 10:

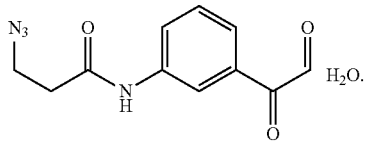

4. The method of claim 2 or 3, wherein the compounds having the general structures of compounds 5 and 10 are reacted with an alkyne comprising a reporter moiety.

5. The method of claim 1, wherein the reporter moiety comprises: fluorophores, isotopes, biotin, or rhodamine.

6. The method of claim 1, wherein the phenylglyoxal is linked to the reporter moiety via the meta position.

7. A method of testing bioavailability of Protein Arginine Deiminase (PAD) inhibitors comprising: contacting a biological sample with an effective amount of an isotopically labeled, fluorophore labeled, or biotin labeled phenylglyoxal (biotin-PG), wherein the isotopically labeled phenylglyoxal compound is heavy phenylglyoxal ($PG_H$) or light phenylglyoxal ($PG_L$) having a general structure I:

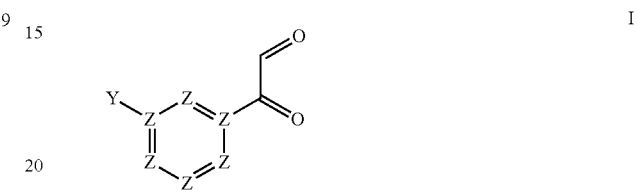

wherein Z is $^{13}C$ for heavy phenylglyoxal ($PG_H$), Z is $^{12}C$ for light phenylglyoxal ($PG_L$) and Y is H; or, a phenylglyoxal probe produced by the method of claim 1; and, assaying for the labeled proteins as compared to a control for testing the bioavailability of PAD inhibitors.

8. A method of identifying Protein Arginine Deiminase (PAD) inhibitors comprising: contacting a biological sample with an effective amount of an isotopically labeled, fluorophore labeled, or biotin labeled phenylglyoxal (biotin-PG), wherein the isotopically labeled phenylglyoxal compound is heavy phenylglyoxal ($PG_H$) or light phenylglyoxal ($PG_L$) having a general structure I:

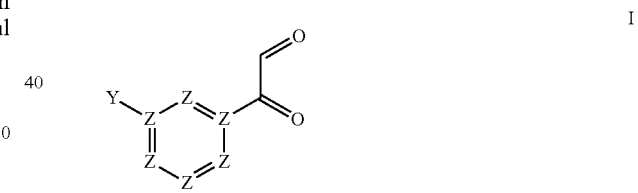

wherein Z $^{13}C$ is for heavy phenylglyoxal ($PG_H$), Z is $^{12}C$ for light phenylglyoxal ($PG_L$) and Y is H; or, a phenylglyoxal probe produced by the method of claim 1; and, assaying for citrullination of proteins as compared to a control.

* * * * *

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 1

Ser Gly Arg Gly Lys Gly Gly Lys Gly Leu Gly Lys Gly
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (3)..(3)
<223> OTHER INFORMATION: Cit
<220> FEATURE:
<223> OTHER INFORMATION: C-term amidated

<400> SEQUENCE: 2

Ser Gly Xaa Gly Lys Gly Gly Lys Gly Leu Gly Lys Gly
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (4)..(4)
<223> OTHER INFORMATION: Cit
<220> FEATURE:
<223> OTHER INFORMATION: C-term amidated

<400> SEQUENCE: 3

Ala His Ala Xaa Ala Cys Ala Arg Ala
1               5
```